US010842466B2

(12) United States Patent
Kang et al.

(10) Patent No.: US 10,842,466 B2
(45) Date of Patent: Nov. 24, 2020

(54) METHOD OF PROVIDING INFORMATION USING PLURALITY OF DISPLAYS AND ULTRASOUND APPARATUS THEREFOR

(71) Applicant: SAMSUNG ELECTRONICS CO., LTD., Suwon-si (KR)

(72) Inventors: Ho-kyung Kang, Seoul (KR); Jin-woo Yim, Seongnam-si (KR); Ki-won Sohn, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 982 days.

(21) Appl. No.: 14/884,531

(22) Filed: Oct. 15, 2015

(65) Prior Publication Data

US 2016/0106394 A1 Apr. 21, 2016

Related U.S. Application Data

(60) Provisional application No. 62/064,145, filed on Oct. 15, 2014.

(30) Foreign Application Priority Data

May 27, 2015 (KR) ........................ 10-2015-0074182

(51) Int. Cl.
*A61B 8/00* (2006.01)
*G01S 7/52* (2006.01)
(Continued)

(52) U.S. Cl.
CPC .............. *A61B 8/464* (2013.01); *A61B 8/465* (2013.01); *A61B 8/467* (2013.01); *A61B 8/54* (2013.01);
(Continued)

(58) Field of Classification Search
CPC ..... A61B 8/464; A61B 8/467; G01S 7/52084; G06F 3/041; G06F 2203/04101
See application file for complete search history.

(56) References Cited

U.S. PATENT DOCUMENTS 6,468,212 B1 10/2002 Scott et al.
8,016,759 B2 9/2011 Lee et al.
(Continued)

FOREIGN PATENT DOCUMENTS

CN 103079476 A 5/2013
CN 103945770 A 7/2014
(Continued)

OTHER PUBLICATIONS

Communication dated Oct. 30, 2017, issued by the Korean Intellectual Property Office in counterpart Korean Patent Application No. 10-2015-0074182.

(Continued)

*Primary Examiner* — Jeffrey G Hoekstra
*Assistant Examiner* — Jason M Ip
(74) *Attorney, Agent, or Firm* — Sughrue Mion, PLLC

(57) ABSTRACT

Provided is an ultrasound apparatus including a first display configured to display an ultrasound image; a control panel including a second display that is different from the first display and configured to display a plurality of control items related to the ultrasound image; and a controller configured to select at least one control item from among the plurality of control items based on a location of an input tool located on the second display, and to control the first display to display the selected at least one control item and an indicator representing the location of the input tool together with the ultrasound image.

13 Claims, 58 Drawing Sheets

(51) Int. Cl.
*G01S 15/89* (2006.01)
*G06F 3/0482* (2013.01)
*G06F 3/0484* (2013.01)
*G06F 3/041* (2006.01)
*G06F 3/0486* (2013.01)
*G06F 3/0488* (2013.01)

(52) U.S. Cl.
CPC ........ *G01S 7/52084* (2013.01); *G01S 15/899* (2013.01); *G06F 3/041* (2013.01); *G06F 3/0482* (2013.01); *G06F 3/0486* (2013.01); *G06F 3/04842* (2013.01); *G06F 3/04847* (2013.01); *G06F 3/04883* (2013.01); *G01S 7/52073* (2013.01); *G06F 2203/04101* (2013.01); *G06F 2203/04803* (2013.01); *G06F 2203/04804* (2013.01); *G09G 2320/0271* (2013.01); *G09G 2320/0606* (2013.01)

(56) References Cited

U.S. PATENT DOCUMENTS

| | | | |
|---|---|---|---|
| 8,151,188 | B2 | 4/2012 | Mahesh et al. |
| 9,285,961 | B2 | 3/2016 | Jo et al. |
| 2003/0105400 | A1 | 6/2003 | Yawata et al. |
| 2008/0146922 | A1* | 6/2008 | Steins ............... A61B 8/546 600/437 |
| 2009/0043195 | A1 | 2/2009 | Poland |
| 2011/0182137 | A1 | 7/2011 | Ozaki |
| 2012/0227006 | A1* | 9/2012 | Amm ............... G06F 1/169 715/773 |
| 2013/0090558 | A1 | 4/2013 | Jo et al. |
| 2013/0249842 | A1 | 9/2013 | Varna |
| 2014/0046185 | A1* | 2/2014 | Mo ............... A61B 8/461 600/443 |
| 2014/0088428 | A1 | 3/2014 | Yang et al. |
| 2014/0143687 | A1* | 5/2014 | Tan ............... G06F 3/1462 715/757 |
| 2014/0164965 | A1 | 6/2014 | Lee et al. |
| 2014/0325442 | A1 | 10/2014 | Eguchi et al. |
| 2015/0359516 | A1 | 12/2015 | Yang et al. |

FOREIGN PATENT DOCUMENTS

| | | | |
|---|---|---|---|
| EP | 2581044 | A2 | 4/2013 |
| EP | 2710960 | A1 | 3/2014 |
| EP | 2742869 | A1 | 6/2014 |
| JP | 2007-097816 | A | 4/2007 |
| KR | 10-2011-0136108 | A | 12/2011 |
| KR | 10-2014-0039954 | A | 4/2014 |
| KR | 10-2014-0076479 | A | 6/2014 |
| WO | 2013/077291 | A1 | 5/2013 |

OTHER PUBLICATIONS

Communication dated Dec. 28, 2017, issued by the Korean Intellectual Property Office in counterpart Korean Patent Application No. 10-2015-0074182.
Communication dated Apr. 21, 2017, issued by the Korean Intellectual Property Office in counterpart Korean application No. 10-2015-0074182.
Communication dated Jul. 27, 2018, issued by the Korean Patent Office in counterpart Korean Application No. 10-2015-0074182.
Communication dated Sep. 17, 2018, issued by the Korean Patent Office in counterpart Korean Application No. 10-2018-0098650.
Communication dated Jan. 22, 2016, issued by the International Searching Authority in counterpart International Application No. PCT/KR2015/010849 (PCT/ISA/220, PCT/ISA/210, PCT/ISA/237).
Communication dated Mar. 10, 2016, issued by the European Patent Office in counterpart European Application No. 15189927.5.
Communication dated Feb. 26, 2019 issued by the State Intellectual Property Office of P.R. China in counterpart Chinese Application No. 201580066390.5.
Communication dated Feb. 19, 2019 issued by the Korean Intellectual Property Office in counterpart Korean Application No. 10-2018-0098650.
Communication dated Apr. 25, 2019 issued by the Korean Intellectual Property Office in counterpart Korean Application No. 10-2018-0098650.
Communication dated Oct. 25, 2019, from the State Intellectual Property Office of People's Republic of China in counterpart Application No. 201580066390.5.
Communication dated Dec. 18, 2019, issued by the Korean Intellectual Property Office in corresponding Korean Application No. 10-2018-0098650.
Communication dated Apr. 17, 2020, issued by the Intellectual Property Office of P.R. China in counterpart Chinese Application No. 201580066390.5.

* cited by examiner

FIG. 30
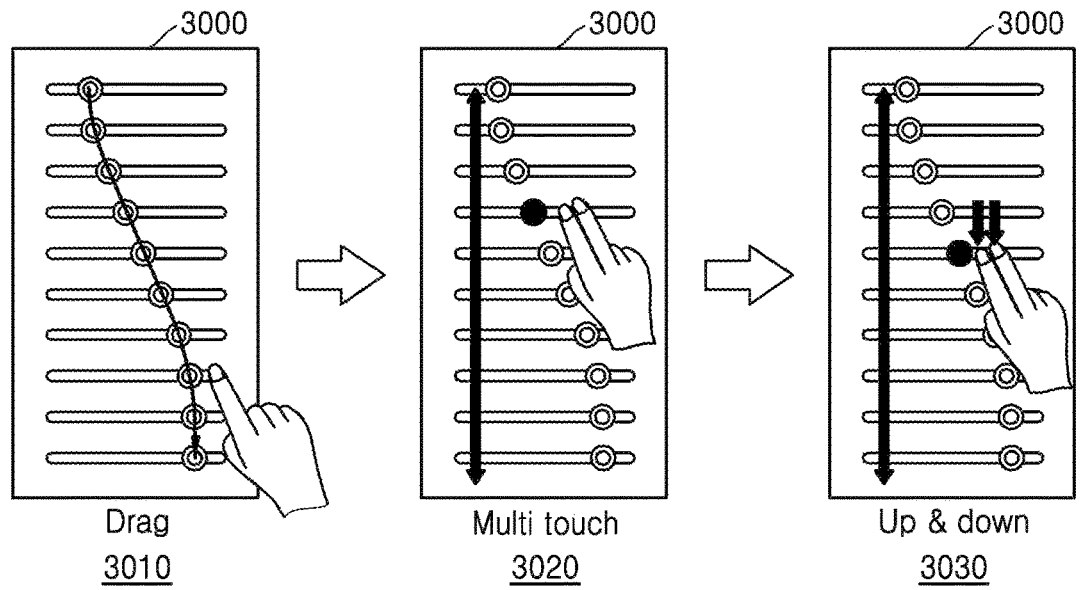
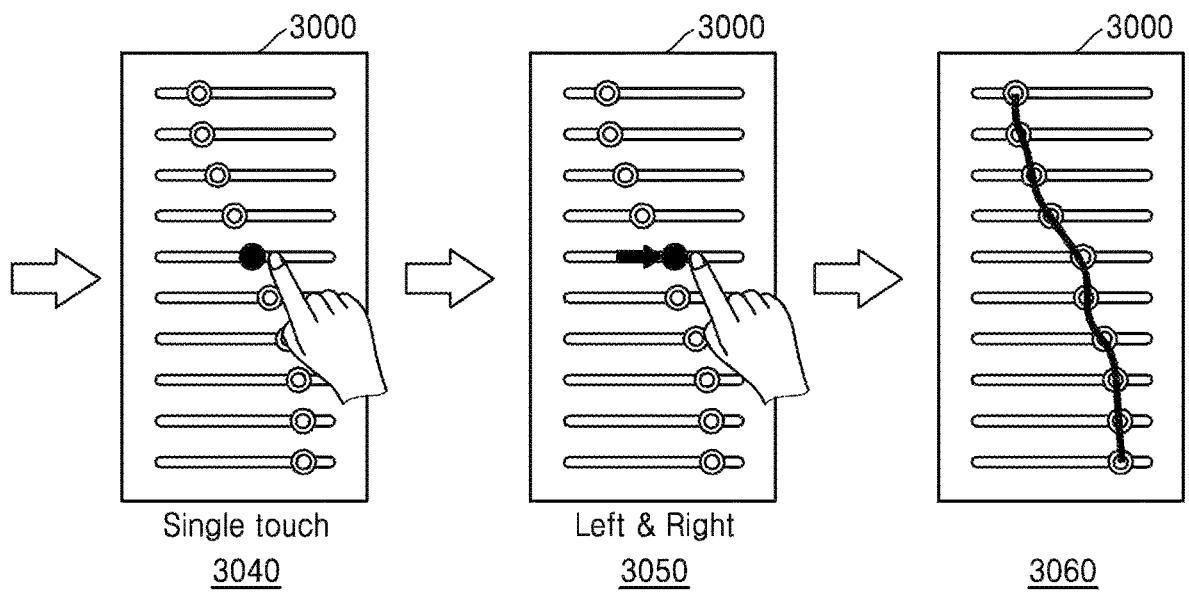

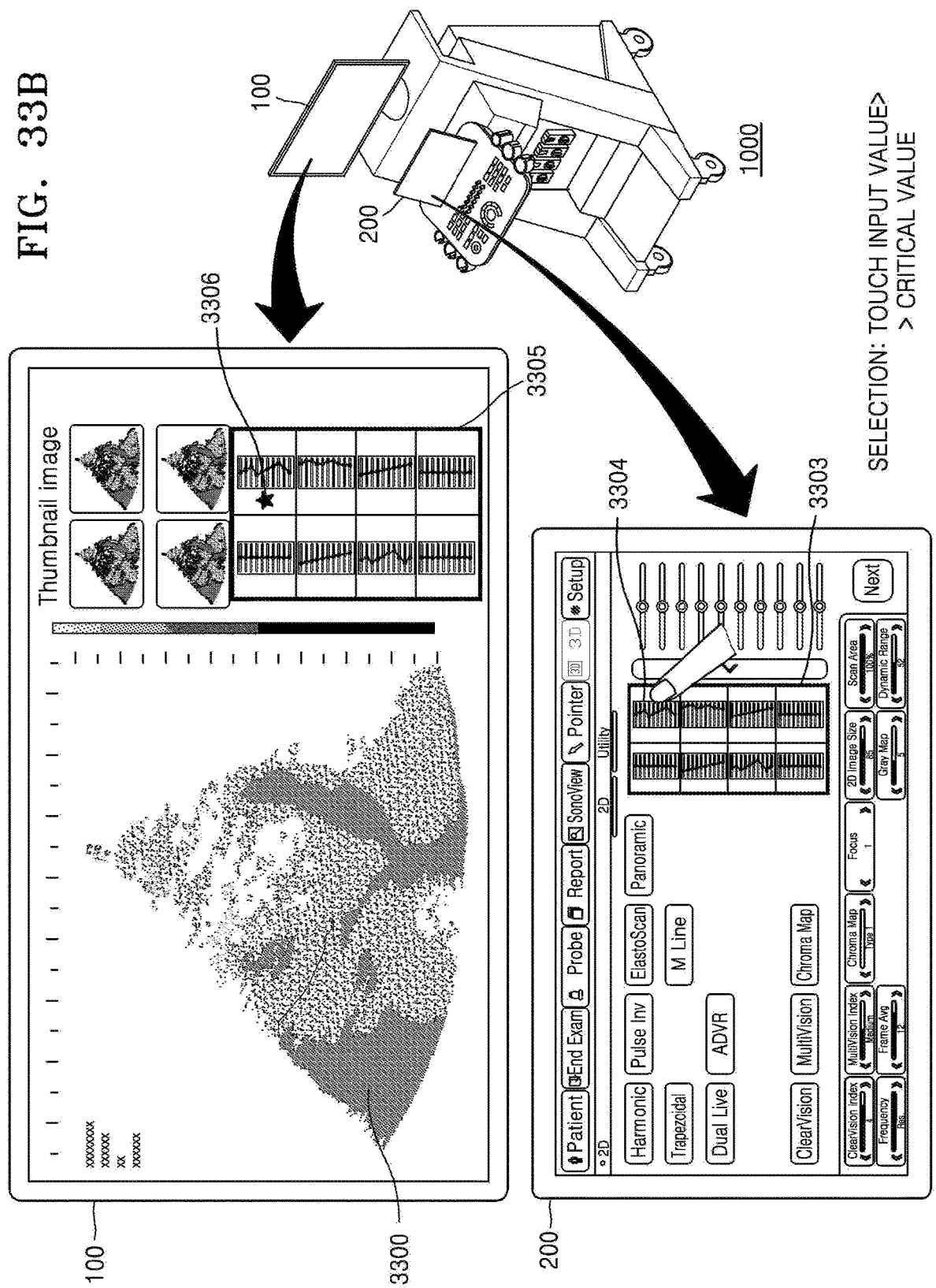

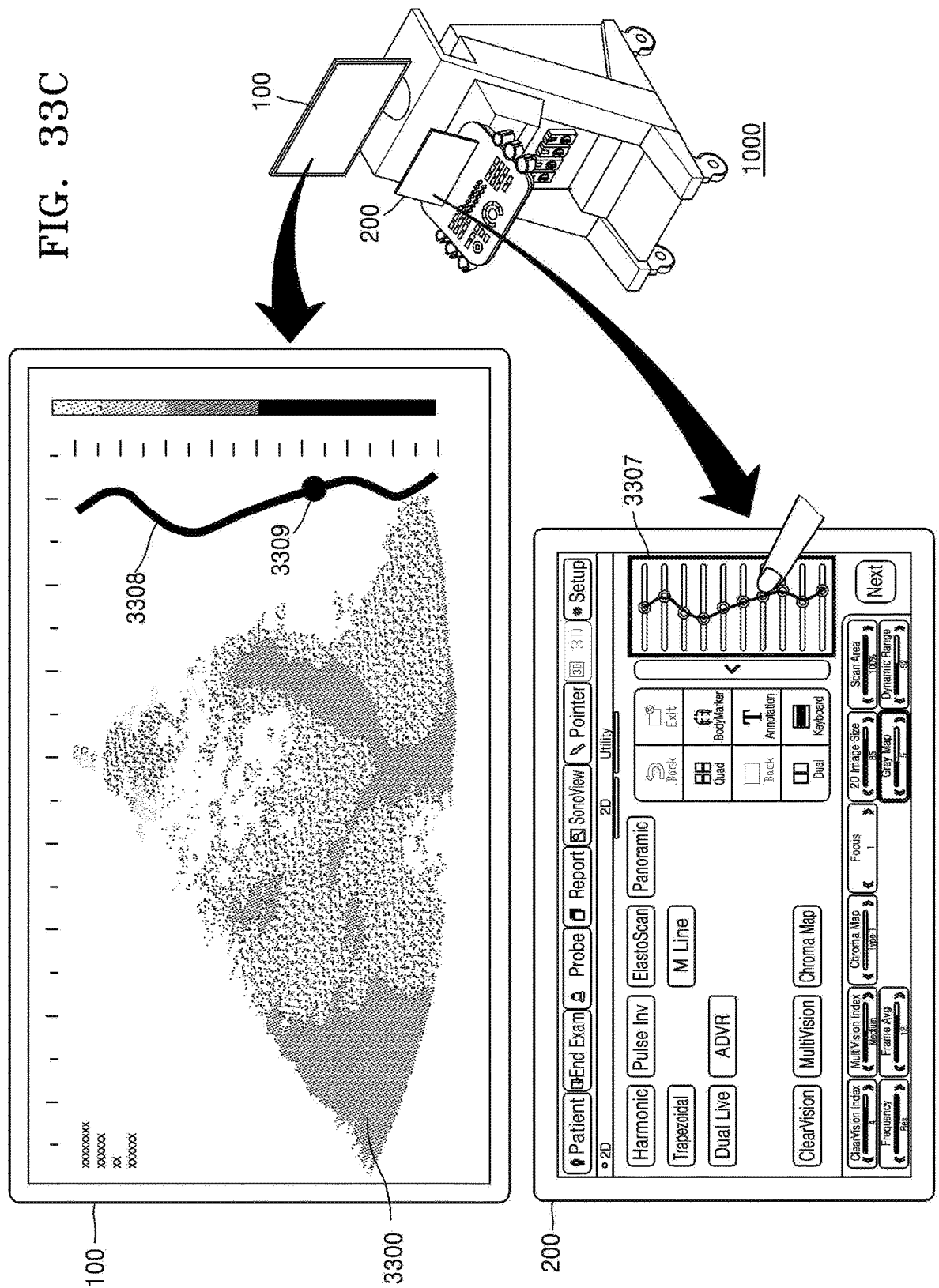

FIG. 35A
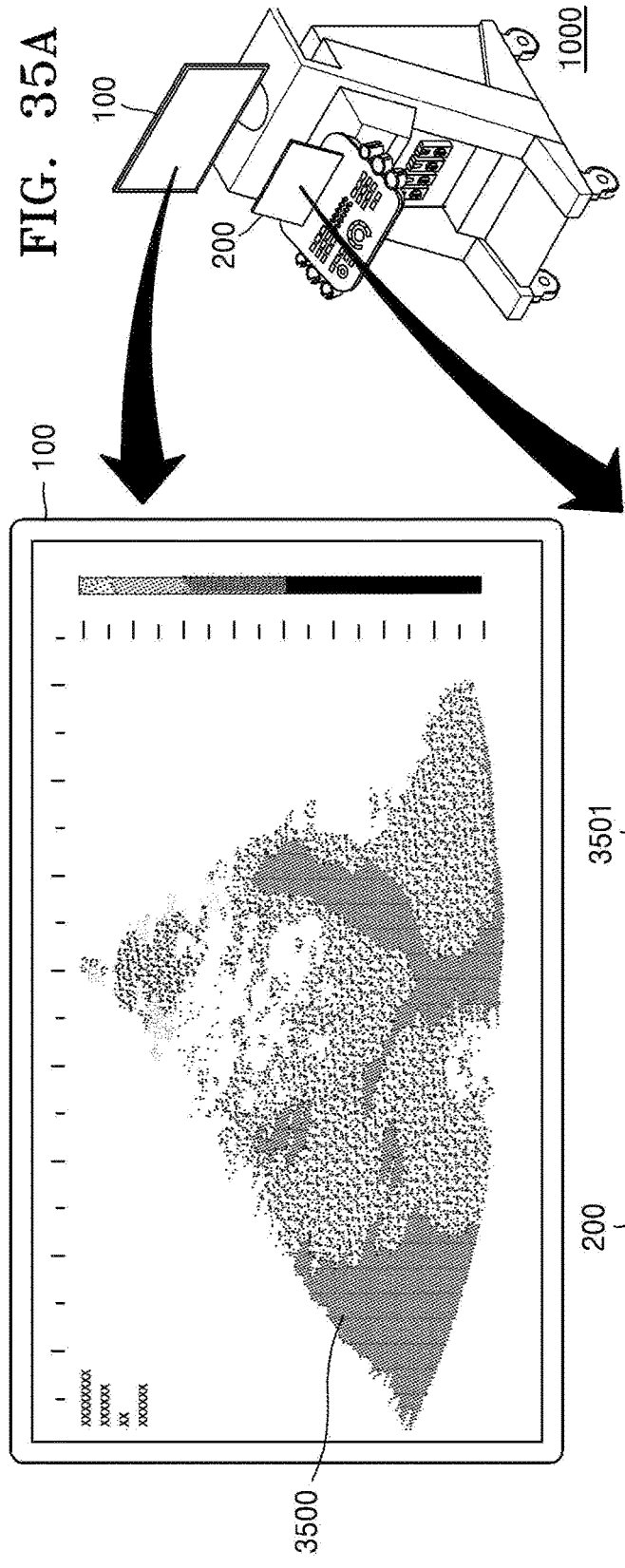
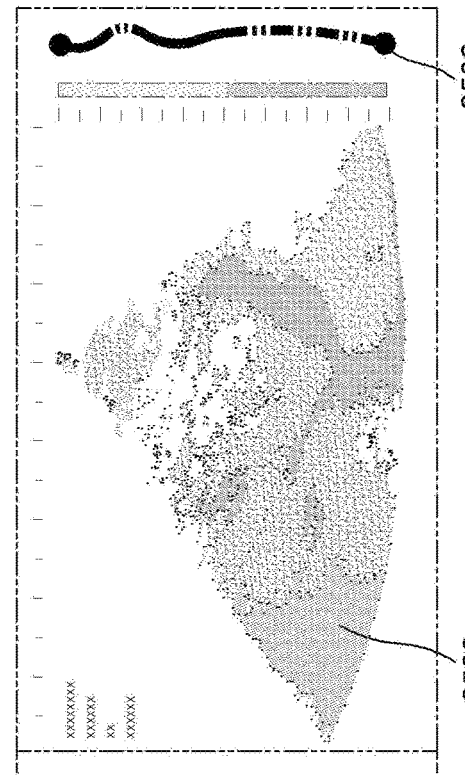
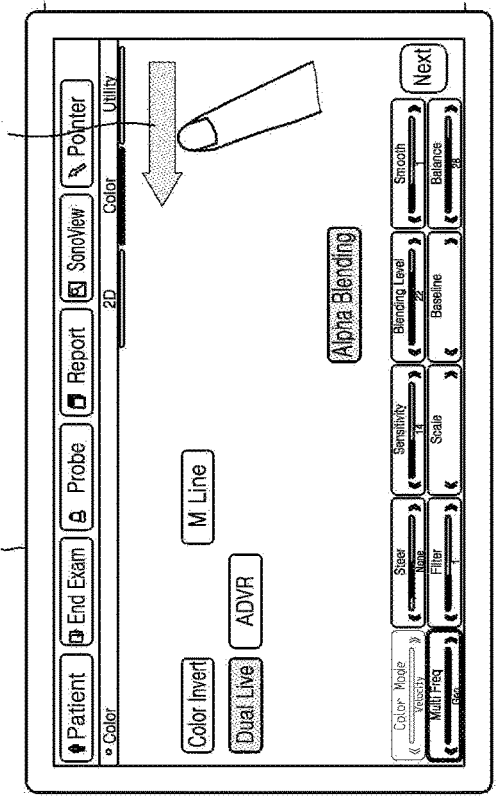
FIRST PAGE (3510)
SECOND PAGE (3520)

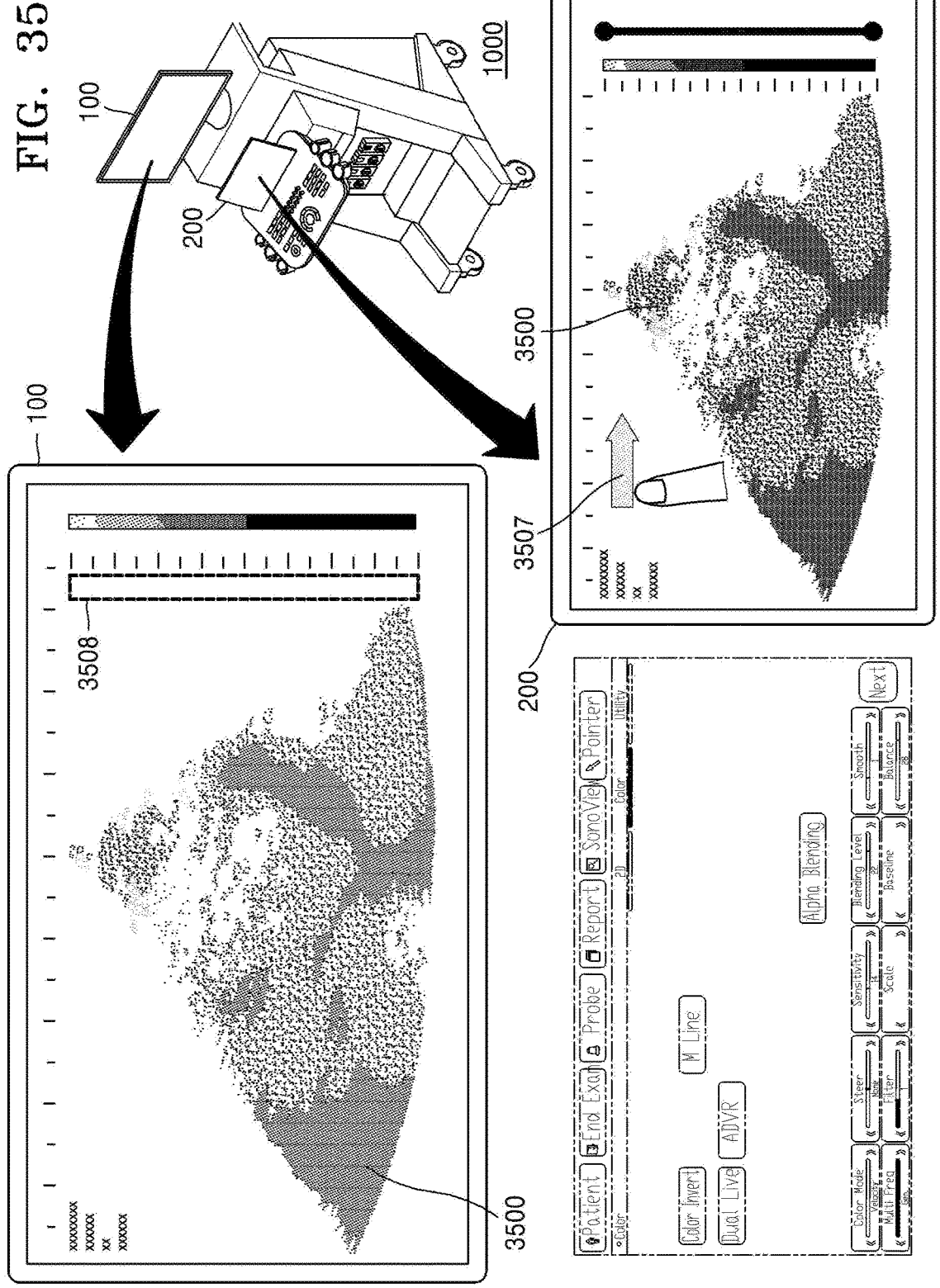

FIRST PAGE (3510)

METHOD OF PROVIDING INFORMATION USING PLURALITY OF DISPLAYS AND ULTRASOUND APPARATUS THEREFOR

CROSS-REFERENCE TO RELATED APPLICATION

This application claims priority from Korean Patent Application No. 10-2015-0074182, filed on May 27, 2015, in the Korean Intellectual Property Office, and the benefit of U.S. Patent Application No. 62/064,145, filed on Oct. 15, 2014, in the U.S. Patent and Trademark Office, the disclosures of which are incorporated herein in their entirety by reference.

BACKGROUND

1. Field

Apparatuses and methods consistent with exemplary embodiments include ultrasound apparatuses including a plurality of display units and methods of providing information by using a plurality of display units in the ultrasound apparatuses.

2. Description of the Related Art

An ultrasound diagnosis apparatus irradiates ultrasound signals to a target object inside a human body from the surface of the human body and receives ultrasound signals reflected from the target object, thereby obtaining images regarding tomography of soft tissues or blood flow based on information of the reflected ultrasound signals.

Such an ultrasound diagnosis apparatus may display information in real-time and may have a small size with a lower operating cost. An ultrasound diagnosis apparatus causes no radioactive exposure like an X-ray, and is therefore safer. Therefore, an ultrasound diagnosis apparatus is widely used together with other types of imaging diagnosis devices, including an X-ray diagnosis device, a computerized tomography (CT) scanner, a magnetic resonance image (MRI) device, a nuclear medical diagnosis device, etc.

SUMMARY

According to one or more exemplary embodiments, methods of providing information are provided so that the sight of a user is not directed out of a main screen while scanning ultrasound images, in an ultrasound apparatus including a plurality of display units.

Additional aspects will be set forth in part in the description which follows and, in part, will be apparent from the description, or may be learned by practice of the presented exemplary embodiments.

According to an aspect of an exemplary embodiment, an ultrasound apparatus includes: a first display configured to display an ultrasound image; a control panel including a second display that is different from the first display and configured to display a plurality of control items related to the ultrasound image; and a controller configured to select at least one control item from among the plurality of control items based on a location of an input tool located on the second display, and to control the first display to display the selected at least one control item and an indicator representing the location of the input tool together with the ultrasound image.

The ultrasound apparatus may further include at least one sensor configured to sense the location of the input tool located on the second display.

The at least one sensor may include at least one selected from a touch sensor, a pressure sensor, a proximity sensor, an image sensor, a depth sensor, and an infrared ray sensor.

The controller may be further configured to select the at least one control item based on whether the at least one control item is displayed within a predetermined distance from the location of the input tool.

The controller may be further configured to select the at least one control item by selecting a menu group corresponding to the location of the input tool, from among a plurality of menu groups displayed on the second display.

The controller may be further configured to display the indicator on the at least one control item.

The controller may be further configured to change a location of the indicator displayed on the first display, when the location of the input tool located on the second display changes.

The ultrasound image may include a real-time ultrasound image acquired via a probe.

The first display may be further configured to display the at least one control item and the indicator representing the location of the input tool so that the at least one control item and the indicator displayed by the first display overlay the ultrasound image.

The controller may be further configured to determine a transparency of the at least one control item displayed on the ultrasound image, based on predefined transparency information.

The controller may be further configured to display the ultrasound image on a first region of the first display and display the at least one control item and the indicator on a second region of the first display.

The controller may be further configured to receive a first input for selecting one control item from among the at least one control item via the second display, and the first input for selecting the control item may be different from a second input for changing the location of the indicator.

The controller may be further configured to display a window corresponding to the selected control item on the first display.

The controller may be further configured to display the ultrasound image displayed on the first display, on a predetermined region of the second display.

According to an aspect of an exemplary embodiment, a method of providing information via an ultrasound apparatus, the method includes: displaying an ultrasound image on a first display; displaying a plurality of control items related to the ultrasound image on a second display included in a control panel; selecting at least one control item from among the plurality of control items, based on a location of an input tool located on the second display; and displaying the selected at least one control item and an indicator representing the location of the input tool on the first display, together with the ultrasound image.

According to an aspect of an exemplary embodiment, an ultrasound apparatus includes: a first display configured to display an ultrasound image; a control panel including a second display that is different from the first display and configured to display a plurality of control items related to the ultrasound image; and a controller configured to select a first control item from among the plurality of control items based on a location of an input tool touching the second display, determine a second display format that is different from a first display format in which the first control item is displayed on the second display, and control the first display to display the selected first control item in the second display format.

The second display format may be simplified, i.e. may have less complexity, when compared with the first display format.

The controller may be further configured to sense the location of the input tool touching the first control item displayed in the first display format, and display an indicator representing the location of the input tool on the first control item displayed in the second display format.

The controller may be further configured to move the indicator displayed on the first control item displayed in the second display format, when the location of the input tool touching the first control item displayed in the first display format changes.

The controller may be further configured to receive a drag input on the first control item displayed in the first display format, and change the location of the indicator displayed on the first control item displayed in the second display format.

When the controller senses a touch input touching the first control item displayed in the first display format on the second display, the controller may be further configured to display the first control item in the second display format on the first display while continuing to display the first control item in the first display format on the second display.

The first display may be further configured to display the first control item in the second display format, so that the first control item displayed on the first display overlays the ultrasound image.

The first display may be further configured to display the ultrasound image on a first region of the first display and display the first control item in the second display format on a second region of the first display.

According to an aspect of an exemplary embodiment, a method of providing information via an ultrasound apparatus, the method includes: displaying an ultrasound image on a first display; displaying a plurality of control items related to the ultrasound image on a second display included in a control panel; selecting a first control item from among the plurality of control items, based on a location of an input tool touching the second display; determining a second display format that is different from a first display format in which the first control item is displayed on the second display; and displaying the first control item in the second display format on the first display, together with the first control item.

According to an aspect of an exemplary embodiment, an ultrasound apparatus includes: a first display configured to display an ultrasound image; a control panel including a second display configured to display a plurality of slide bars for adjusting gain values corresponding to depth sections of the ultrasound image on a first region; and a controller configured to control the first display to display a gain line together with the ultrasound image, wherein the gain line is determined by connecting gain values corresponding to locations of adjustment buttons on the plurality of slide bars based on a location of an input tool touching the second display.

The controller may be further configured to display an indicator representing a depth section corresponding to the location of the input tool on the first region, on the gain line displayed on the first display.

The controller may be further configured to move an indicator displayed on the gain line when the location of the input tool changes within the first region.

The controller may be further configured to receive an input for moving at least one of the adjustment buttons on the plurality of slide bars via the second display, move the at least one of adjustment button based on the input, and change a shape of the gain line displayed on the first display based on the location of the at least one adjustment button that has been moved.

The controller may be further configured to determine an input mode based on a touch gesture input via the input tool, which is sensed via the second display, and the input mode may include a depth selection mode for selecting one depth section from among the depth sections of the ultrasound image and a gain change mode for changing a gain value.

The controller may be further configured to determine that the input mode is the depth selection mode when the touch gesture of the input tool is a one-finger gesture, and determine that the input mode is the gain change mode when the touch gesture of the input tool is a multi-finger gesture.

The controller may be further configured to move the indicator displayed on the gain line to a first depth section in response to a first drag gesture dragging a finger upward or downward while the finger is in contact with the first region, adjust a gain value in the first depth section in response to a second drag gesture dragging at least two fingers in left or right directions while the at least two fingers are in contact with the first region, and change the shape of the gain line displayed on the first display based on the adjusted gain value.

The controller may be further configured to receive an input for selecting one of a plurality of preset gain value sets via the second display, and move at least one adjustment button among the adjustment buttons on the plurality of slide bars according to the selected preset gain value set.

The controller may display a gain line corresponding to the selected preset gain value set on the first display.

According to an aspect of an exemplary embodiment, a method of providing information via an ultrasound apparatus, the method includes: displaying an ultrasound image on a first display; displaying a plurality of slide bars for adjusting gain values corresponding to depth sections of the ultrasound image on a second display included in a control panel; and displaying a gain line on the first display together with the ultrasound image, wherein the gain line is determined by connecting gain values corresponding to locations of adjustment buttons on the plurality of slide bars based on a location of an input tool touching the second display.

According to an aspect of an exemplary embodiment, an ultrasound apparatus includes: a first display configured to display an ultrasound image; a control panel including a second display that is different from the first display and configured to display a first gain line for setting gain values corresponding to depth sections of the ultrasound image; and a controller configured to control the first display to display a second gain line together with the ultrasound image, based on a touch input touching the first gain line displayed on the second display, wherein the second gain line displayed on the first display corresponds to the first gain line displayed on the second display.

The controller may be further configured to extract a plurality of gain values represented by points of the first gain line in response to the touch input touching the first gain line displayed on the second display, and generate the second gain line based on the plurality of extracted gain values.

The controller may be further configured to determine a length of the second gain line based on an entire depth value of the ultrasound image displayed on the first display.

The first display may be further configured to display the second gain line at a side of the ultrasound image such that depth values represented by points of the second gain line correspond to depth values of the ultrasound image.

The controller may be further configured to display the second gain line on the first display such that an uppermost point of the second gain line corresponds to a lowest depth value of the ultrasound image and a lowermost point of the second gain line corresponds to a highest depth value of the ultrasound image.

The first gain line and the second gain line may be obtained by connecting gain values corresponding to the depth sections of the ultrasound image.

The first display may be further configured to display the ultrasound image on a first region of the first display and display the second gain line on a second region of the first display.

The controller may be further configured to display an indicator representing a touched location on the first gain line on the second gain line.

The controller may be further configured to move the indicator displayed on the second gain line when the touched location on the first gain line changes.

When the controller receives an input for changing a first gain value set corresponding to the first gain line to a second gain value set via the first gain line, the controller may be further configured to change a shape of the second gain line displayed on the first display based on the second gain value set.

When the touch input on the first gain line ends, the controller may be further configured to stop displaying the second gain line.

According to an aspect of an exemplary embodiment, a method of providing information via an ultrasound apparatus, the method includes: displaying an ultrasound image on a first display; displaying a first gain line for setting gain values corresponding to depth sections of the ultrasound image on a second display included in a control panel; and displaying a second gain line on the first display, together with the ultrasound image, based on a touch input on the first gain line displayed on the second display, wherein the second gain line displayed on the first display corresponds to the first gain line displayed on the second display.

According to an aspect of an exemplary embodiment, a non-transitory computer readable medium comprising instructions is provided. The instructions are executable by a processor to perform: displaying an ultrasound image on a first display; displaying, on a second display of a control panel that is separate from the first display, a plurality of control items configured to control to adjust the ultrasound image; selecting at least one control item from among the plurality of control items based on a location of an input tool corresponding to the second display; and controlling the first display to display the selected at least one control item and an indicator representing the location of the input tool together with the ultrasound image.

The instructions may be executable by a processor to further perform: detecting, by a sensor, the location of the input tool corresponding to the second display.

The at least one sensor may comprise at least one selected from among a touch sensor, a pressure sensor, a proximity sensor, an image sensor, a depth sensor, and an infrared ray sensor.

The instructions may be executable by a processor to further perform: selecting the at least one control item based on whether the at least one control item is displayed within a predetermined distance from the location of the input tool.

BRIEF DESCRIPTION OF THE DRAWINGS

These and/or other aspects will become apparent and more readily appreciated from the following description of the exemplary embodiments, taken in conjunction with the accompanying drawings in which:

FIG. 30 is a diagram illustrating an example, in which an ultrasound apparatus determined an input mode related to a TGC based on a kind of a touch gesture, according to an exemplary embodiment;

FIGS. 33A to 33C are diagrams illustrating an example of providing information about a predetermined gain value set selected by a user via a touch screen and a main screen, according to an exemplary embodiment;

FIGS. 35A to 35F are diagrams illustrating an example, in which an ultrasound apparatus displays a gain line on a touch screen and a main screen, according to an exemplary embodiment.

DETAILED DESCRIPTION

Figure 1:
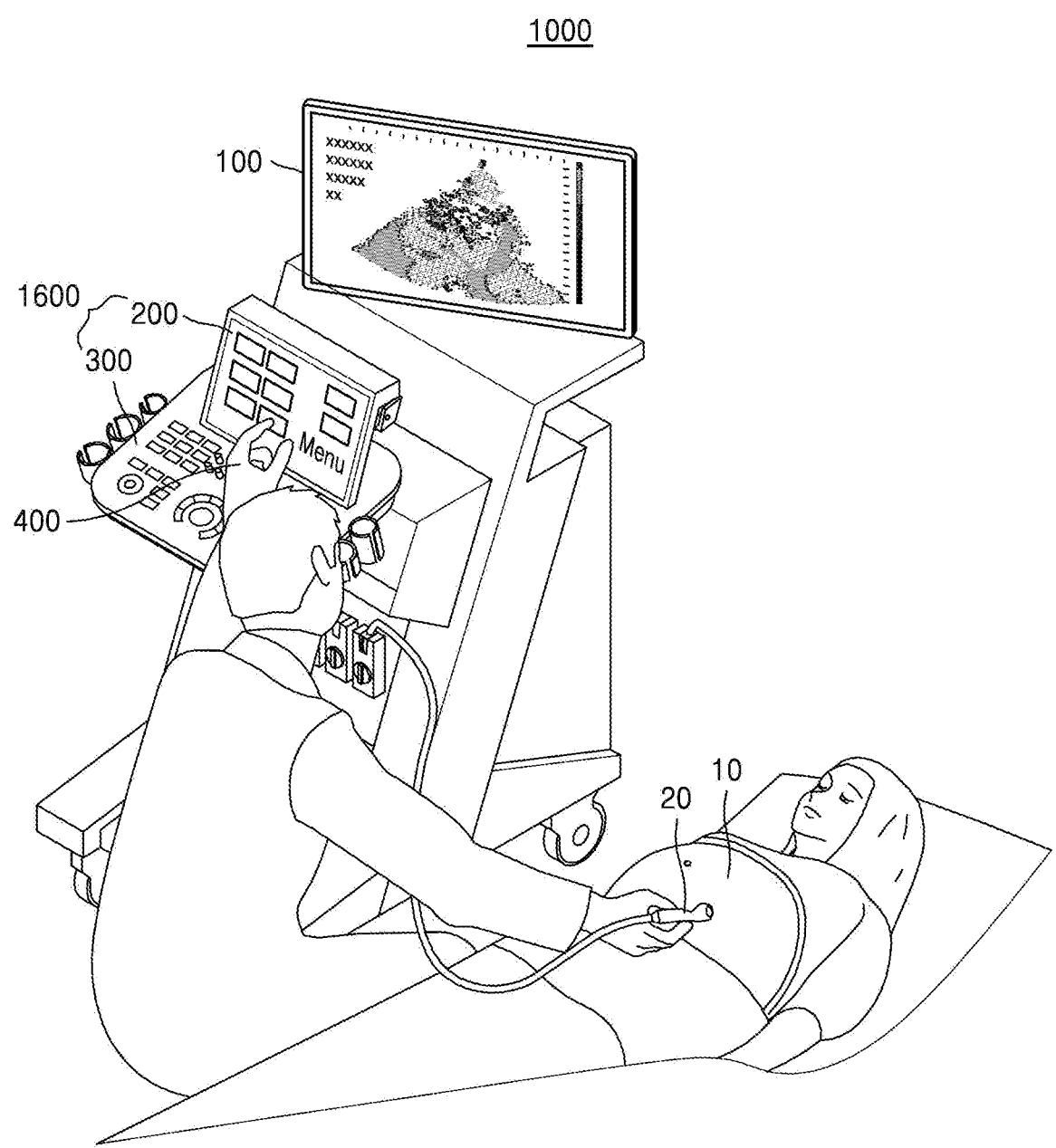
FIG. 1 is a diagram of an ultrasound apparatus including a plurality of display units according to an exemplary embodiment.

All terms including descriptive or technical terms which are used herein should be construed as having meanings as understood by one of ordinary skill in the art. However, the terms may also have different meanings according to the intention of one of ordinary skill in the art, precedent cases, or the appearance of new technologies. Some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software. As used herein, the term "and/or" includes any and all combinations of one or more of the associated listed items. Expressions such as "at least one of," when preceding a list of elements, modify the entire list of elements and do not modify the individual elements of the list.

Throughout the specification, "ultrasound image" denotes an image of an object obtained by using ultrasound signals. In the specification, an "object" may include a human, an animal, or a part of a human or animal. For example, the object may be an organ (e.g., the liver, the heart, the womb, the brain, a breast, or the abdomen), a blood vessel, or a combination thereof. The object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a medical doctor, a nurse, a medical laboratory technologist, and a sonographer.

Reference will now be made in detail to exemplary embodiments, which are illustrated in the accompanying drawings. In this regard, the exemplary embodiments may have different forms and should not be construed as being limited to the descriptions set forth herein. In the following description, well-known functions or constructions are not described in detail since they would obscure the exemplary embodiments with unnecessary detail. Like reference numerals refer to like elements throughout the specification.

FIG. 1 is a diagram of an ultrasound apparatus 1000 including a plurality of display units, according to an exemplary embodiment.

Referring to FIG. 1, the ultrasound apparatus 1000 according to the exemplary embodiment may include a first display unit 100 (e.g., display, monitor, etc.), an input device

1600, and an interface for connecting to a probe 20. Here, the input device 1600 may include a second display unit 200 (e.g., display, monitor, etc.) displaying a graphical user interface (GUI) and a control panel 300 including a hardware button. Hereinafter, each element of the ultrasound apparatus 1000 will be described in detail below. The first display unit 100 and the second display unit 200 may operate independently or separately, be different from each other, or be separate. According to an exemplary embodiment, the control panel 300 may include the second display unit 200 displaying the graphical user interface (GUI).

According to an exemplary embodiment, the first display unit 100 may be a main screen displaying ultrasound images or information of an object. A user may recognize a status of the object 10 via an ultrasound image displayed on the first display unit 100. For example, the user may detect a lesion or may identify health status of an embryo through the ultrasound image displayed on the first display unit 100.

According to the exemplary embodiment, the first display unit 100 may be connected to a body of the ultrasound apparatus 1000. Here, a connection portion connecting the first display unit 100 and the body of the ultrasound apparatus 1000 to each other may be rotatable. The user may rotate the connection portion for connecting the first display unit 100 to the body so as to adjust an angle between the body of the ultrasound apparatus 1000 (or a reference axis of the body) and the first display unit 100.

For example, the user may rotate the connection portion for connecting the first display unit 100 to the body in order to identify an ultrasound image acquired via the probe 20 without turning his/her head, in a state of holding the probe 20 with his/her hand and placing the probe 20 on abdomen of the object. If the ultrasound apparatus 1000 including the first display unit 100 is located at a left side of the user and the object 10 is located at a right side of the user, the user may rotate the connection portion by an angle of 30° in a counter-clockwise direction in order to adjust the first display unit 100 to face the object 10.

The first display unit 100 according to the exemplary embodiment may include at least one selected from a liquid crystal display (LCD), a thin film transistor (TFT)-LCD, an organic light-emitting diode (OLED), a flexible display, and a three-dimensional (3D) display, but is not limited thereto. The first display unit 100 may include a touch panel (e.g., a capacitive overlay type, a resistive overlay type, an infrared beam type, a surface acoustic wave type, an integral strain gauge type, and a piezoelectric type).

The input device 1600 according to the exemplary embodiment is a unit through which the user inputs data for controlling the ultrasound apparatus 1000. For example, the input device 1600 may include the second display unit 200 for displaying the GUI, and the control panel 300 including hardware buttons.

According to the exemplary embodiment, the second display unit 200 may include a touch screen. For example, the second display unit 200 and the touch pad may be layered to form a touch screen. Then, the second display unit 200 may be used as an input device.

The touch screen may be configured to detect a pressure of a touch input, as well as a touch input location and a touched area. The touch screen may be configured to detect a proximity touch, as well as a real touch.

Throughout the present specification, "real touch" denotes a case where a pointer 400 really touches the touch screen, and "proximity touch" denotes a case where the pointer 400 is not actually touching the touch screen, but approaches the touch screen with a predetermined interval. Throughout the specification, pointer 400 is a touch tool for touching or approximating a certain point on the displayed screen, for example, an electronic pen, a finger, etc. For the convenience of description, an example in which the pointer 400 is a finger will be described below. In addition, the pointer 400 may be referred to as an input tool.

The ultrasound apparatus 1000 may include various sensors in the touch screen or around the touch screen in order to sense or detect the real touch or proximity touch onto the touch screen. An example of the sensor for sensing the touch on the touch screen may include a tactile sensor.

The tactile sensor senses a contact of a certain material at an intensity that a human being may feel or greater. The tactile sensor may sense various information such as roughness of a contacting surface, firmness or solidity of a contact material, a temperature at a contact point, etc.

An example of the sensor for sensing the touch on the touch screen may be a proximity sensor. The proximity sensor is a sensor for detecting whether an object approaches a detection surface or whether the external object is present nearby by using a force of an electromagnetic field or an infrared ray without an actual physical touch.

Examples of the proximity sensor include a transparent photoelectric sensor, a direct reflective photoelectric sensor, a mirror reflective photoelectric sensor, a high frequency oscillation photoelectric sensor, a capacitive photoelectric sensor, a magnetic photoelectric sensor, an infrared photoelectric sensor, etc.

According to the exemplary embodiment, the second display unit 200 may sense a touch gesture of the user via the touch screen. Throughout the present specification, touch gestures (touch inputs) of the user may include a tap, a touch and hold, a double tap, a drag, panning, a flick, a drag and drop, a swipe, a pinch, etc.

"Tap" refers to an operation in which the user touches the screen by using a finger or an electronic pen and then lifts the finger or the electronic pen from the screen without moving it on the screen.

"Touch & hold" is an operation in which the user touches the screen by using a finger or an electronic pen and maintains the touch input for a critical length of time (for example, two seconds) or longer. That is, a time difference between a touch-in time and a touch-out time is equal to or greater than the critical length of time (for example, two seconds). In order for the user to recognize whether the touch input is the tap operation or the touch & hold operation, a visual, an audible, or a tactile feedback signal is transmitted when the touch input is maintained for the critical length of time or longer. The critical length of time may vary depending on an exemplary embodiment.

"Double tap" is an operation in which the user touches the screen twice by using the finger or the electronic pen.

"Drag" is an operation in which the user touches the screen by using a finger or an electronic pen and then moves the finger or the electronic pen to another position on the screen while continuously touching the screen. An object is moved or a panning operation that will be described later is performed by the drag operation.

"Panning" is an operation in which the user performs the drag operation without selecting an object. Since the user does not select a certain object in the panning operation, a page itself moves in the screen or a group of objects moves in the page, without moving the certain object in the page.

"Flick" is an operation in which the user drags a finger or an electronic pen at a critical speed (for example, 100 pixel/s) or faster. The drag operation (or panning operation) and the flick operation may be distinguished from each other based on whether the velocity of the finger or the electronic pen is the critical speed (for example, 100 pixel/s) or greater.

"Drag & drop" is an operation in which the user drags and drops an object at a predetermined location on the screen by using the finger or the electronic pen.

"Pinch" is an operation in which the user touches the screen by using two fingers and then moves the fingers to different directions from each other. The pinch operation is a gesture for expanding (pinch open) or reducing (pinch close) the object or the page, and an expansion value or a reduction value may be determined by a distance between the two fingers.

"Swipe" is an operation in which the user moves the finger or the electronic pen a predetermined distance in a horizontal or a vertical direction in a state of touching the object on the screen. Movement in a diagonal direction may not be considered as a swipe event.

In addition, the second display unit 200 according to the exemplary embodiment may include a plurality of control items. The plurality of control items are user-selectable items, e.g., a menu, an adjustment button, a mode selection button, a shortcut icon, an adjustment interface, a functional key, a setting window, etc., but are not limited thereto.

According to the exemplary embodiment, each of the plurality of control items may be associated with at least one function. For example, the plurality of control items may include a two-dimensional (2D) button, a 3D button, a four-dimensional (4D) button, a color button, a PW button, an M button, a sonoview button (a button for identifying an image stored previously), a more button, a measure button, an annotation button, a Biopsy button (a button for guiding an insertion point of a needle), a depth button, a focus button, a gain button, a frequency button, etc., but are not limited thereto. Functions of each button may be easily deducted from name on the button by one of ordinary skill in the art, and thus, detailed descriptions about the buttons are omitted here.

According to the exemplary embodiment, the control panel 300 may include hardware buttons (physical buttons). For example, the control panel 300 may include hardware buttons such as a track ball, a probe button, a power button, a scan button, a patient button, an ultrasound image selection button, etc., but is not limited thereto.

The patient button is a button for selecting a patient who will be ultrasound image diagnosed, and the probe button is a button for selecting a probe used in the ultrasound image diagnosis. The scan button is a button for correcting the ultrasound image rapidly by using a parameter value set in advance in the ultrasound apparatus 1000, a storage button is a button for storing the ultrasound image, and the ultrasound image selection button is a button for pausing displaying of ultrasound images displayed in real-time to show a still ultrasound image on the screen.

According to the exemplary embodiment, the hardware buttons included in the control panel 300 may be realized by software to be displayed on the second display unit 200. For example, a freeze button for displaying a still image may exist as a hardware button on the control panel 300, and may exist as a software button on the second display unit 200. The software button may be a user interface (UI) object realized as software and displayed on the screen. For example, the software button may include an icon, a setting key, a menu, etc. displayed on the touch screen. Functions matched with the software buttons may be executed by a touch input for touching the software buttons.

According to the exemplary embodiment, from among the buttons included in a control panel of a general ultrasound apparatus that does not include a touch screen, some of the buttons, which are frequently used by the user, may be included in the control panel 300 as hardware buttons, and the other buttons may be provided on the touch screen of the second display unit 200 as GUI.

In a case of the hardware buttons formed on the control panel 300, the user may easily select a certain button from among the hardware buttons by using a tactile feeling without seeing the control panel 300.

However, locations of the software buttons provided on the touch screen may be variable, and thus, it is difficult for the user to identify locations of the software buttons without seeing the software buttons. In addition, the user may feel difficulty in recognizing boundaries between the software buttons through the tactile sensation. Therefore, the user has to select a certain software button displayed on the touch screen while identifying a location of the finger on the touch screen.

For example, in order for the user to select a button displayed on the touch screen while performing an ultrasound diagnosis (e.g., scanning ultrasound images), the user has to turn his/her eyes away from the ultrasound image displayed on the main screen to the touch screen. In this case, user's eyes may be dispersed between the first display unit 100 displaying the ultrasound image and the second display unit 200 displaying the control items (e.g., menus).

Therefore, according to the exemplary embodiment, some or all of the control items (e.g., menus) displayed on the second display unit 200 are displayed on the first display unit 100, that is, the main screen, based on a location of the pointer 400 touching the second display unit 200, and thus, the user's eyes may not be dispersed during performing the ultrasound diagnosis.

In addition, an example in which the first display unit 100 is the main screen displaying the ultrasound images and the second display unit 200 is the touch screen displaying the control items will be described below.

Although FIG. 1 shows the second display unit 200 and the control panel 300 that are separate from each other, one or more exemplary embodiments are not limited thereto. In some exemplary embodiments, the control panel 300 may include the second display unit 200.

In addition, if the input device 1600 only includes the touch screen, the control panel 300 and the second display unit 200 may be formed integrally with each other. A case where the entire control panel 300 is the touch screen will be described below with reference to FIG. 2A.

Figure 2A:
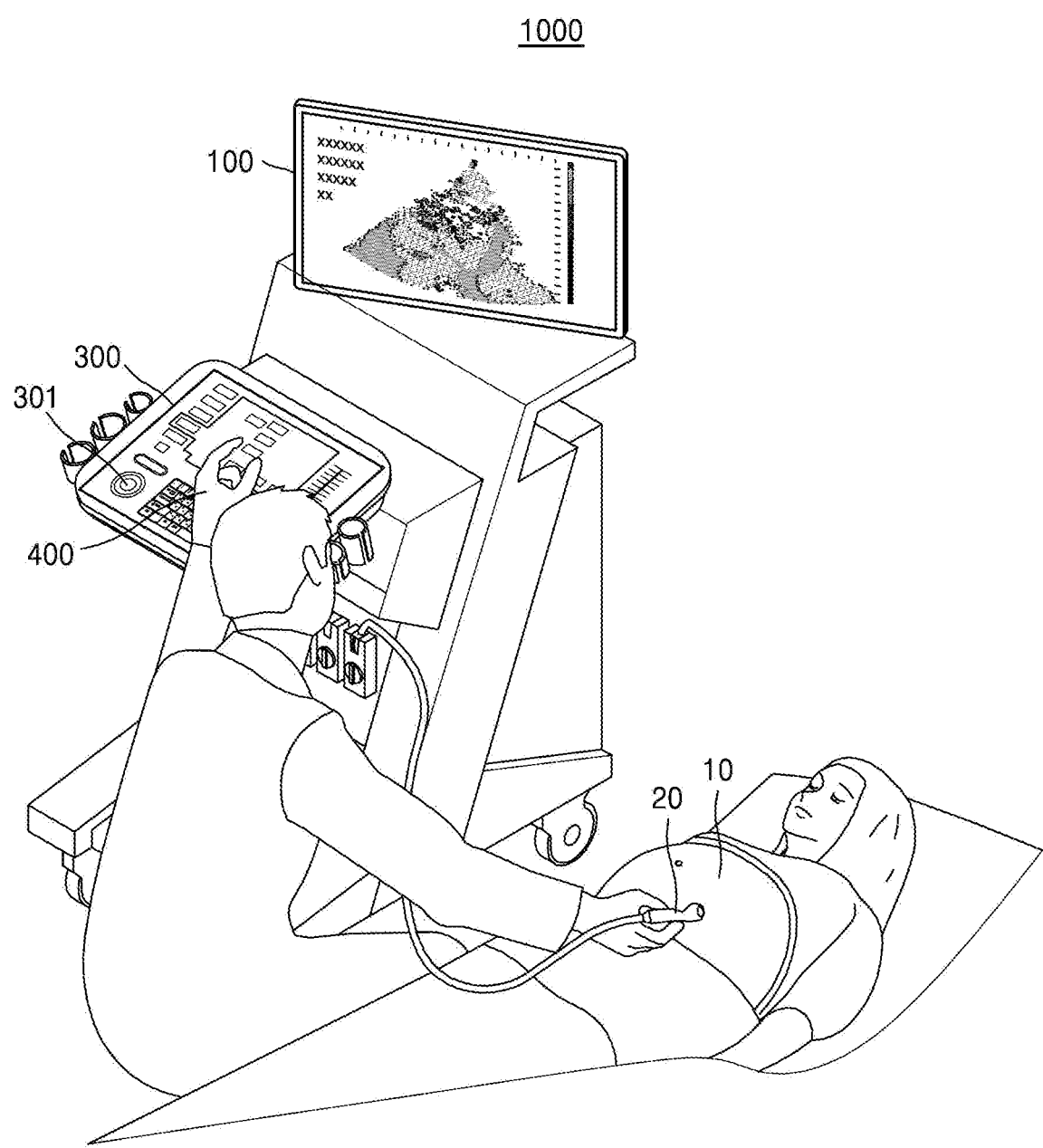
FIG. 2A is a diagram of an ultrasound apparatus including a control panel that is entirely formed of a touch screen, according to an exemplary embodiment.

FIG. 2A is a diagram of an ultrasound apparatus including the control panel 300 that is entirely a touch screen, according to an exemplary embodiment.

Referring to FIG. 2A, the entire control panel 300 may be a touch screen. In this case, the control panel 300 may denote the second display unit 200. Therefore, software buttons may be displayed on the control panel 300, instead of the hardware buttons. For example, the control panel 300 may display at least one control item. In addition, the control panel 300 may reduce the ultrasound image displayed on the first display unit 100 by a ratio, and display the reduced ultrasound image on a region thereof.

According to an exemplary embodiment, the control panel 300 may include a track ball 301 on a portion thereof. Here, when the user rotates the track ball 301 with his/her finger, a cursor on the first display unit 100 may be moved according to movement of the track ball 301.

FIGS. 1 and 2A shows a case in which the first display unit 100 and the second display unit 200 are attached to the body of the ultrasound apparatus 1000 as an example, but one or more exemplary embodiments are not limited thereto. For example, a case in which the second display unit 200 is detached from the ultrasound apparatus 1000 will be described below with reference to FIG. 2B, and a case in which the first display unit 100 exists outside of the ultrasound apparatus 1000 will be described below with reference to FIG. 3 in detail.

Figure 2B:
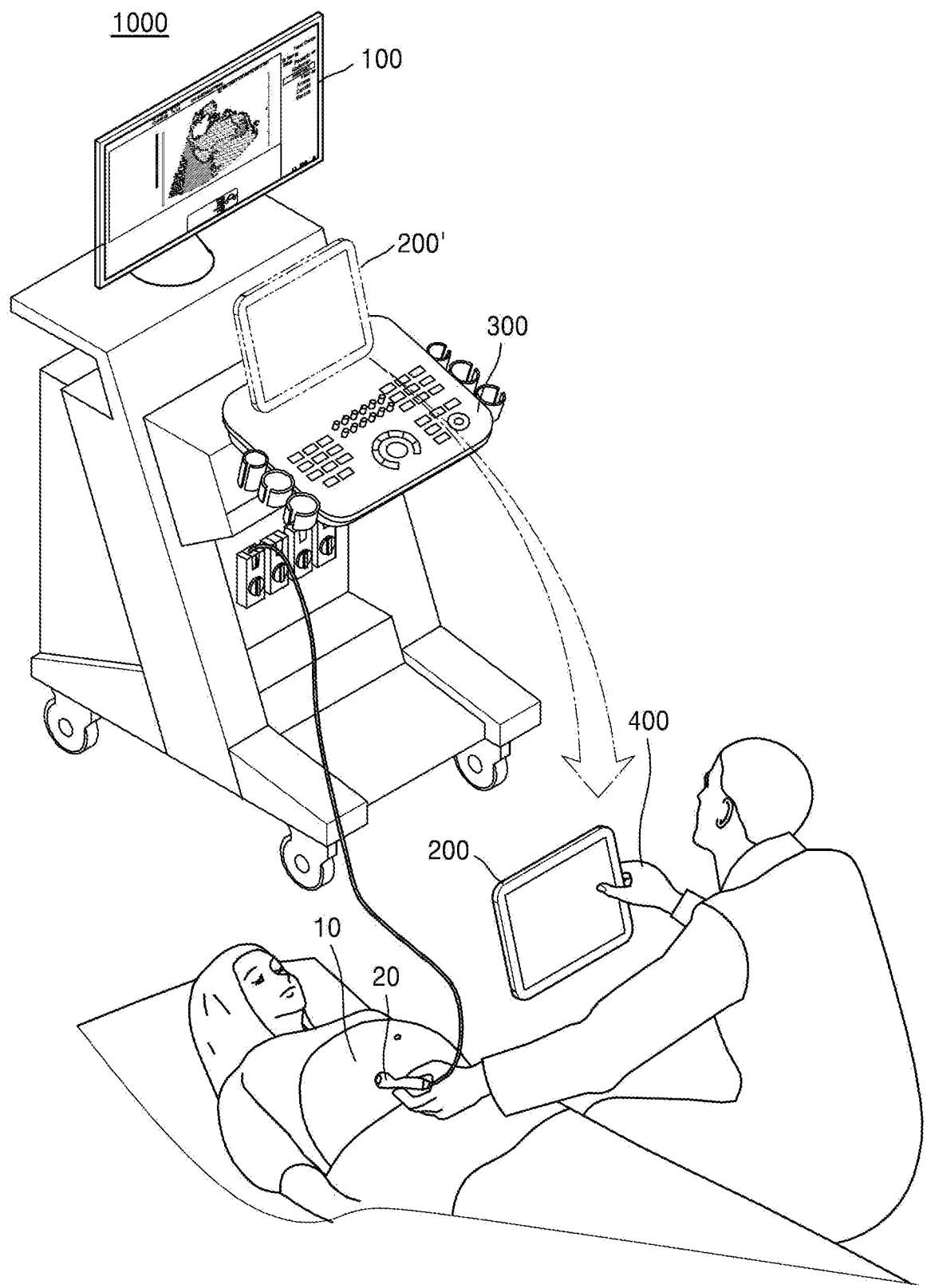
FIG. 2B is a diagram of an ultrasound apparatus including a detachable display unit, according to an exemplary embodiment.

FIG. 2B is a diagram of the ultrasound apparatus 1000 including a display unit that is detachable, according to an exemplary embodiment.

Referring to FIG. 2B, the ultrasound apparatus 1000 may include the first display unit 100, the second display unit 200, and a holder 200' for attaching/detaching the second display unit 200 to/from the ultrasound apparatus 1000.

According to the exemplary embodiment, the first display unit 100 may be directly connected to the body of the ultrasound apparatus 1000, and may display ultrasound images during performing the ultrasound diagnosis. The first display unit 100 of FIG. 2B corresponds to the first display unit 100 of FIG. 1, and thus, detailed descriptions thereof are omitted.

The second display unit 200 may be attached to the ultrasound apparatus 1000 via the holder 200', or may be detached from the ultrasound apparatus 1000. According to the exemplary embodiment, the ultrasound apparatus 1000 may include a sensor for sensing whether the second display unit 200 is attached to or detached from the ultrasound apparatus 1000. For example, a sensor or an interface for sensing whether the second display unit 200 is attached to or detached from the ultrasound apparatus 1000 may be formed at an inner or outer portion of the holder 200'.

According to the exemplary embodiment, if the second display unit 200 is detached from the ultrasound apparatus 1000, the second display unit 200 may communicate with the ultrasound apparatus 1000 via a short-range communication. Here, the short-range communication may include at least one selected from wireless fidelity (Wi-Fi), Bluetooth, Zigbee, Wi-Fi direct (WFD), ultra wideband (UWB), infrared data association (IrDA), Bluetooth low energy (BLE), and near field communication (NFC), but is not limited thereto.

For example, the second display unit 200 senses a location of a pointer 400 (e.g., a finger) touching the second display unit 200, and transmits information about the location of the pointer 400 to a communicator of the ultrasound apparatus 1000. Here, the ultrasound apparatus 1000 may select at least one control item corresponding to the location of the pointer 400, from among the plurality of control items displayed on the second display unit 200. Otherwise, the second display unit 200 may transmit information about the control item corresponding to the location of the pointer 400 to the communicator of the ultrasound apparatus 1000.

According to the exemplary embodiment, the ultrasound apparatus 1000 may display some or all of the control items displayed on the second display unit 200 on the first display unit, based on the location of the pointer 400 touching the second display unit 200. In this case, the user may identify the at least one control item corresponding to the location of the pointer 400 (e.g., finger) on the second display unit 200 through the first display unit 100, without directly seeing the second display unit 200 that is detached from the ultrasound apparatus 1000.

The user may select a certain item from among the control items displayed on the second display unit 200 while seeing the first display unit 100, not the second display unit 200 that is detached from the ultrasound apparatus 1000. In this case, since the gaze of the user may be fixed at the first display unit 100 displaying the ultrasound images, the user may concentrate on the ultrasound images.

Figure 3:
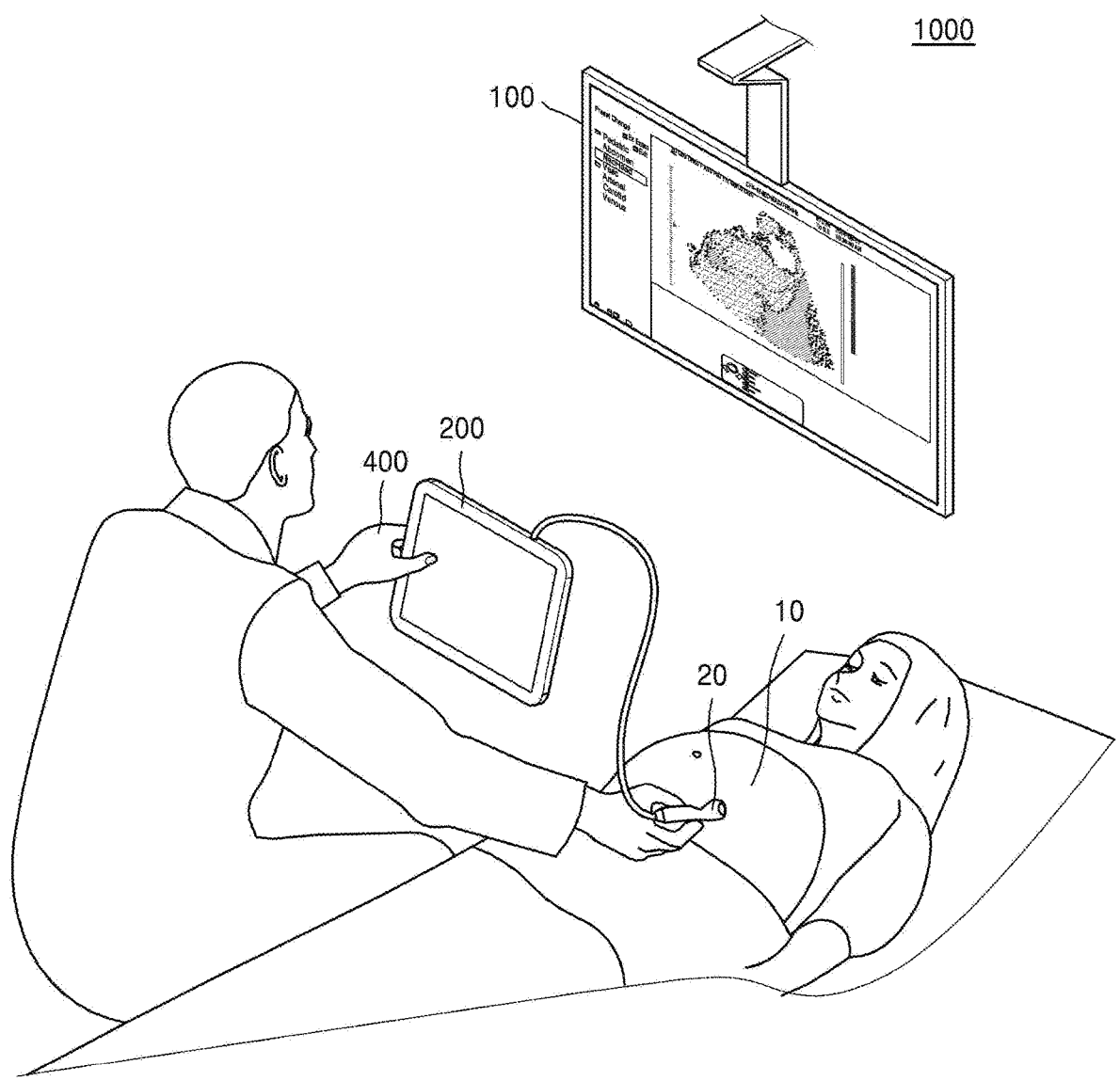
FIG. 3 is a diagram of a portable ultrasound apparatus according to an exemplary embodiment.

FIG. 3 is a diagram of a portable ultrasound apparatus 1000 according to an exemplary embodiment.

As shown in FIG. 3, the ultrasound apparatus 1000 according to the present exemplary embodiment may be portable. Here, the ultrasound apparatus 1000 may include the second display unit 200 of a touch screen type, and a probe 20. The ultrasound apparatus 1000 may further include a communicator for communicating with the first display unit 100 on the outside. In this case, the communicator of the ultrasound apparatus 1000 may directly transmit information to the first display unit 100 via the short-range communication.

In addition, the ultrasound apparatus 1000 may transmit information to the first display unit 100 via a server. For example, the communicator of the ultrasound apparatus 1000 may exchange data with the first display unit 200 connected to the ultrasound apparatus 1000 via a picture archiving and communication system (PACS). The communicator of the ultrasound apparatus 1000 may perform data communication according to digital imaging and communications in medicine (DICOM).

According to the exemplary embodiment, the ultrasound apparatus 1000 may display ultrasound images obtained via the probe 20 on the second display unit 200. In addition, the ultrasound apparatus 1000 may transmit the ultrasound images obtained via the probe 20 to the first display unit 100. Here, the first display unit 100 may display the ultrasound images of the object 10 in real-time.

In addition, according to the exemplary embodiment, the ultrasound apparatus 1000 may transmit information about the at least one control item selected based on the location of the pointer 400 touching the second display unit 200 to the first display unit 100. Here, the first display unit 100 may display information about the at least one control item together with the ultrasound images of the object 10. In this case, the user may select the at least one control item (e.g., a functional key) displayed on the second display unit 200 while fixing the eyes on the first display unit 100 displaying the ultrasound images at the outside.

For example, the user may perform an ultrasound image scanning operation without moving his/her eyes, while keeping his/her eyes on the main screen (i.e., the first display unit 100), holding the probe 20 with his/her right hand, and holding the touch screen (i.e., the second display unit 200) displaying the control items with his/her left hand. Hereinafter, a method for the ultrasound apparatus 1000 to provide information so as not to disperse the user's eyes (e.g., a sonographer's eyes) during scanning ultrasound images will be described in detail with reference to FIG. 4.

Figure 4:
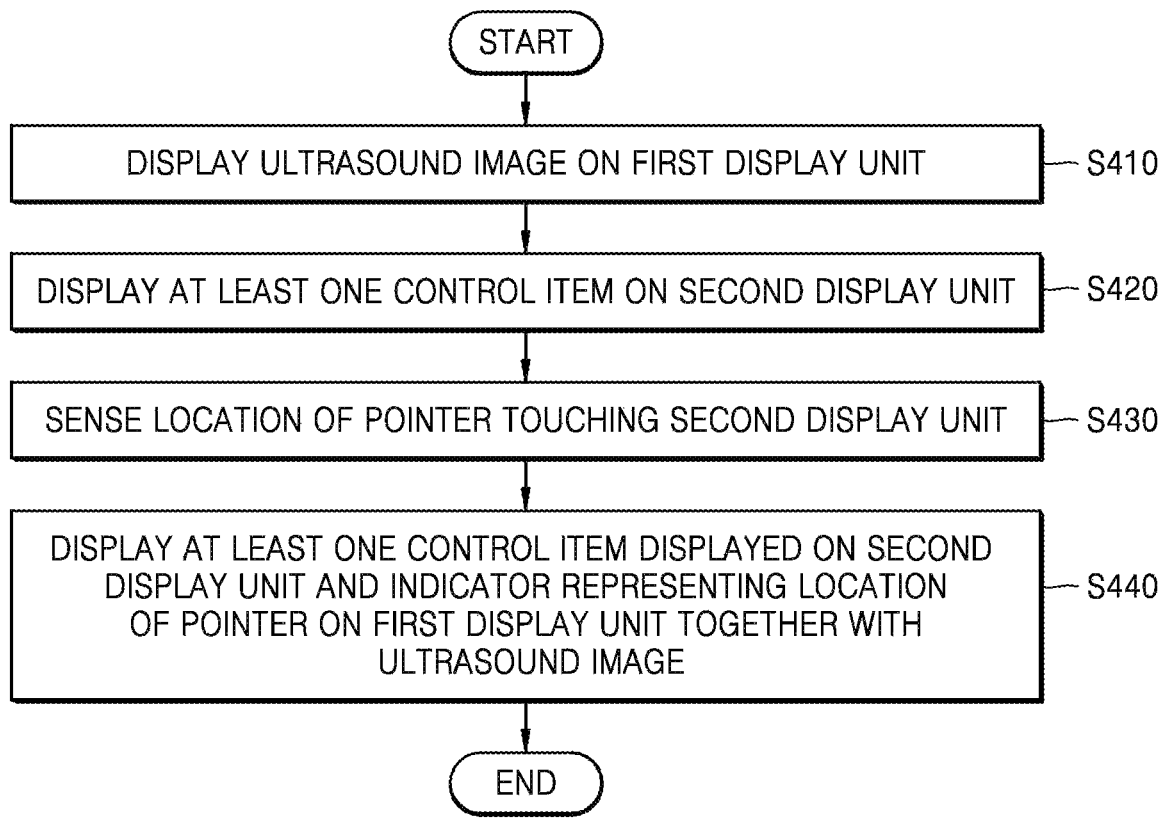
FIG. 4 is a flowchart illustrating a method of providing information of an ultrasound apparatus, according to an exemplary embodiment.

FIG. 4 is a flowchart illustrating a method of providing information in the ultrasound apparatus, according to an exemplary embodiment.

In operation S410, the ultrasound apparatus 1000 may display ultrasound images on the first display unit 100.

The ultrasound images displayed on the first display unit 100 may be displayed variously. For example, the ultrasound image may be at least one of a brightness mode (B mode) image representing a magnitude of an ultrasound echo signal reflected by an object as brightness, a color mode (C mode) image representing a velocity of a moving object as a color by using a Doppler effect, a Doppler mode (D mode) image representing an object of a moving object as a spectrum by using a Doppler effect, a motion mode (M mode) image representing movement of an object at a constant location according to time, and an elastic mode image representing a difference between reactions when a compression is applied and not applied to an object as an image; however, the present invention is not limited thereto. According to the exemplary embodiment, the ultrasound image may be a two-dimensional (2D) image, a three-dimensional (3D) image, or a four-dimensional (4D) image.

According to the exemplary embodiment, the ultrasound apparatus 1000 may display ultrasound images on the first display unit 100 in real-time based on ultrasound image data acquired from the object 10. For example, the ultrasound apparatus 1000 may transmit an ultrasound signal (beam) to the object 10 via the probe 20, and may generate an ultrasound image based on the ultrasound echo signal reflected from the object 10. In addition, the ultrasound apparatus 1000 may display the generated ultrasound image on the first display unit 100.

According to an exemplary embodiment, the ultrasound apparatus 1000 may display an ultrasound images stored in a storage medium in advance on the first display unit 100. For example, the ultrasound apparatus 1000 may read a certain ultrasound image from the storage medium, and may display the read ultrasound image on the first display unit 100.

Here, the storage medium may be a memory existing in the ultrasound apparatus 1000, or an external storage apparatus existing at the outside of the ultrasound apparatus 1000 (e.g., a universal serial bus (USB), a wearable device, and a cloud server). Otherwise, the storage medium may be a cache memory.

In operation S420, the ultrasound apparatus 1000 may display at least one control items on the second display unit 200. The at least one control items may be a user-selectable item. For example, the control item may include a menu, an adjustment button, a mode selection button, a shortcut icon, an adjustment interface for adjusting a parameter value, a functional key, a setting window, etc., but is not limited thereto.

According to the exemplary embodiment, the at least one control item displayed on the second display unit 200 may be related to the ultrasound image. For example, the at least one control item may be an item for adjusting a parameter value regarding the ultrasound image data (or ultrasound echo signal), and may include a time gain compensation (TGC)/lateral gain compensation (LGC) setting window, 2D/3D/4D buttons, a gain button, a focus button, a depth button, a zoom button, a dynamic range button, a gray map button, a chroma map button, a low MI button, a reject level button, etc.

According to the exemplary embodiment, the ultrasound apparatus 1000 may display control items on an entire area of the second display unit 200. Otherwise, the ultrasound apparatus 1000 may display the control items on a partial region of the second display unit 200. For example, the ultrasound apparatus 1000 may display the ultrasound image of the object 10 on a first region of the second display unit 200, and may display the control items related to the ultrasound image on a second region of the second display unit 200.

In operation S430, the ultrasound apparatus 1000 may sense a location of the pointer 400 touching the second display unit 200. Here, the pointer 400 may be a finger of the user or an external device such as an electronic pen.

In addition, according to the exemplary embodiment, the ultrasound apparatus 1000 may sense the location of the pointer 400 contacting the second display unit 200, or may sense a location of the pointer 400 hovering within a predetermined distance from the second display unit 200 without contacting the second display unit 200.

According to the exemplary embodiment, the ultrasound apparatus 1000 may sense the location of the pointer 400 in various manners. For example, the ultrasound apparatus 1000 may sense the location of the pointer 400 on the second display unit 200 by using an internal sensor (e.g., a sensor detecting variation in a capacitance, a pressure sensor, an infrared ray sensor, a temperature sensor, a proximity sensor, an image sensor, etc.). Alternatively, the ultrasound apparatus 1000 may sense the location of the pointer 400 on the second display unit by using an external device such as a camera (e.g., a general camera, an infrared ray camera, a depth camera, a closed circuit television (CCTV) camera, etc.).

The method for the ultrasound apparatus 1000 to sense the location of the pointer 400 will be described in more detail later with reference to FIGS. 5 to 8.

In operation S440, the ultrasound apparatus 1000 may display the at least one control item displayed on the second display unit 200 and an indicator that indicates the location of the pointer 400, on the first display unit 100 together with the ultrasound images.

According to the exemplary embodiment, the ultrasound apparatus 1000 may display the at least one control item displayed on the second display unit 200 and the indicator that indicates the location of the pointer 400, on the first display unit 100 to overlap with the ultrasound image. For example, the ultrasound apparatus 1000 may display the at least one control item and the indicator on the ultrasound image displayed on the first display unit 100.

According to the exemplary embodiment, the ultrasound apparatus 1000 may display the at least one control item displayed on the second display unit 200 and the indicator that indicates the location of the pointer 400 on the first display unit 100 so as not to overlap with the ultrasound image. For example, the ultrasound apparatus 1000 may display the ultrasound image on the first region of the first display unit 100, and may display at least one menu item and the indicator on the second region of the first display unit 100. Here, the first region and the second region may be different from each other.

According to the exemplary embodiment, the indicator that indicates the location of the pointer 400 may be realized as a predefined shape, a predefined line, a predefined color, or a predefined shade, but is not limited thereto. For example, the ultrasound apparatus 1000 may represent the indicator that indicates the location of the pointer 400 touching the second display unit 200 as an arrow or a circle on the first display unit 100. Otherwise, the ultrasound apparatus 1000 may represent the indicator that indicates the location of the pointer 400 in a red color or a yellow color on the first display unit 100.

According to the exemplary embodiment, the ultrasound apparatus 1000 may represent the indicator that indicates the location of the pointer 400 on the at least one control item displayed on the first display unit 100. For example, the ultrasound apparatus 1000 may select a first control item corresponding to the location of the pointer 400, from among the at least one control item displayed on the second display unit 200. The ultrasound apparatus 1000 may locate the indicator on the first control item from among the at least one control item displayed on the first display unit 100. For example, the ultrasound apparatus 1000 may mark a contour line around the first control item as the indicator. Otherwise, the ultrasound apparatus 1000 may represent the first control item in a certain color (e.g., red), or represent the indicator as slashes on the first control item.

According to the exemplary embodiment, the ultrasound apparatus 1000 may display at least one control item in consideration of a size of the first display unit 100. For example, if the first display unit 100 is twice as large as the second display unit 200, the ultrasound apparatus 1000 may increase the control items displayed on the second display unit 200 by twice to be displayed on the first display unit 100.

According to the exemplary embodiment, the ultrasound apparatus 1000 may display at least one control item on the first display unit 100 based on a ratio of a region displaying the control item with respect to an entire region of the second display unit 200. For example, if the at least one control item is displayed on half the entire region of the second display unit 200, the ultrasound apparatus 1000 may display the at least one control item on a region corresponding to ½ of the entire region of the first display unit 100.

According to the exemplary embodiment, the ultrasound apparatus 1000 may determine a location of displaying the control item on the first display unit 100, based on the location of the control item displayed on the second display unit 200. For example, if the control item is displayed on an upper left portion of the second display unit 200, the ultrasound apparatus 1000 may display the control item on an upper left portion of the first display unit 100.

According to the exemplary embodiment, the ultrasound apparatus 1000 may display the control item on the first display unit 100 according to a layout of the control item displayed on the second display unit 200. Alternatively, the ultrasound apparatus 1000 may display the control item on the first display unit 100 in a different layout from the layout of the control item on the second display unit 200.

According to the exemplary embodiment, the ultrasound apparatus 1000 may change a location of the indicator displayed on the first display unit 100 according to a change in the location of the pointer 400 touching the second display unit 200. For example, if the pointer 400 touching the second display unit 200 moves to a left side, the indicator displayed on the first display unit 100 may also move to a left side.

In addition, the ultrasound apparatus 1000 may only display the ultrasound images on the first display unit 100 during a normal operation, and may additionally display the at least one control item displayed on the second display unit 200 and the indicator that indicates the location of the pointer 400 touching the second display unit 200, on the first display unit 100 when a certain event occurs.

Hereinafter, a time point of displaying the at least one control item on the first display unit 100 will be described below with reference to FIGS. 5 to 8.

Figure 5:
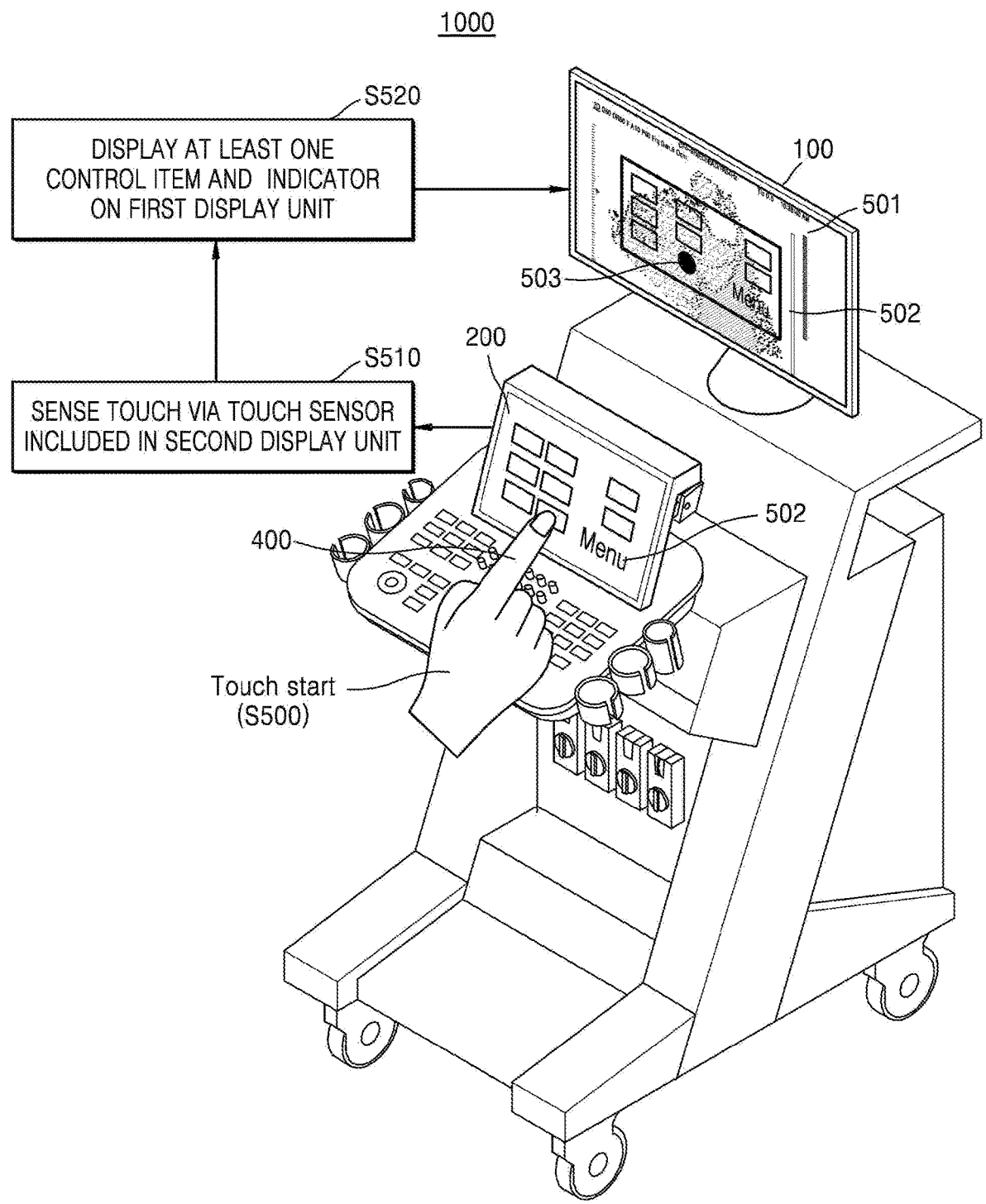
FIG. 5 is a diagram illustrating an operation of an ultrasound apparatus for indicating at least one control item and an indicator on a main screen in a case where a touch event with respect to a touch screen occurs, according to an exemplary embodiment.

FIG. 5 is a diagram illustrating an operation of the ultrasound apparatus 1000 for displaying at least one control item and an indicator on the main screen, when a touch event to the touch screen occurs. In FIG. 5, an example where the first display unit 100 is the main screen, the second display unit 200 is the touch screen, and the pointer 400 is a finger 500 is illustrated.

In operations S500 and S510, the ultrasound apparatus 1000 may sense a touch of the finger 500 via a touch sensor included in the second display unit 200. For example, the touch sensor (e.g., a sensor detecting variation in a capacitance and a pressure sensor) included in the second display unit 200 may recognize a location of the second display unit 200, where the finger 500 touches. In this case, the second display unit 200 may notify a controller of the ultrasound apparatus 1000 that a touch event has occurred. Otherwise, the second display unit 200 may transmit information about the touched location (e.g., coorindate information and information about a control item displayed on the touched location) to the controller.

In operation S520, the ultrasound apparatus 1000 may display the at least one control item and the indicator on the first display unit 100 when the touch event occurs. For example, the ultrasound apparatus 1000 may display a plurality of menu items 502 displayed on the second display unit 200 and an indicator 503 representing the location of the finger 500 over the ultrasound image 501 displayed on the first display unit 100. Here, since the finger 500 is located on a menu of a third row and second column in the second display unit 200, a red circle may be represented on a menu of a third row and a second column in the first display unit 100 as the indicator 503 representing the location of the finger 500.

The plurality of menu items 502 and the indicator 503 displayed on the first display unit 100 may be semi-transparent. In addition, if the user moves his/her finger 500 on the second display unit 200 (e.g., a drag gesture), the ultrasound apparatus 1000 may also move the location of the indicator 503.

In addition, when the touch event has finished on a first item from among the plurality of menu items 502 (e.g., the user removes his/her finger 500 from the first item displayed on the second display unit 200), the ultrasound apparatus 1000 may perform a function regarding the first item. Otherwise, the ultrasound apparatus 1000 may display a GUI related to the first item on the first display unit 100 and/or the second display unit 200.

According to the exemplary embodiment, if the touch event has finished on an empty portion where the plurality of menu items 502 are not displayed, the plurality of menu items 502 and the indicator 503 that have been displaying on the first display unit 100 are removed so that the first display unit 100 may only display the ultrasound images.

Therefore, when the user touches the second display unit 200, the user may identify and manipulate the plurality of menu items 502 on the second display unit 200, with the ultrasound image 501 of the object through the first display unit 100 without turning his/her head to the second display unit 200.

According to the exemplary embodiment, the ultrasound apparatus 1000 may sense that the user is scanning the ultrasound image of the object 10 via the probe 20 or a sensor included in the probe 20. In addition, when a touch onto the second display unit 200 is sensed while the user is scanning the ultrasound image of the object 10, the ultrasound apparatus 1000 may display the plurality of menu items 502 or some of the menu items 502 displayed on the second display unit 200, on the first display unit 100 with the ultrasound image.

Figure 6:
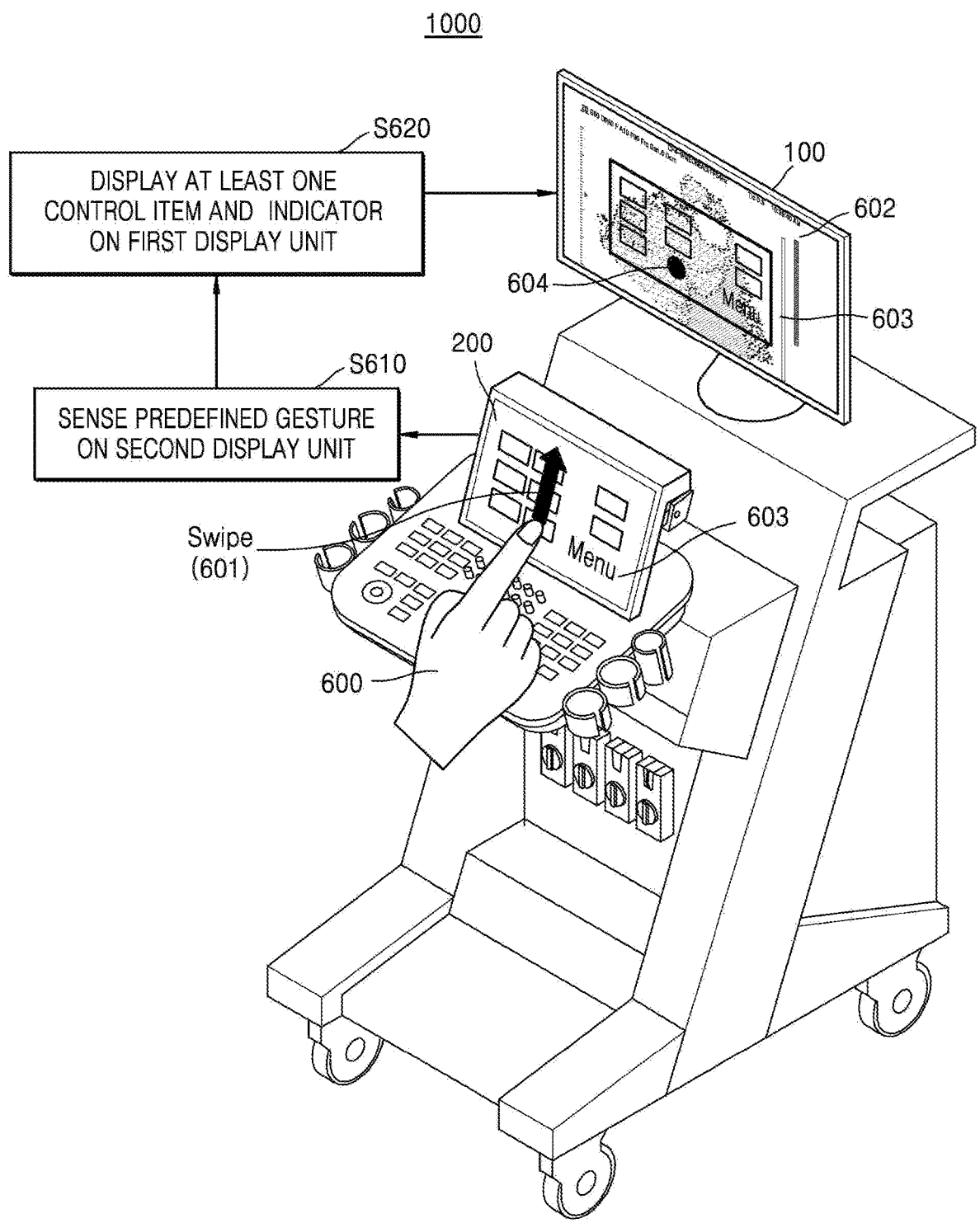
FIG. 6 is a diagram illustrating an operation of an ultrasound apparatus for displaying at least one control item and an indicator on a main screen according to predefined gestures, according to an exemplary embodiment.

FIG. 6 is a diagram illustrating an operation of the ultrasound apparatus 1000 for displaying at least one control item and an indicator on a main screen according to a predefined gesture. In FIG. 6, an example in which the first display unit 100 is a main screen, the second display unit 200 is a touch screen, and the pointer 400 is a finger 600 is shown.

In operation S610, the ultrasound apparatus 1000 may sense a predefined gesture on the second display unit 200. The predefined gesture may be gesture for directing the at least one control item that has been displayed to be displayed on the second display nit 200, on the first display unit 100. For example, the ultrasound apparatus 1000 may receive a swipe gesture 601, that is, swiping upward the finger 600 on the second display unit 200, from the user.

In operation S620, the ultrasound apparatus 1000 may display at least one control item and an indicator on the first display unit 100 on receiving the predefined gesture. For example, the ultrasound apparatus 1000 may display a plurality of menu items 603 displayed on the second display unit 200 and an indicator 604 indicating the location of the finger 600, on the ultrasound image 602 that is currently displayed on the first display unit 100, on receiving the swipe gesture 601 on the second display unit 200.

In addition, the plurality of menu items 603 and the indicator 604 displayed on the first display unit 100 may be semi transparent. In addition, when the user moves his/her finger 600 on the plurality of menu items 603 displayed on the second display unit 200 (e.g., a drag gesture), the ultrasound apparatus 1000 may move the indicator 604 according to the touch location of the finger 600.

According to the exemplary embodiment, the user may select one of the plurality of menu items 603. For example, the user may drag his/her finger 600 on the plurality of menu items 603, and then, may double tap the second display unit 200 when the indicator 604 is located at the first item. In this case, the ultrasound apparatus 1000 may sense a double-tap gesture on the first item, and may perform a function corresponding to the first item.

Otherwise, the user may drag his/her finger 600 on the plurality of menu items 603, and may place his/her middle finger on the second display unit 200 when the indicator 604 is located at the first item. Here, the ultrasound apparatus 1000 may sense a multi-finger gesture on the first item, and may perform a function corresponding to the first item.

In FIG. 6, although the swipe gesture is provided as an example of the predefined gesture, but the predefined gesture is not limited to the swipe gesture. For example, the predefined gesture may include a gesture of touching and holding a certain location, a gesture of selecting a certain hardware button, a multi-finger gesture (e.g., gather five fingers together on the touch screen), etc., but is not limited thereto.

Figure 7:
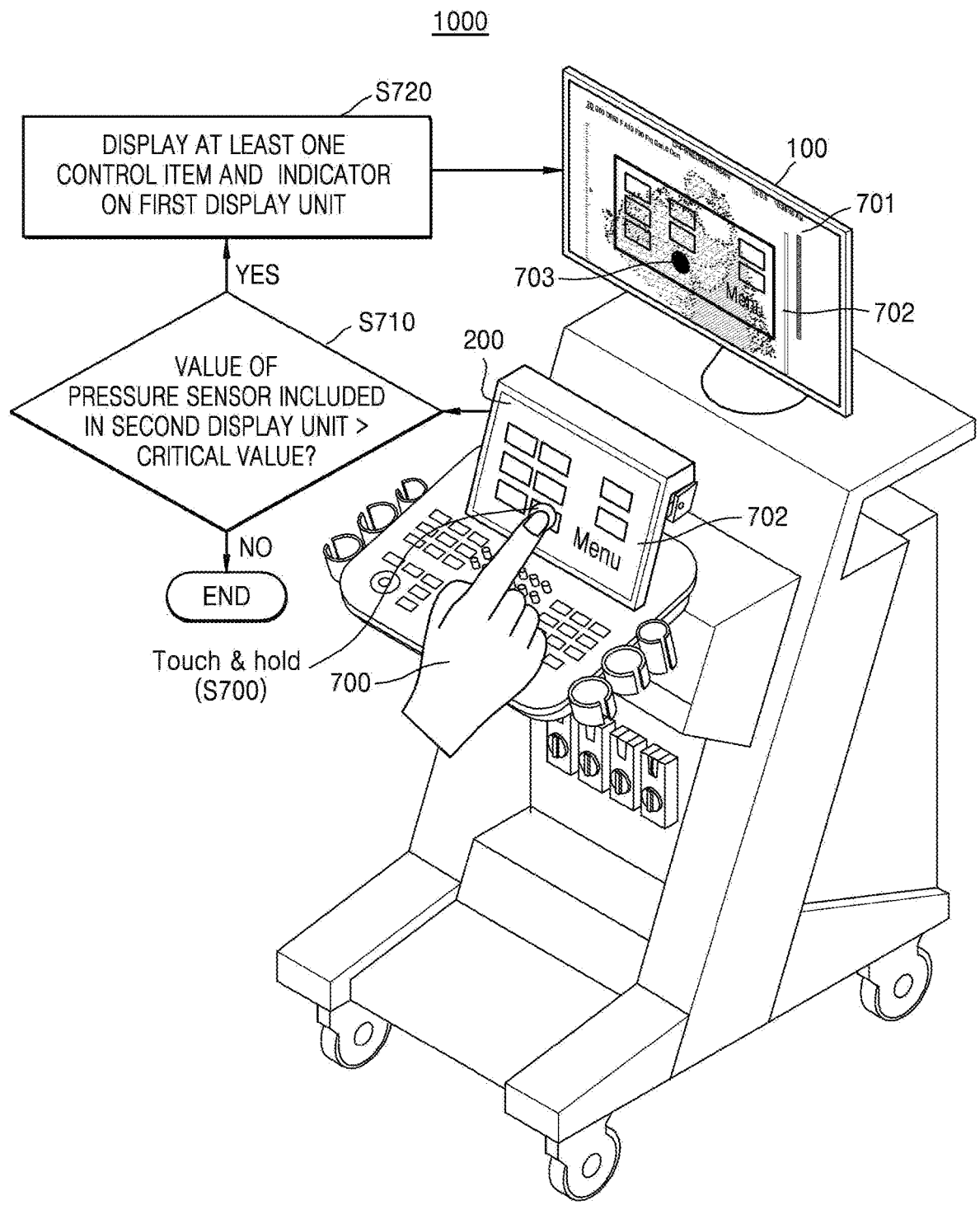
FIG. 7 is a diagram illustrating an operation of an ultrasound apparatus for sensing a pressure of touching a touch screen by using a pressure sensor, according to an exemplary embodiment.

FIG. 7 is a diagram illustrating an operation of the ultrasound apparatus 1000 for sensing a pressure touching the touch screen by using a pressure sensor. In FIG. 7, an example in which the first display unit 100 is a main screen displaying the ultrasound image, the second display unit 200 is a screen displaying menu items, and the pointer 400 is a finger 700 is illustrated.

In operation S700, the ultrasound apparatus 1000 may sense a touch and hold gesture on the second display unit 200. Here, the ultrasound apparatus 1000 may measure a pressure of the finger 700 touching the second display unit 200 by using a pressure sensor included in the second display unit 200.

In operation S710, the ultrasound apparatus 1000 may determine whether a value measured by the pressure sensor included in the second display unit 200 is greater than a critical value. For example, the ultrasound apparatus 1000 may determine whether the finger 700 is pushing the second display unit 200 with a pressure that is equal to or greater than the critical value.

In operation S720, when the value measured by the pressure sensor included in the second display unit 200 is greater than the critical value, the ultrasound apparatus 1000 may display at least one control item and an indicator on the first display unit 100. For example, the ultrasound apparatus 1000 may display a plurality of menu items 702 displayed on the second display unit 200 and an indicator 703 that indicates a location of the finger 700, on an ultrasound image 701 that is currently displayed on the first display unit 100.

Here, when the user moves his/her finger 700 on the plurality of menu items 702 displayed on the second display unit 200 (e.g., a drag gesture), the ultrasound apparatus 1000 may move the indicator 703 according to the location of the finger 700.

According to the exemplary embodiment, the user may select one of the plurality of menu items 702. For example, the user may drag his/her finger 700 on the plurality of menu items 702 and double taps the second display unit 200 when the indicator 703 is located at a first item. In this case, the ultrasound apparatus 1000 may sense the double-tap gesture on the first item, and may perform a function corresponding to the first item.

Figure 8:
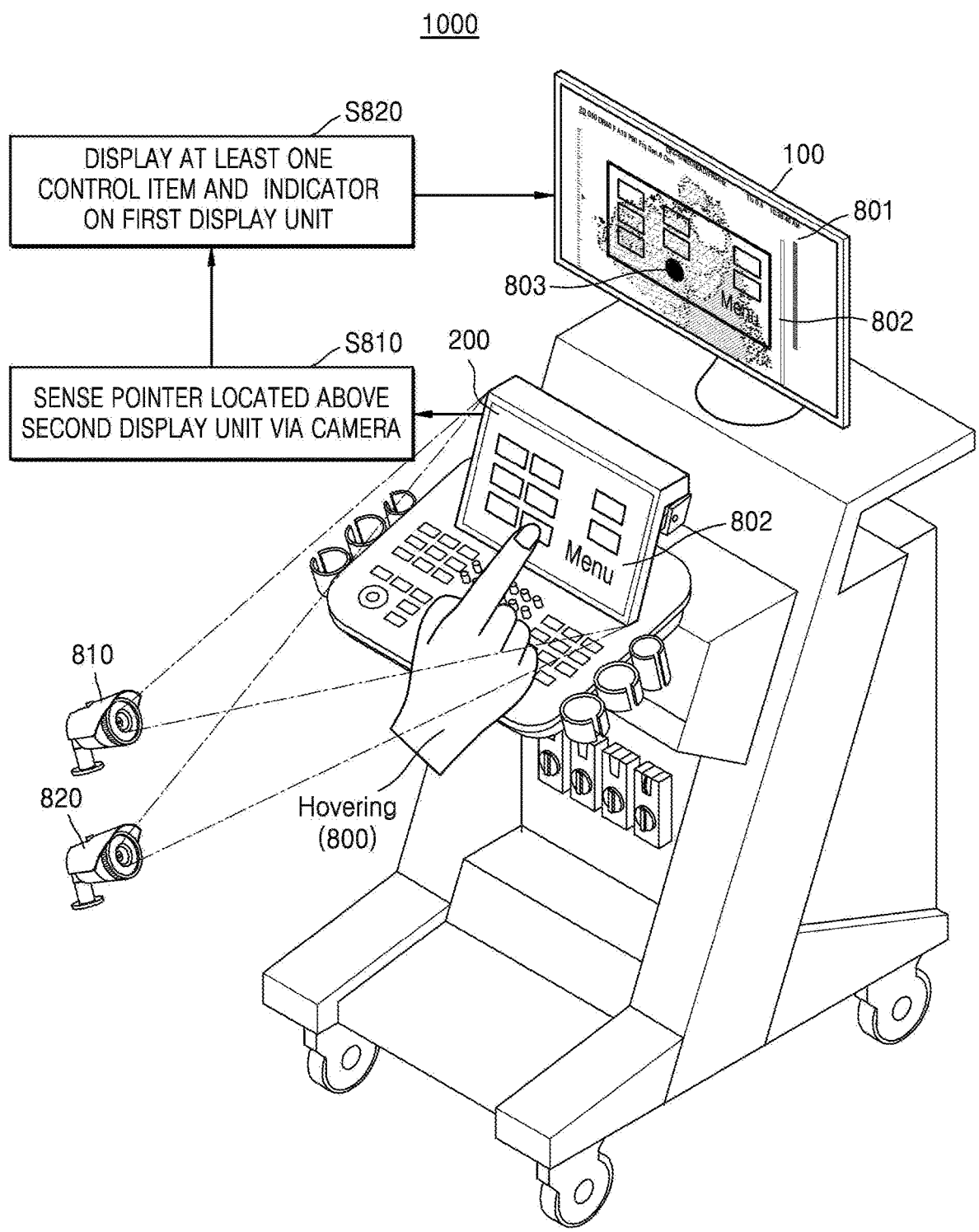
FIG. 8 is a diagram illustrating an operation of an ultrasound apparatus for sensing an approximate touch gesture of a user by using a camera, according to an exemplary embodiment.

FIG. 8 is a diagram illustrating an operation of the ultrasound apparatus 1000 for sensing a proximity touch gesture of the user by using a camera.

In operation S810, the ultrasound apparatus 1000 may sense the pointer 400 located above the second display unit 200 via the camera. For example, the ultrasound apparatus 1000 may sense a hovering gesture 800 of the user via the camera.

In the present specification, the hovering gesture may denote an input event, in which the pointer 400 (e.g., a finger or an electronic pen) approaches the second display unit 200 within a predefined distance. For example, the hovering gesture may denote an event, in which the pointer 400 approaches the second display unit 200 to a distance at which the ultrasound apparatus 1000 may detect a location of the pointer 400 (e.g., a finger).

According to the exemplary embodiment, the ultrasound apparatus 1000 may sense the pointer 400 above the second display unit 200 via a plurality of cameras or via one camera. In addition, the ultrasound apparatus 1000 may sense the pointer 400 above the second display unit 200 via the camera attached therein or the camera located on outside of the ultrasound apparatus 1000.

Here, the camera may include a general camera 810 (e.g., an image sensor), an infrared ray camera 820 (e.g., an infrared ray sensor), a depth camera (e.g., a depth sensor), and a CCTV, but is not limited thereto.

For example, the ultrasound apparatus 1000 may sense the pointer 400 located above the second display unit 200 by analyzing image data (a plurality of image frames) obtained via the general camera 810. Otherwise, the ultrasound apparatus 1000 may sense the pointer 400 located above the second display unit 200 by analyzing infrared image data obtained by the infrared camera 820. In particular, if the pointer 400 is a finger, since there is a large difference between temperatures of the second display unit 200 and the finger, the ultrasound apparatus 1000 may easily recognize the finger above the second display unit 200 via the infrared camera 820.

In addition, the ultrasound apparatus 1000 may sense the finger located above the second display unit 200 based on a difference between a first depth value from the depth camera to the second display unit 200 and a second depth value from the depth camera to the finger.

In operation S820, if the pointer 400 located above the second display unit 200 is sensed by the camera, the ultrasound apparatus 1000 may display at least one control item and an indicator on the first display unit 100. For example, the ultrasound apparatus 1000 may display a plurality of menu items 802 displayed on the second display unit 200 and an indicator 803 indicating a location of the finger, on an ultrasound image 801 currently displayed on the first display unit 100.

Here, if the user moves his/her finger within a predetermined separation distance from the second display unit 200 without contacting the second display unit 200 (e.g., a hovering gesture), the ultrasound apparatus 1000 may move the indicator 803 according to the location of the finger.

According to the exemplary embodiment, the user may select one of the plurality of menu items 802. For example, the user may hover his/her finger within a predetermined separation distance from the plurality of menu items 802 displayed on the second display unit 200, and then, may touch the second display unit 200 (or a first item on the second display unit 200) when the indicator 803 is located at the first item). In this case, the ultrasound apparatus 1000 senses the touch gesture of the user onto the first item by using the camera or the touch sensor, and performs a function corresponding to the first item.

Figure 9:
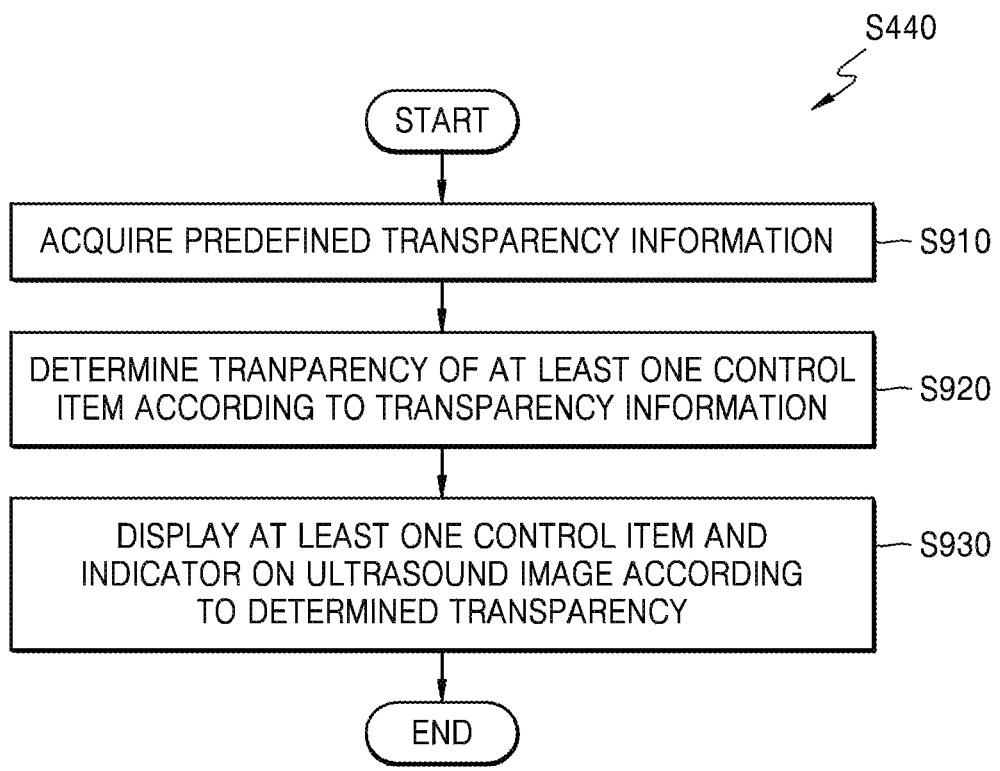
FIG. 9 is a flowchart illustrating a method for an ultrasound apparatus to determine transparency of at least one control item, according to an exemplary embodiment.

The plurality of menu items 802 on the ultrasound image 801 may be displayed to be semi transparent. Referring to FIG. 9, an operation of the ultrasound apparatus 1000 for displaying the at least one control item on the first display unit 100 based on predefined transparency information will be described below.

FIG. 9 is a flowchart illustrating a method for the ultrasound apparatus 1000 to determine transparency of at least one control item.

In operation S910, the ultrasound apparatus 1000 may acquire predefined transparency information. The transparency information may be information for defining a transparency of the at least one control item displayed on the second display unit 200. Here, the transparency may be defined by the user or the ultrasound apparatus 1000. In addition, the predefined transparency information may be changed according to a user input.

According to the exemplary embodiment, the predefined transparency information may include transparencies that are defined to be different with respect to the control items. For example, a first item to a tenth item may have a transparency of 20%, an eleventh item to a fifteenth item may have a transparent of 30%, and a sixteenth item to a twenty-second item may have a transparency of 35%.

According to the exemplary embodiment, the predefined transparency information may be read from a memory of the ultrasound apparatus 1000 or may be transmitted from outside.

In operation S920, the ultrasound apparatus 1000 may determine a transparency of at least one control item according to the predefined transparency information. For example, the ultrasound apparatus 1000 may determine the transparency with respect to the entire control items displayed on the second display unit 200 or with respect to some of the control items displayed on the second display unit 200, based on the predefined transparency information.

According to the exemplary embodiment, the predefined transparency information may include information about a transparency of an indicator that indicates the location of the pointer 400. In this case, the ultrasound apparatus 1000 may determine a transparency of the indicator according to the predefined transparency information.

In operation S930, the ultrasound apparatus 1000 may display at least one control item and the indicator indicating the location of the pointer 400 on the ultrasound image, according to the determined transparency. For example, if the determined transparency is 30%, the ultrasound apparatus 1000 may display the at least one control item on the ultrasound image with the transparency of 30%.

According to the exemplary embodiment, the ultrasound apparatus 1000 may display the indicator indicating the location of the pointer 400 and the at least one control item with different transparencies from each other. For example, the ultrasound apparatus 1000 may display the indicator to be opaque and may display the at least one control item with the transparency of 30% on the first display unit 100. Alternately, the ultrasound apparatus 1000 may display the indicator with the transparency of 20% and display the at least one control item with the transparency of 50% on the first display unit 100.

In addition, according to the exemplary embodiment, the predefined transparency information may further include color information. Therefore, according to the exemplary embodiment, the ultrasound apparatus 1000 may determine color of the control items or color of the indicator. In addition, the ultrasound apparatus 1000 may display the control item or the indicator on the ultrasound image in the determined color.

Figure 10:
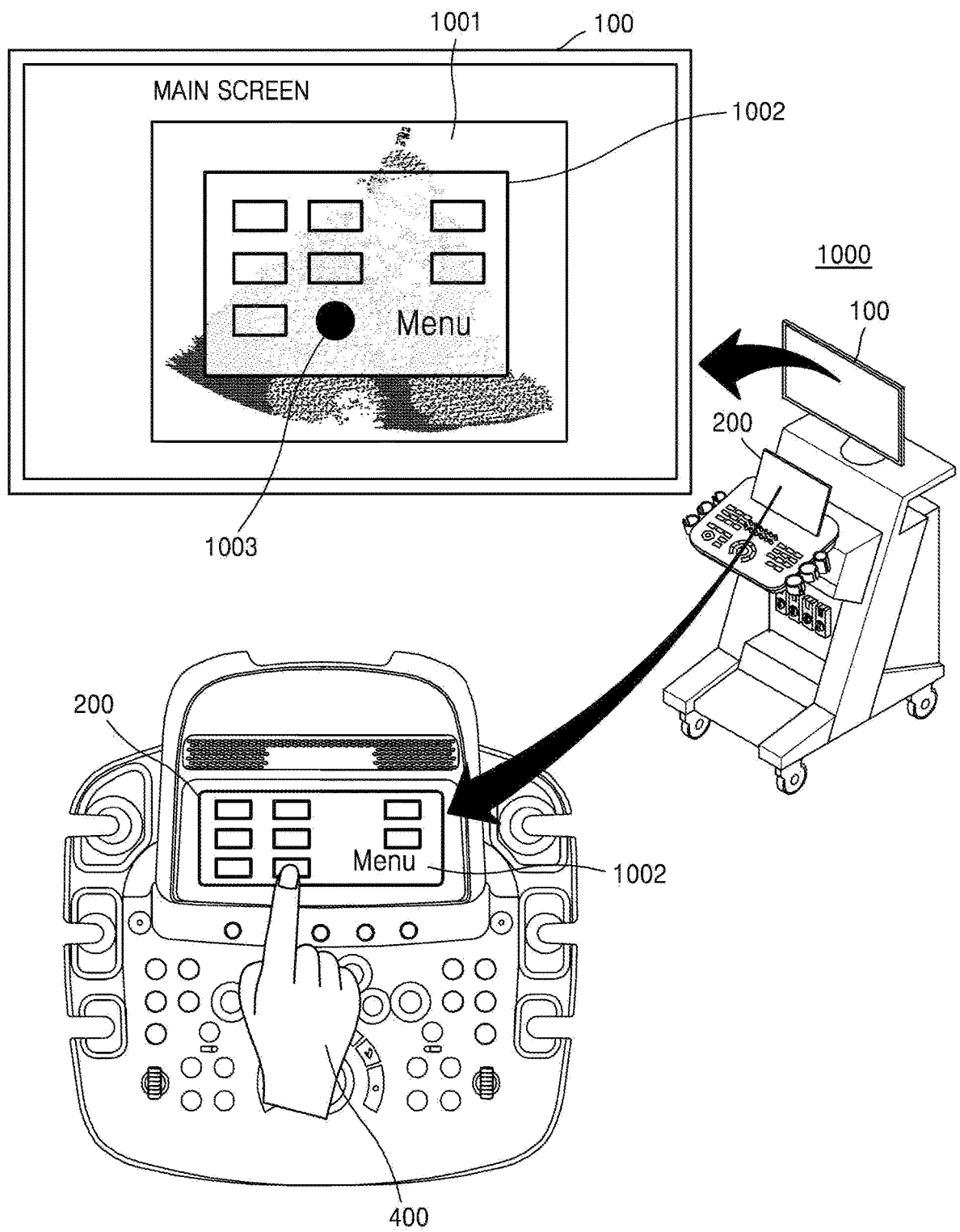
FIG. 10 is a diagram illustrating an example, in which an ultrasound apparatus displays at least one control item to be transparent on a main screen, according to an exemplary embodiment.

FIG. 10 is a diagram illustrating an example, in which the ultrasound apparatus 1000 display at least one control item on a main screen to be transparent. In FIG. 10, it is assumed that the first display unit 100 is the main screen and the second display unit 200 is a touch screen, as an example.

Referring to FIG. 10, the first display unit 100 may display an ultrasound image 1001 and the second display unit 200 may display a plurality of control items 1002. If the user touches the second display unit 200 by the pointer 400 (e.g., a finger), the ultrasound apparatus 1000 senses the touch event on the second display unit 200 and may display the plurality of control items 1002 displayed on the second display unit 200, on the ultrasound image 1001 of the first display unit 100. In addition, the ultrasound apparatus 1000 may display an indicator 1003 that indicates a location of the pointer 400 on the first display unit 100, with the plurality of control items 1002.

The ultrasound apparatus 1000 may adjust transparency of the plurality of control items 1002 so that the ultrasound image 1001 displayed on the first display unit 100 may not be blocked by the plurality of control items 1002. For example, the ultrasound apparatus 1000 may display the plurality of control items 1002 and the indicator 1003 with the transparency of 30%. In this case, the user may see the ultrasound image 1001, the plurality of control items 1002, and the indicator 1003 at the same time on the first display unit 100.

In addition, the ultrasound apparatus 1000 may receive an input for adjusting the transparency of the plurality of control items 1002 displayed on the first display unit 100 from 30% to 20%, from the user. In this case, the ultrasound apparatus 1000 may display the plurality of control items 1002 on the ultrasound image 1001 with the transparency of 20%.

According to the exemplary embodiment, the ultrasound apparatus 1000 may display the plurality of control items 1002 so as not to overlaid on the ultrasound image 1001. An operation of the ultrasound apparatus 1000 for displaying the plurality of control items 1002 not to overlay on the ultrasound image 1001 will be described below with reference to FIG. 11.

Figure 11:
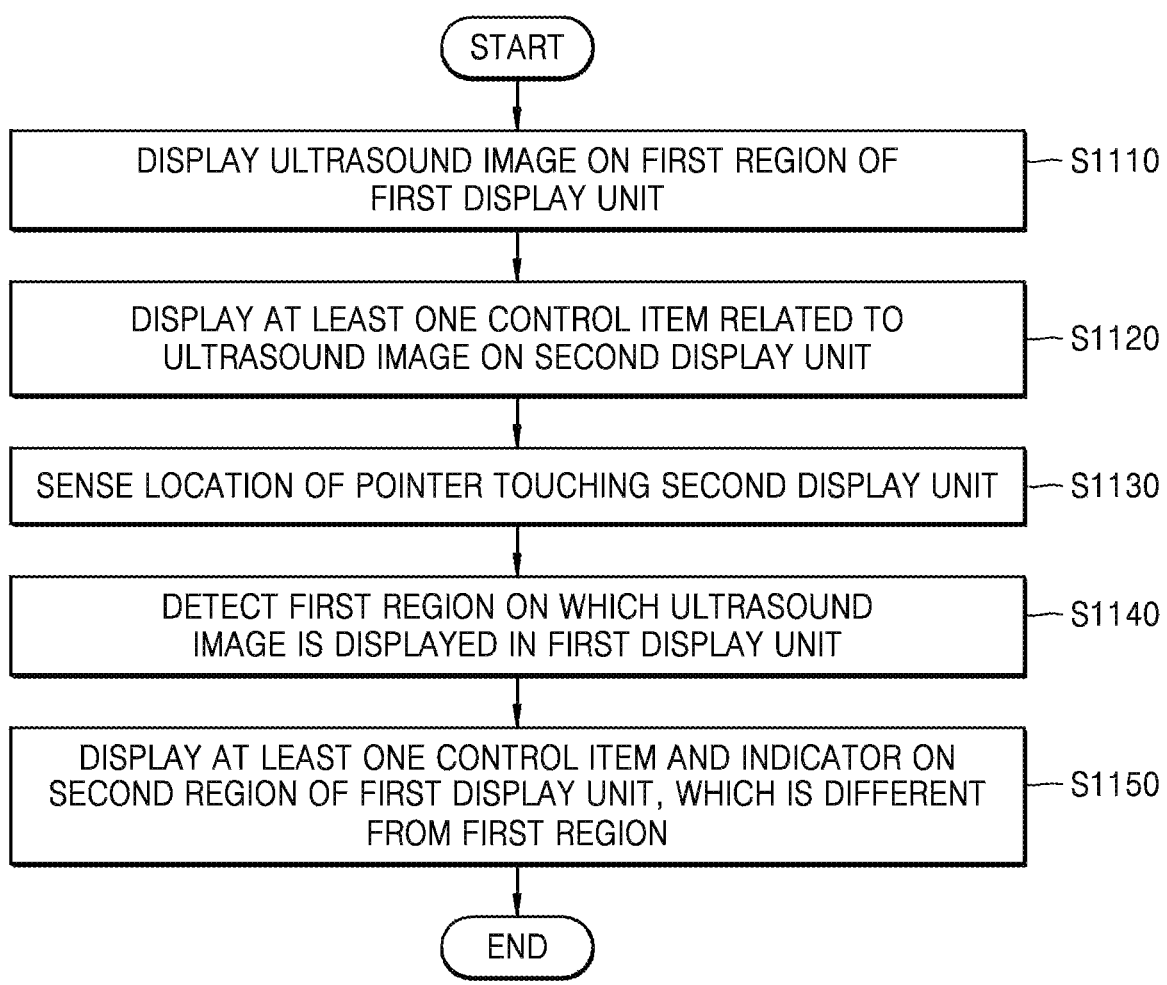
FIG. 11 is a flowchart illustrating a method for an ultrasound apparatus to display at least one control item and an indicator on a region where an ultrasound image is not displayed, according to an exemplary embodiment.

FIG. 11 is a flowchart illustrating a method for the ultrasound apparatus 1000 to display at least one control item and an indicator on a region where an ultrasound image is not displayed.

In operation S1110, the ultrasound apparatus 1000 may display an ultrasound image on a first region of the first display unit 100.

According to the exemplary embodiment, the ultrasound apparatus 1000 may display ultrasound images on the first region of the first display unit in real-time based on ultrasound image data obtained from the object 10. In addition, according to the exemplary embodiment, the ultrasound apparatus 1000 may display ultrasound images stored in advance in a storage medium, on the first region of the first display unit 100.

Here, the ultrasound image may be at least one of a B mode image, a C mode image, a D mode image, an M mode image, and an elastic mode image, but is not limited thereto. In addition, according to the exemplary embodiment, the ultrasound image may be a 2D image, a 3D image, or a 4D image.

In operation S1120, the ultrasound apparatus 1000 may display at least one control item related to the ultrasound image, on the second display unit 200.

The at least one control item may be a user-selectable item. For example, the control items may include a menu, an adjustment button, a mode selection button, a shortcut icon, an adjustment interface for adjusting a parameter value, a functional key, a setting window, etc., but is not limited thereto.

Operation S1120 corresponds to operation S420 of FIG. 4, and thus, detailed descriptions thereof are omitted.

In operation S1130, the ultrasound apparatus 1000 may sense a location of the pointer 400 touching the second display unit 200. Here, the pointer 400 may be a finger of the user or an external device such as an electronic pen.

According to the exemplary embodiment, the ultrasound apparatus 1000 may sense the location of the pointer 400 in various manners. For example, the ultrasound apparatus 1000 may sense the location of the pointer 400 on the second display unit by using an internal sensor (e.g., a sensor detecting variation in a capacitance, a pressure sensor, an infrared ray sensor, a temperature sensor, a proximity sensor, an image sensor, etc.). Alternatively, the ultrasound apparatus 1000 may sense the location of the pointer 400 on the second display unit 200 by using an external device such as a camera (e.g., a general camera, an infrared ray camera, a depth camera, a CCTV camera, etc.).

The method for the ultrasound apparatus 1000 to sense the location of the pointer 400 is described above with reference to FIGS. 5 to 8, and detailed descriptions thereof are omitted.

In operation S1140, the ultrasound apparatus 1000 may detect the first region on which the ultrasound image is displayed in the first display unit 100. For example, the ultrasound apparatus 1000 may detect the first region on which the ultrasound image is displayed based on rendering information of the first display unit 100.

In operation S1150, the ultrasound apparatus 1000 may display the at least one control item and the indicator that indicates the location of the pointer 400 on a second region that is different from the first region in the first display unit 100.

In this case, the ultrasound image is not hidden by the at least one control item and the indicator that indicates the location of the pointer 400.

Figure 12:
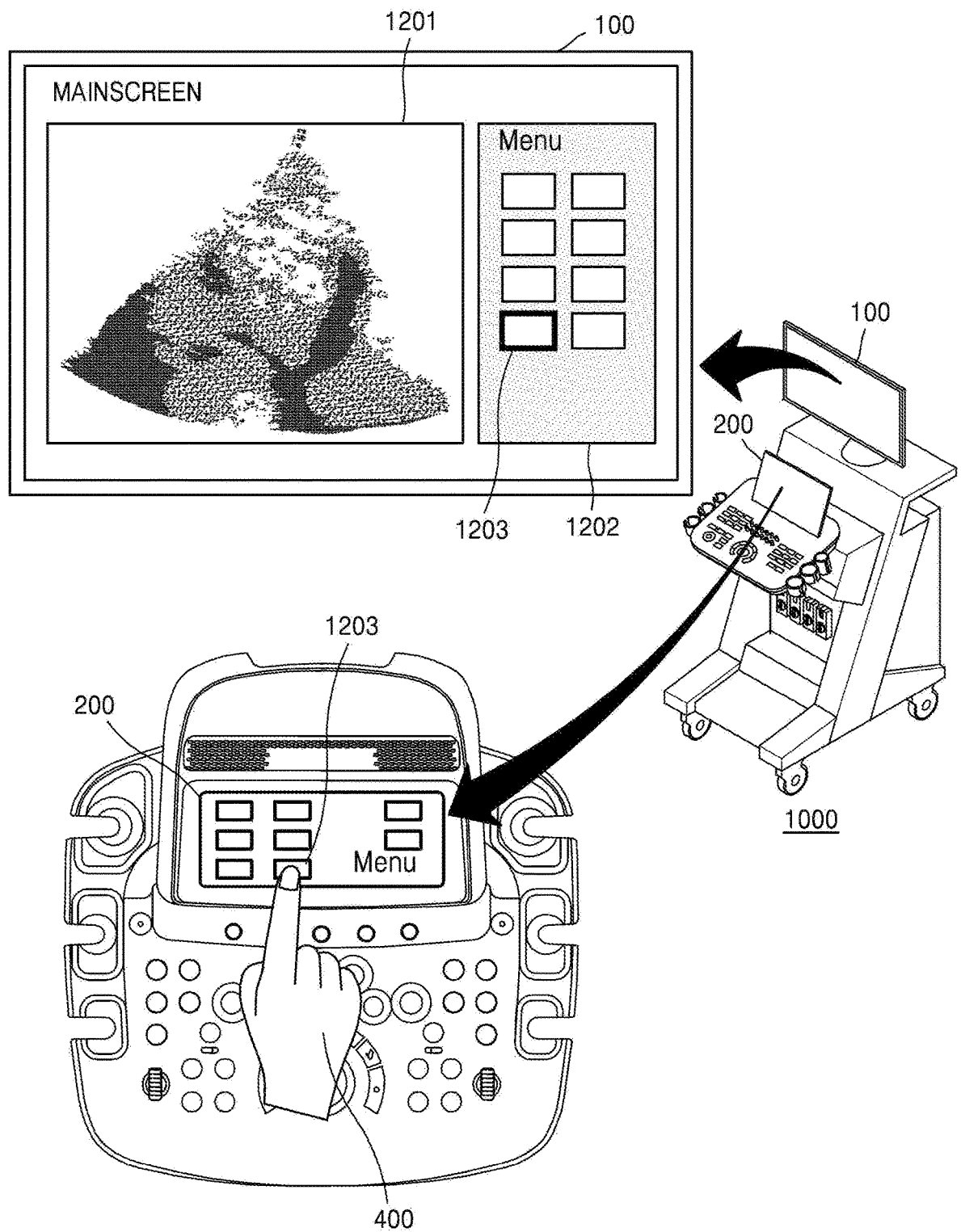
FIG. 12 is a diagram illustrating an example, in which an ultrasound apparatus displays an ultrasound image on a first region of a main screen and displays at least one control item and an indicator on a second region of the main screen, according to an exemplary embodiment.

Referring to FIG. 12, the example in which the ultrasound apparatus 1000 displays the plurality of control items so as not to overlay on the ultrasound image will be described below.

FIG. 12 is a diagram illustrating an example, in which the ultrasound apparatus 1000 displays the ultrasound image on a first region 1201 of the main screen and displays at least one control item and the indicator on a second region 1202 of the main screen. In FIG. 12, it is assumed that the first display unit 100 is the main screen and the second display unit 200 is the touch screen as an example.

Referring to FIG. 12, the ultrasound apparatus 1000 may sense an occurrence of a touch event that the pointer 400 (e.g., a finger) touches the second display unit 200 during displaying an ultrasound image of the object on a first region 1201 of the first display unit 100, that is, the main screen. In this case, the ultrasound apparatus 1000 may display the plurality of control items displayed on the second display unit 200, on the first display unit 100 so as not to be overlaid on the ultrasound image.

For example, the ultrasound apparatus 1000 may display a plurality of menu items on the second region 1202 of the first display unit 100, which is different from the first region 1201. Here, the plurality of menu items displayed on the second region 1202 may be arranged differently from the plurality of menu items displayed on the second display unit 200. That is, the arrangement of the plurality of menu items may be changed according to a size of the second region 1202.

According to the exemplary embodiment, the ultrasound apparatus 1000 may reduce a size of the ultrasound image displayed on the first region 1201 in order to display the plurality of menu items displayed on the second display unit 200 on the first display unit 100. For example, if the ultrasound image occupies 90% of the entire screen of the first display unit 100 or greater, the ultrasound apparatus 1000 may reduce the size of the ultrasound image to ⅔ in order to display the plurality of menu items.

According to the exemplary embodiment, the ultrasound apparatus 1000 may change a location of the ultrasound image in order to display the plurality of menu items of the second display unit 200 on the first display unit 100. For example, if the ultrasound image is displayed on a center portion of the first display unit 100, the ultrasound apparatus 1000 may move the ultrasound image to a left side to display the plurality of menu items on a right side of the first display unit 100.

According to the exemplary embodiment, the ultrasound apparatus 1000 may display an indicator that indicates a touch location of the pointer 400 on the second display unit 200, on the first display unit 100. For example, if the user touches a first item 1203 from among the plurality of menu items displayed on the second display unit 200, the ultrasound apparatus 1000 may mark an indicator of a square shape around the first item 1203 from among the plurality of menu items displayed on the first display unit 100.

Figure 13:
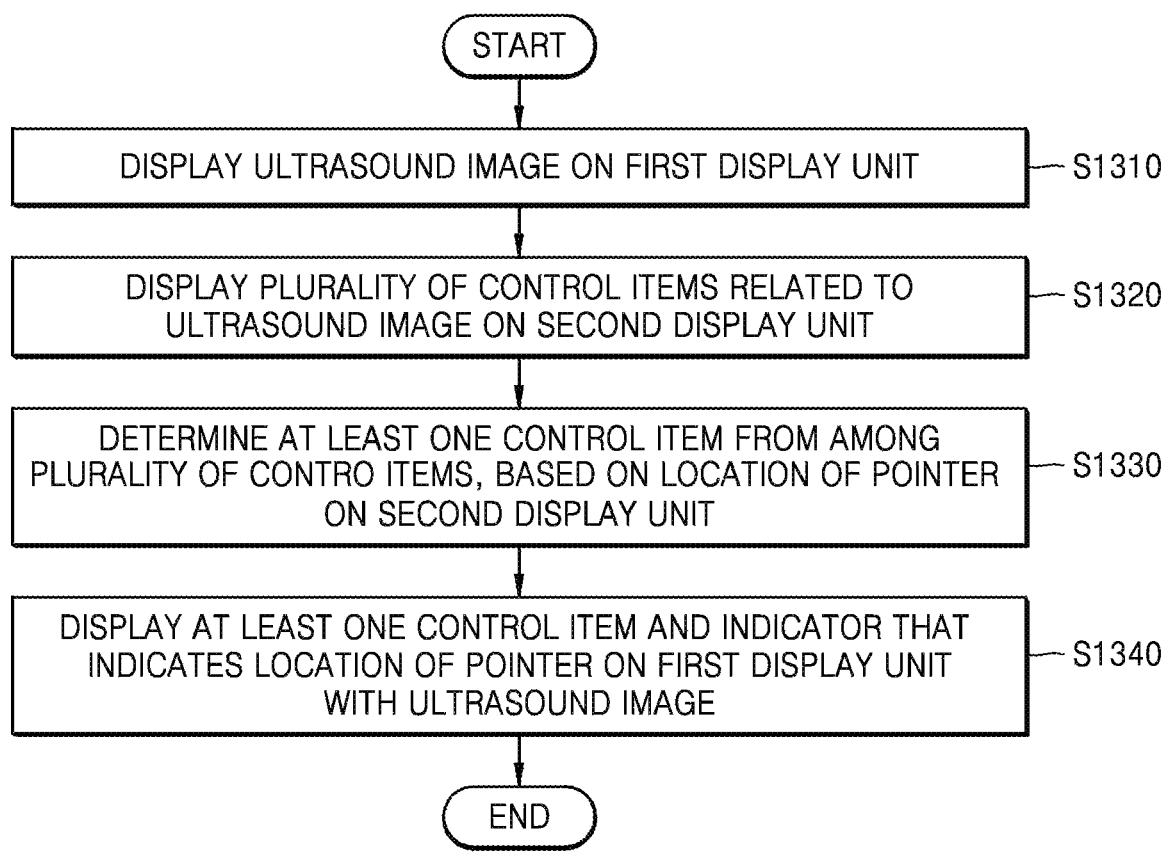
FIG. 13 is a flowchart illustrating a method for an ultrasound apparatus to provide information by using a plurality of display units, according to an exemplary embodiments.

FIG. 13 is a flowchart illustrating a method for the ultrasound apparatus 1000 to provide information by using a plurality of display units, according to an exemplary embodiment.

In operation S1310, the ultrasound apparatus 1000 may display an ultrasound image on the first display unit 100.

According to the exemplary embodiment, the ultrasound apparatus 1000 may display ultrasound images obtained via the probe 20 on the first display unit 100 in real-time. In addition, according to the exemplary embodiment, the ultrasound apparatus 1000 may display ultrasound images stored in the storage medium in advance on the first display unit 100.

The ultrasound image may include at least one of a B mode image, a C mode image, a D mode image, an M mode image, and an elastic mode image, but is not limited thereto. In addition, according to the exemplary embodiment, the ultrasound image may be a 2D image, a 3D image, or a 4D image.

In operation S1320, the ultrasound apparatus 1000 may display a plurality of control items related to the ultrasound image on the second display unit 200. For example, the ultrasound apparatus 1000 may display a plurality of control items for adjusting parameter values related to the ultrasound image displayed on the first display unit 100, on the second display unit 200.

The plurality of control items related to the ultrasound image may include at least one of items such as a frequency, a dynamic range, a frame average, a reject level, a gray map, a spatial compount, a dynamic magnetic resonance (DMR+), a harmonic, a scan area, an edge enhance, a speed, a power, a line density, a full spectrum image (FSI), a focus number, a depth value, and a time gain compensation (TGC), but is not limited thereto.

The frequency item may denote an item for changing a transmitting/receiving frequency applied to the probe 20. For example, the user may select one of a penetration (Pen, low frequency), general (Gen, general frequency), and resolution (Res, high frequency) to adjust the frequency.

The dynamic range item is an item for adjusting contrast by changing a ratio between a minimum value and a maximum value of an input signal. For example, the user may select a value within a range from 50 to 200 to set a parameter value of a dynamic range.

The frame average item is an item for reducing random noise in the ultrasound image. For example, the user may select a value within a range from 0 to 15 to set a parameter value of a frame average.

The reject level item is an item for removing noise in the ultrasound image. For example, the user may select a value within a range from 1 to 32 to set a reject level value.

The gray map item is an item for determining a gray scale by changing a post curve of the ultrasound image. For example, the user may select a value within a range from 1 to 13 to set a parameter value of the gray map.

The spatial compount item is an item for adjusting density of the ultrasound image. For example, the user may select one of low/med/high to set a parameter value of the spatial compound.

The DMR+ item is an item for post-processing the ultrasound image, and may be a parameter for reducing noise and emphasizing an edge. For example, the user may select a value within a range from 1 to 5 to set a parameter value of the DMR+.

The harmonic item is an item for optimizing the ultrasound image by using high frequency. For example, the user may select one of on and off to set a parameter value of the harmonic item.

The scan area item is an item for adjusting a transverse width (%) of the ultrasound image. For example, the user may select a value within a range from 40 to 100 to adjust the width of the scan area.

The edge enhance item is an item for sharpening a boundary of a tissue or an organ. For example, the user may select a value within a range from −3 to 3 to set a parameter value of the edge enhance item.

The speed item is an item for improving a resolution by adjusting a velocity of the organ. For example, the user may select a value within a range from 1440 to 1620 (m/s) to adjust the value of the speed level.

The power item is an item for selecting an intensity of an ultrasound wave output. For example, the user may select a value within a range from 10 to 100 to adjust a power value.

The line density item is an item for adjusting density of the ultrasound image. For example, the user may select one of low/mid1/mid2/high to adjust a line density value.

The FSI item is an item for adjusting a ratio of mixing frequencies. For example, the user may select a value within a range from 1 to 3 to set a parameter value of the FSI 1370.

The focus number item is an item for setting a location of a focus and the number of focus. For example, the user may select a value within a range from 1 to 4 to adjust the focus number.

The gain item is an item for adjusting brightness of the ultrasound image. For example, the user may select a value within a range from 1 to 100 to adjust the gain value.

The depth item is an item for adjusting a depth of the ultrasound image that is scanned. The depth value according to the exemplary embodiment may vary depending on a kind of the probe 20. For example, if the probe 20 of the ultrasound apparatus 1000 is a convex probe, the user may select a depth value within a range from 6 cm to 30 cm.

The TGC item is an item used to compensate for a reduction in a transmission degree of the ultrasound wave according to a depth of a human body. For example, the user may adjust the TGC value by moving an adjustment button on a slide bar corresponding to a plurality of depth sections.

According to the exemplary embodiment, the plurality of control items for adjusting the parameter values related to the ultrasound image displayed on the first display unit 100 may be displayed in a plurality of pages. For example, the ultrasound apparatus 1000 may display a first item to a tenth item on a first page, and may display an eleventh item to a twentieth item on a second page.

In operation S1330, the ultrasound apparatus 1000 may select at least one control item from among the plurality of control items displayed on the second display unit 200, based on the location of the pointer 400 on the second display unit 200.

According to the exemplary embodiment, the ultrasound apparatus 1000 may recognize the pointer 400 touching the second display unit 200 via at least one sensor. Here, the touch may include a contact-type touch and a non contact-type touch (hovering). In addition, the ultrasound apparatus 1000 may sense a touched location of the pointer 400 via at least one sensor. Here, the at least one sensor may be at least one of a touch sensor, a pressure sensor, a proximity sensor, an image sensor, a depth sensor, and an infrared sensor, but is not limited thereto.

Since the method for the ultrasound apparatus 1000 to sense the location of the pointer 400 is described above with reference to FIGS. 5 to 8, detailed descriptions thereof are omitted.

According to the exemplary embodiment, the ultrasound apparatus 1000 may select at least one control item located within a predetermined distance from the touched location of the pointer 400, from among the plurality of control items. For example, the ultrasound apparatus 1000 may select the first item, the second item, the third item, and the fourth item located within a radius of 5 cm from the touched location of the pointer 400.

According to the exemplary embodiment, the ultrasound apparatus 1000 may select a menu group corresponding to the location of the pointer 400 from among a plurality of menu groups displayed on the second display unit 200, so as to determine at least one control item.

For example, if the touched location of the pointer 400 overlaps with a first menu group, the ultrasound apparatus 1000 may select a first menu item, a second menu item, a third menu item, a fourth menu item, and a fifth menu item included in a first menu group among the plurality of control items.

In operation S1340, the ultrasound apparatus 1000 may display the determined at least one control item and the indicator that indicates the location of the pointer 400, on the first display unit 100 with the ultrasound image.

According to the exemplary embodiment, the ultrasound apparatus 1000 may mark the indicator on the at least one control item. For example, if the pointer 400 is located at the first item from among the at least one control item displayed on the second display unit 200, the ultrasound apparatus 1000 may mark the indicator on the first item on the first display unit 100.

According to the exemplary embodiment, the ultrasound apparatus 1000 may change the location of the indicator on the first display unit 100, as the location of the pointer 400 on the second display unit 200 is changed.

According to the exemplary embodiment, the ultrasound apparatus 1000 may display the at least one control item and the indicator that indicates the location of the pointer 400 to be overlaid on the ultrasound image on the first display unit 100. Here, the ultrasound apparatus 1000 may determine a transparency of the at least one control item displayed on the ultrasound image based on the predefined transparency information, and may display the at least one control item to be transparent according to the determined transparency.

Otherwise, the ultrasound apparatus 1000 may display the at least one control item on the first display unit 100 so as not to be overlaid on the ultrasound image. For example, the ultrasound apparatus 1000 may display the ultrasound image on a first region of the first display unit 100 and may display the at least one control item including the indicator on a second region of the first display unit 100. An operation of the ultrasound apparatus 1000 for displaying the at least one control item on the first display unit so as not to be overlaid on the ultrasound image will be described below with reference to FIG. 14.

Figure 14:
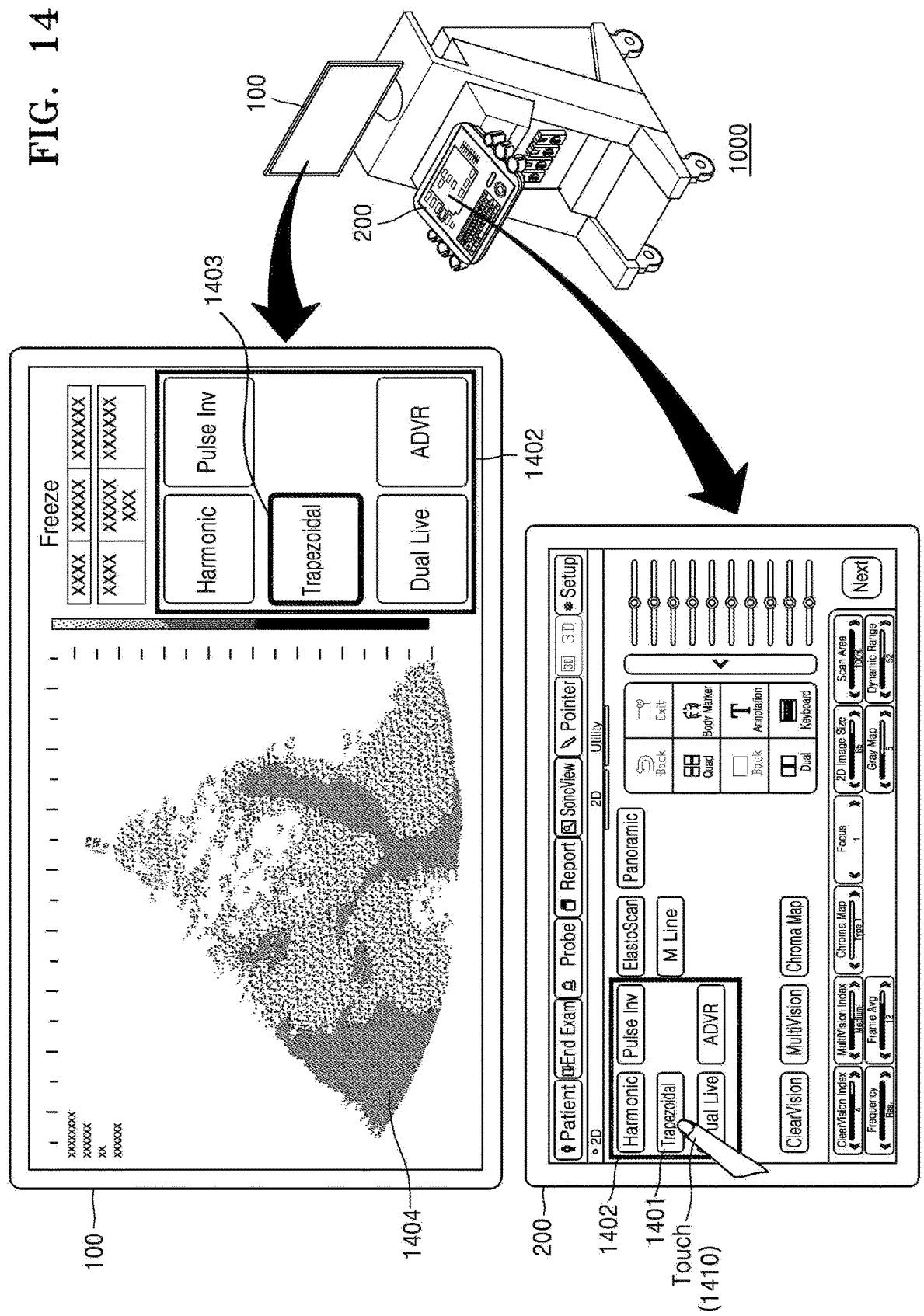
FIG. 14 is a diagram illustrating an example, in which an ultrasound apparatus displays some of control items displayed on a touch screen on a main screen, according to an exemplary embodiment.

FIG. 14 is a diagram illustrating an example, in which the ultrasound apparatus 1000 displays some of control items displayed on the touch screen, on the main screen. In FIG. 14, it is assumed that the first display unit 100 is a main screen on which the ultrasound image is displayed and the second display unit 200 is a touch screen on which the control items are displayed as an example.

The ultrasound apparatus 1000 may display the ultrasound image on the first display unit 100 and display the plurality of control items on the second display unit 200.

Here, the ultrasound apparatus 1000 may receive an input 1410 of touching a trapezoidal item 1401 from among the plurality of control items displayed on the second display unit 200 by using the pointer 400. The ultrasound apparatus 1000 may select a first menu group 1402 including the trapezoidal item 1401, from among the plurality of control items, wherein the first menu group 1402 may include, for example, a harmonic item, a pulse Inv item, the trapezoidal item 1401, a dual live item, and an ADVR item.

The ultrasound apparatus 1000 may display the first menu group 1402 on the first display unit 100. Here, the ultrasound apparatus 1000 may display the first menu group 1402 at a right side of the first display unit 100 so as not to overlap with the ultrasound image 1404 displayed at a left side of the first display unit 100.

The ultrasound apparatus 1000 may display an indicator 1403 that indicates the current location of the pointer 400 on the first display unit 100. Since the pointer 400 is located on the trapezoidal item 1401 on the second display unit 200, the ultrasound apparatus 1000 may represent the indicator 1403 as a boundary around the trapezoidal item 1402 in the first menu group 1402 displayed on the first display unit 100.

If the user drags the pointer 400 in contact with the second display unit 200, the ultrasound apparatus 1000 may move the indicator 1043 according to the movement of the pointer 400.

According to the exemplary embodiment, if the touch event on the second display unit 200 is finished at an empty space where the control item is not displayed, the first menu group 1402 displayed on the first display unit 100 may be removed.

For example, if the user moves his/her finger that has contacted the trapezoidal item 1401 aside and takes his/her finger off the second display unit 200 at the empty space next to the trapezoidal item 1401, and then, touches a body maker item displayed on the second display unit 200 by his/her finger, the ultrasound apparatus 1000 may display a second menu group including the body maker item on the first display unit 100, instead of the first menu group 1402, wherein the second menu group may include, for example, a quad item, the body maker item, an annotation item, a dual item, and a keyboard item).

Figure 15:
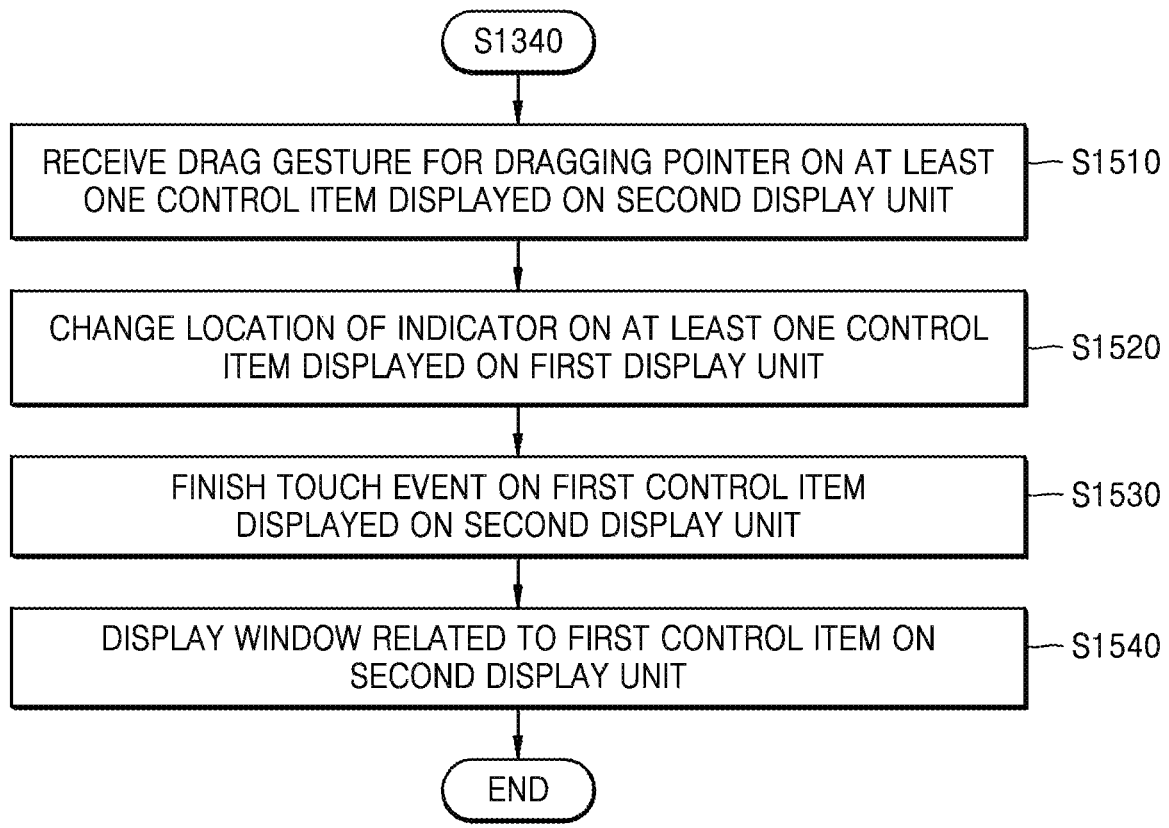
FIG. 15 is a flowchart illustrating a method for an ultrasound apparatus to display a window corresponding to a certain control item selected from at least one control item, according to an exemplary embodiment.

FIG. 15 is a flowchart illustrating a method for the ultrasound apparatus 1000 to display a window corresponding to a selected control item among the at least one control item.

According to the exemplary embodiment, operation S1510 of FIG. 15 may be executed after operation S1340 of FIG. 13. Therefore, in FIG. 15, an example in which the at least one control item displayed on the second display unit 200 and the indicator that indicates the location of the pointer 400 on the second display unit 200 are displayed on the first display unit 100 with the ultrasound image will be described below.

In operation S1510, the ultrasound apparatus 1000 may receive a drag gesture that drags the pointer 400 on at least one control item displayed on the second display unit 200. For example, the ultrasound apparatus 1000 may sense the location of the pointer 400 dragging on the second display unit 200 by using a touch sensor, a pressure sensor, or a camera.

In operation S1520, the ultrasound apparatus 1000 may change the location of the indicator on the at least one control item displayed on the first display unit 100, based on the drag gesture for dragging the pointer 400. For example, if the pointer 400 on the second display unit 200 is dragged to a left side (for example, from a second control item toward a first control item), the ultrasound apparatus 1000 may move the indicator on the first display unit 100 to the left side (for example, from a second control item toward the first control item).

In operation S1530, the ultrasound apparatus 1000 may sense that the touch event has finished on the first control item displayed on the second display unit 200.

For example, the ultrasound apparatus 1000 may sense that the user takes his/her finger off the second display unit 200 on the first control item by using the touch sensor (sensing variation in capacitance), the pressure sensor (sensing variation in pressure), or the camera (analyzing image frames). In this case, the ultrasound apparatus 1000 may determine that the user selects the first control item.

In operation S1540, the ultrasound apparatus 1000 may display a window related to the first control item on the second display unit 200, when the touch event has finished on the first control item.

Here, the window may be a GUI for adjusting the parameter value of the first control item, a window including information or content related to the first control item, an icon related to the first control item, or a measurement tool (e.g., width measurement, length measurement, circumferent measurement, etc.), but is not limited thereto.

According to the exemplary embodiment, the ultrasound apparatus 1000 may also display the window related to the first control item on the first display unit 100. Here, the ultrasound apparatus 1000 may mark an indicator that indicates the current location of the pointer 400 in the window displayed on the first display unit 100.

The operation of the ultrasound apparatus 1000 for displaying the window corresponding to the control item selected from among the at least one control item will be described below with reference to FIGS. 16 to 18.

Figure 16:
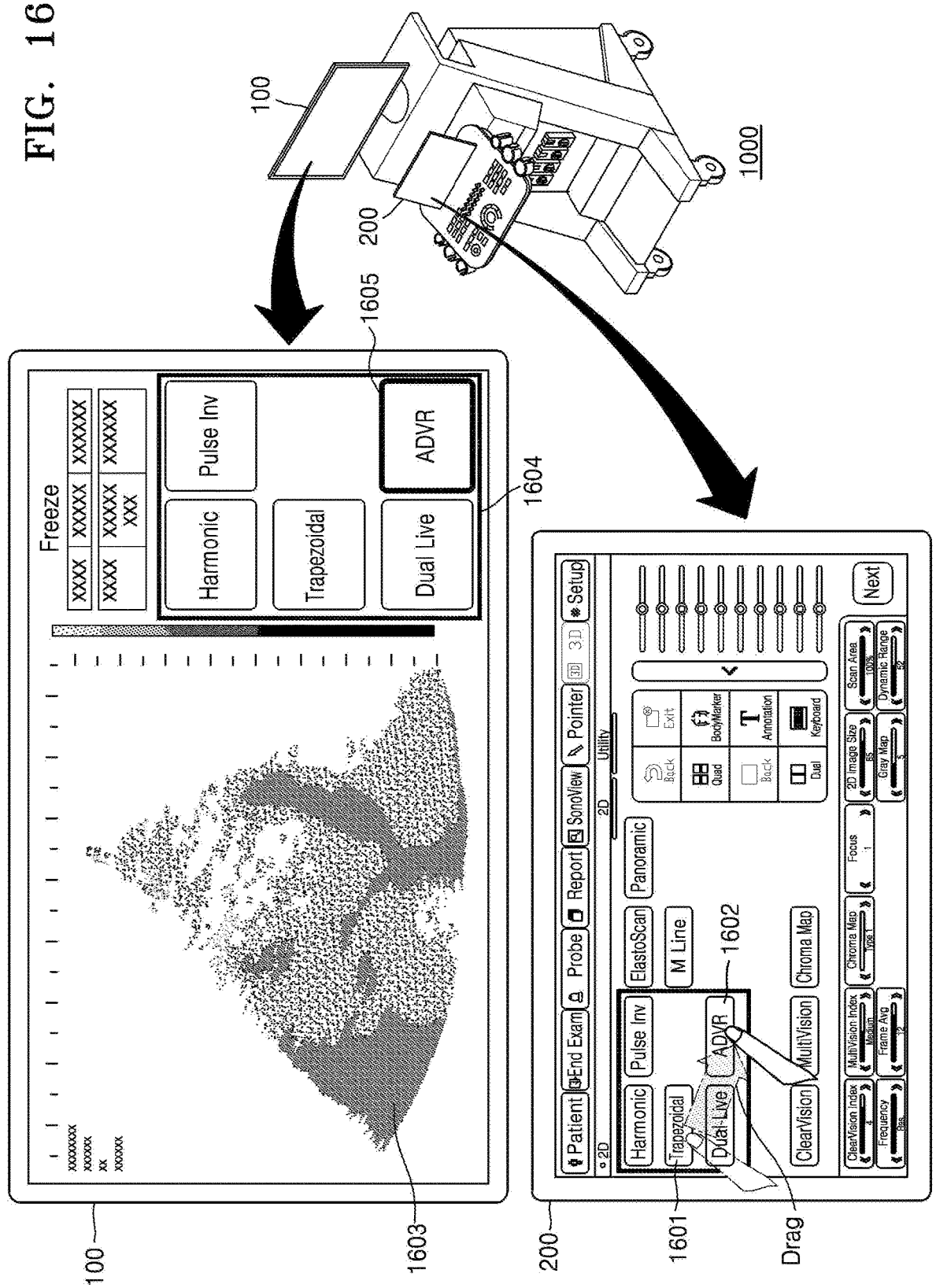
FIG. 16 is a diagram illustrating an example, in which an ultrasound apparatus moves an indicator according to a drag gesture, according to an exemplary embodiment.

FIG. 16 is a diagram illustrating an example, in which the ultrasound apparatus 1000 moves the indicator according to the drag gesture.

Referring to FIG. 16, the ultrasound apparatus 1000 may display the ultrasound image on the first display unit 100 and may display a plurality of control items on the second display unit 200. Here, the ultrasound apparatus 1000 may receive a touch input onto a trapezoidal item 1601 by using the pointer 400, from among the plurality of control items displayed on the second display unit 200. The ultrasound apparatus 1000 may display a first menu group including the trapezoidal item 1601 from among the plurality of control items on the first display unit 100, wherein the first menu group may include a harmonic item, a pulse Inv item, the trapezoidal item 1601, a dual live item, and an ADVR item.

Here, the ultrasound apparatus 1000 may display the first menu group on a second region 1604 of the first display unit 100 so as not to overlay the first menu group with the ultrasound image displayed on a first region 1603 of the first display unit 100.

In addition, the ultrasound apparatus 1000 may display an indicator 1605 that indicates the current location of the pointer 400 on the first display unit 100. For example, if the pointer 400 is located on the trapezoidal item 1601 on the second display unit 200, the ultrasound apparatus 1000 may mark the indicator 1605 as a boundary line around the trapezoidal item 1601 in the first menu group displayed on the second region 1604.

If the user drags the pointer 400 in contact with the second display unit 200, the ultrasound apparatus 1000 may move the indicator 1605 according to the movement of the pointer 400. For example, if the user drags the pointer 400 from the trapezoidal item 1601 onto the ADVR item 1602, the ultrasound apparatus 1000 senses the drag gesture and moves the indicator 1605 on the first display unit 100 from the trapezoidal item 1601 toward the ADVR item 1602.

Figure 17:
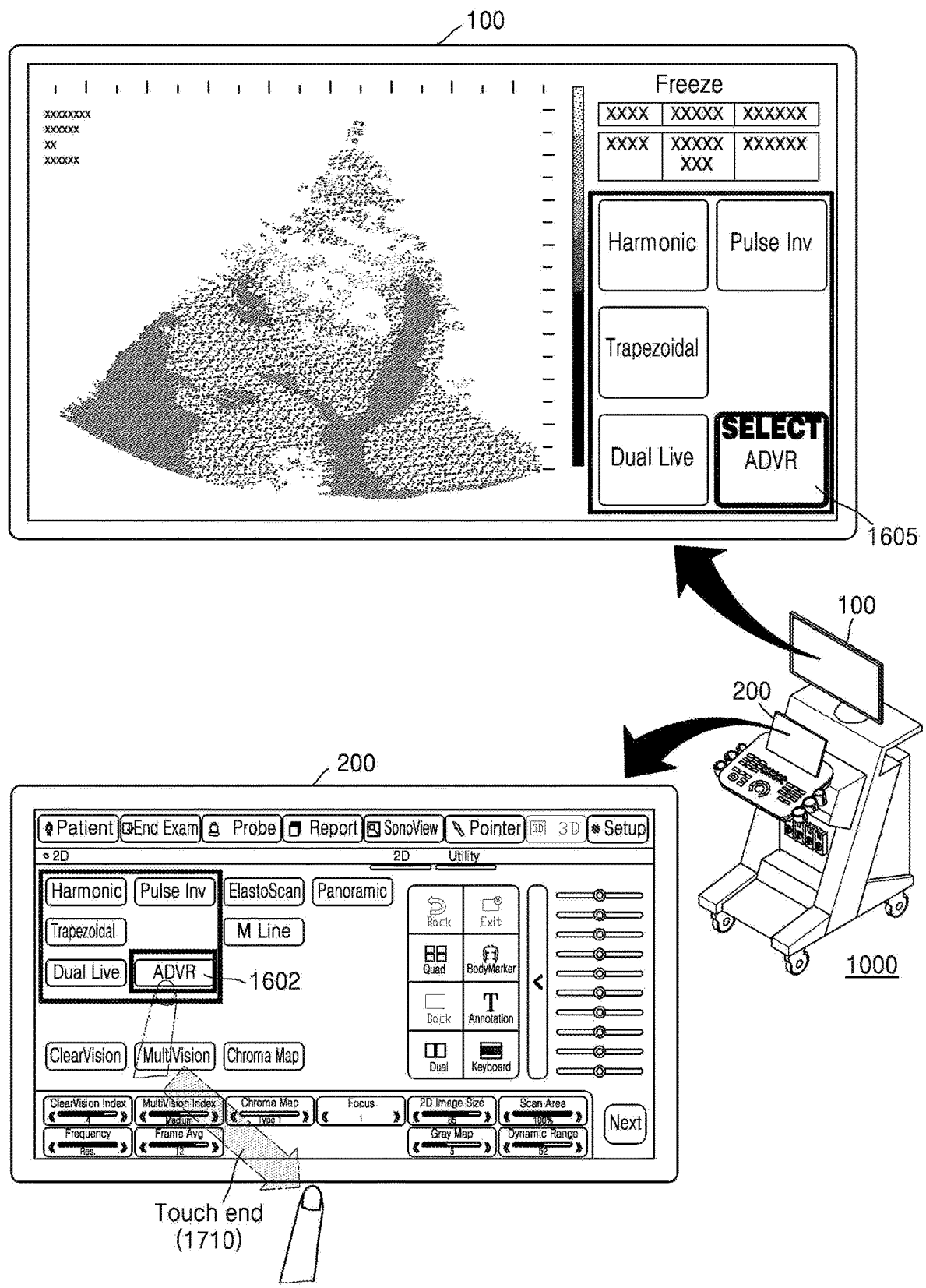
FIG. 17 is a diagram illustrating an example, in which an ultrasound apparatus selects a certain control item based on a touch end event, according to an exemplary embodiment.

FIG. 17 is a diagram illustrating an example in which the ultrasound apparatus 1000 selects a control item based on a touch end event.

Referring to FIG. 17, the ultrasound apparatus 1000 may sense that the touch event has finished (1710) on the ADVR item 1602 displayed on the second display unit 200. In this case, the ultrasound apparatus 1000 may determine that the user selects the ADVR item 1602 from among the plurality of control items.

Figure 18:
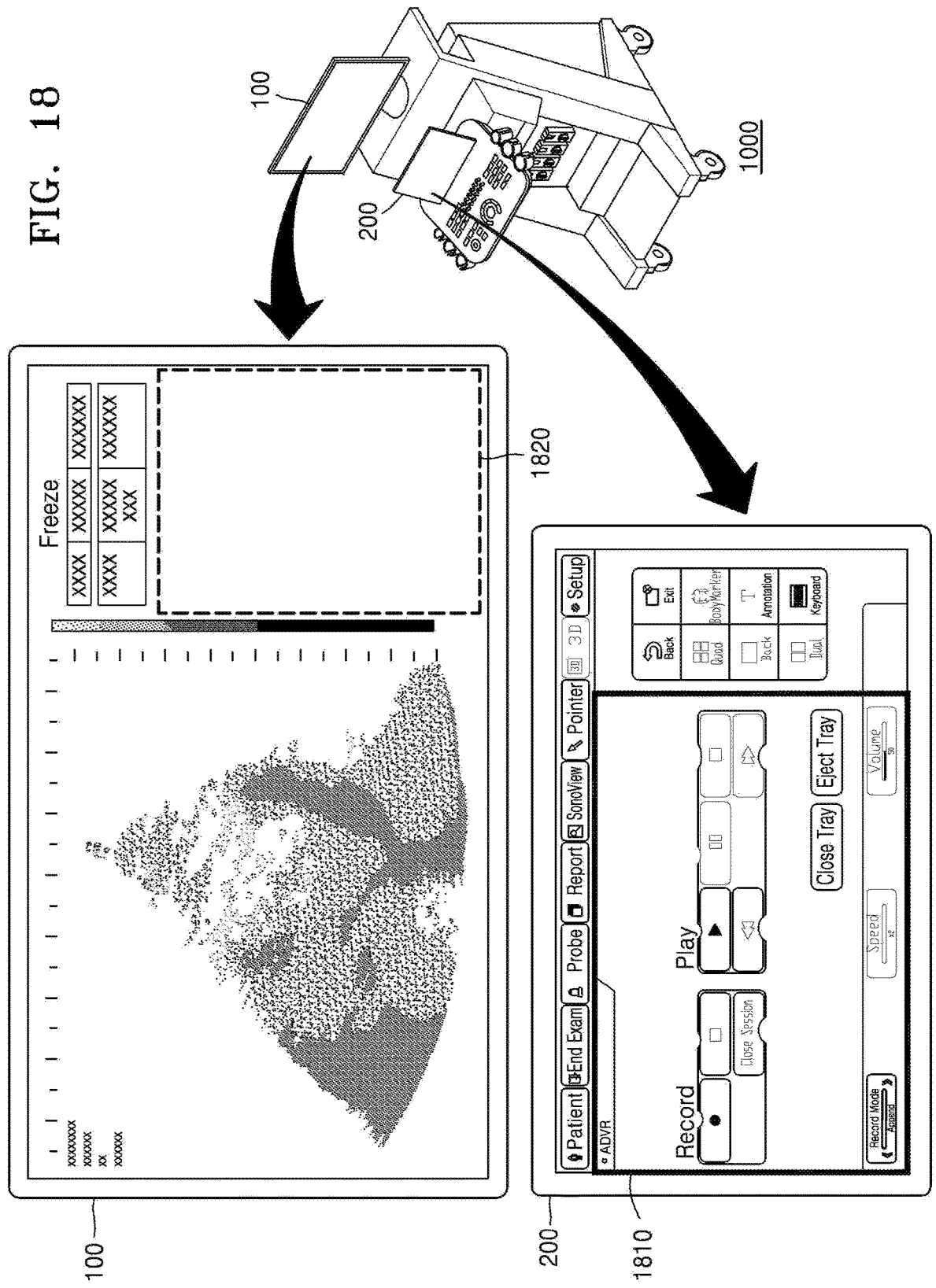
FIG. 18 is a diagram illustrating a method for an ultrasound apparatus to display a window corresponding to a selected control item, according to an exemplary embodiment.

FIG. 18 is a diagram illustrating an example, in which the ultrasound apparatus 1000 displays a window 1810 corresponding to the selected control item.

Referring to FIG. 18, the ultrasound apparatus 1000 may display the window 1810 related to the ADVR item 1602 on the second display unit 200. Here, the window 1810 related to the ADVR item 1602 may include a record button (a button for starting recording operation, a record stop button, a close session button (a button for terminating a record mode), a play button (a button for reproducing recorded video), a speed button (a button for setting a speed of rewind or fast forward function), a close tray button (a button for closing a media tray), an eject tray button (a button for opening the media tray), etc., but is not limited thereto.

In addition, if the touch event has finished (1710) on the ADVR item 1602 displayed on the second display unit 200, the ultrasound apparatus 1000 may not display the first menu group on a second region 1820 of the first display unit 100 any more.

Although not illustrated in FIG. 18, according to an exemplary embodiment, the ultrasound apparatus 1000 may display the window 1810 related to the ADVR item 1602 displayed on the second display unit 200, on the second region 1820 of the first display unit 100.

An operation of the ultrasound apparatus 1000 for displaying the window related to the selected control item on the first display unit 100 and on the second display unit 200 will be described later with reference to FIG. 20C.

Figure 19:
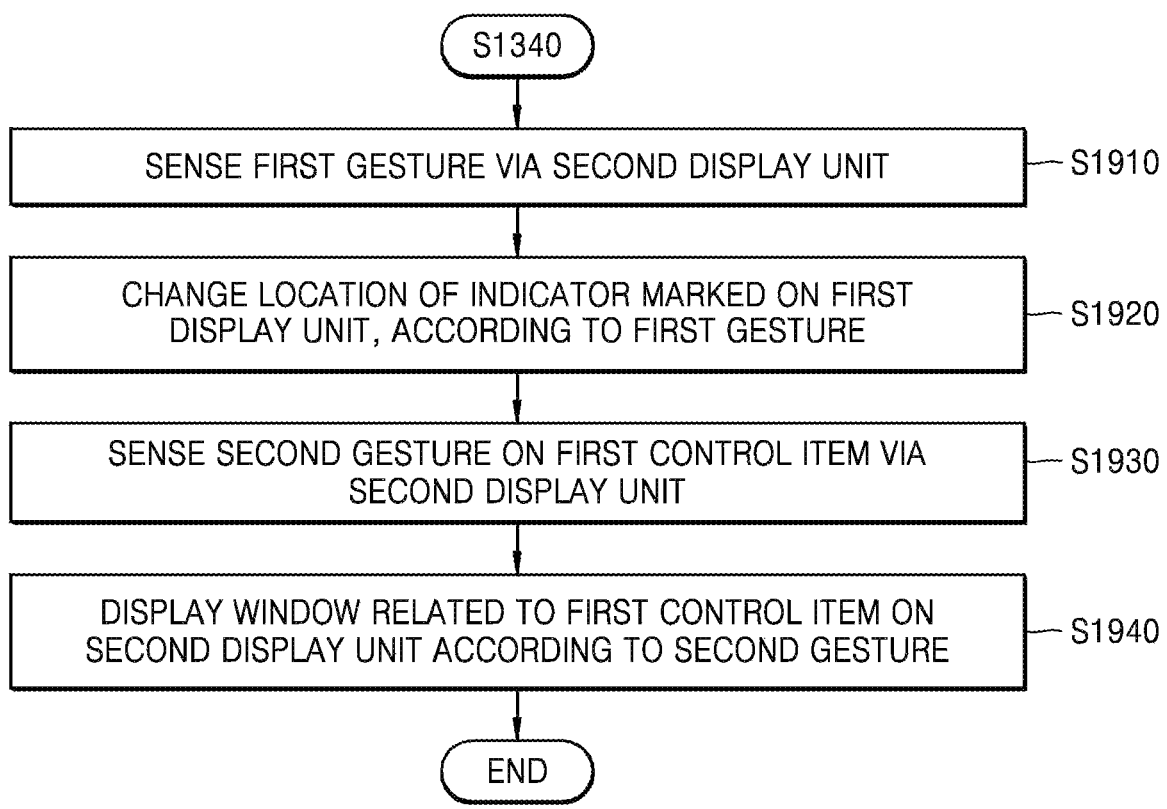
FIG. 19 is a flowchart illustrating a method for an ultrasound apparatus to change a location of an indicator or select a control item according to a touch gesture of a user, according to an exemplary embodiment.

FIG. 19 is a flowchart illustrating a method for the ultrasound apparatus 1000 to change the location of the indicator or to select the control item according to a touch gesture of the user.

Operation S1910 of FIG. 19 may be executed after operation S1340 of FIG. 13. Therefore, in FIG. 19, a case where the at least one control item displayed on the second display unit 200 and the indicator that indicates the location of the pointer 400 on the second display unit 200 are displayed on the first display unit 100 together with the ultrasound image will be described as an example.

In operation S1910, the ultrasound apparatus 1000 may sense a first gesture with respect to at least one control item via the second display unit 200. Here, the first gesture may denote a gesture for moving the indicator that indicates the location of the pointer 400. For example, the first gesture may include a drag gesture, a hovering gesture, etc., but is not limited thereto.

In operation S1920, the ultrasound apparatus 1000 may change the location of the indicator displayed on the first display unit according to the first gesture. For example, if the pointer 400 is dragged toward the left side, the indicator may be also moved to the left side.

In operation S1930, the ultrasound apparatus 1000 may sense a second gesture with respect to a first control item via the second display unit 200.

Here, the second gesture is different from the first gesture for moving the indicator, and may denote a gesture for selecting a control item. For example, if the first gesture is the drag gesture, the second gesture may be one of a touch and hold gesture, a double tap gesture, and a multi finger gesture, but is not limited thereto. Otherwise, if the first gesture is the hovering gesture, the second gesture may be a touch gesture for contacting the second display unit 200, but is not limited thereto.

The ultrasound apparatus 1000 may determine that the user selects the first control item from among the plurality of control items, upon sensing the second gesture on the first control item.

In operation S1940, the ultrasound apparatus 1000 may display a window related to the first control item on the second display unit 200 according to the second gesture. Here, the window may be a GUI for adjusting the parameter values of the first control item, a window including information or content related to the first control item, an icon related to the first control item, or a measurement tool (e.g., width measurement, length measurement, and circumference measurement), but is not limited thereto.

According to the exemplary embodiment, the ultrasound apparatus 1000 may display a user interface corresponding to the first control item on the first display unit 100 and the second display unit 200.

In addition, the ultrasound apparatus 1000 may display a first user interface from among a plurality of user interfaces related to the first control item on the first display unit 100, and may display a second user interface from among the plurality of user interfaces related to the first control item on the second display unit 200. For example, if the first control item is a TGC item, the ultrasound apparatus 1000 may display a setting window including a plurality of slide bars for setting TGC values corresponding to a plurality of depth sections on the second display unit 200, and may display a gain line interface obtained by connecting the TGC values corresponding to the plurality of depth sections on the first display unit 100.

Hereinafter, a case where the first gesture is the drag gesture and the second gesture is the double tap gesture will be described below with reference to FIGS. 20A to 20D, and a case where the first gesture is the hovering gesture and the second gesture is the touch gesture will be described below with reference to FIGS. 21A to 21C.

FIGS. 20A to 20D are diagrams illustrating an example, in which the ultrasound apparatus 1000 selects a control item according to a touch gesture of the user received via the touch screen and displays a window corresponding to the control item on the main screen.

Figure 20A:
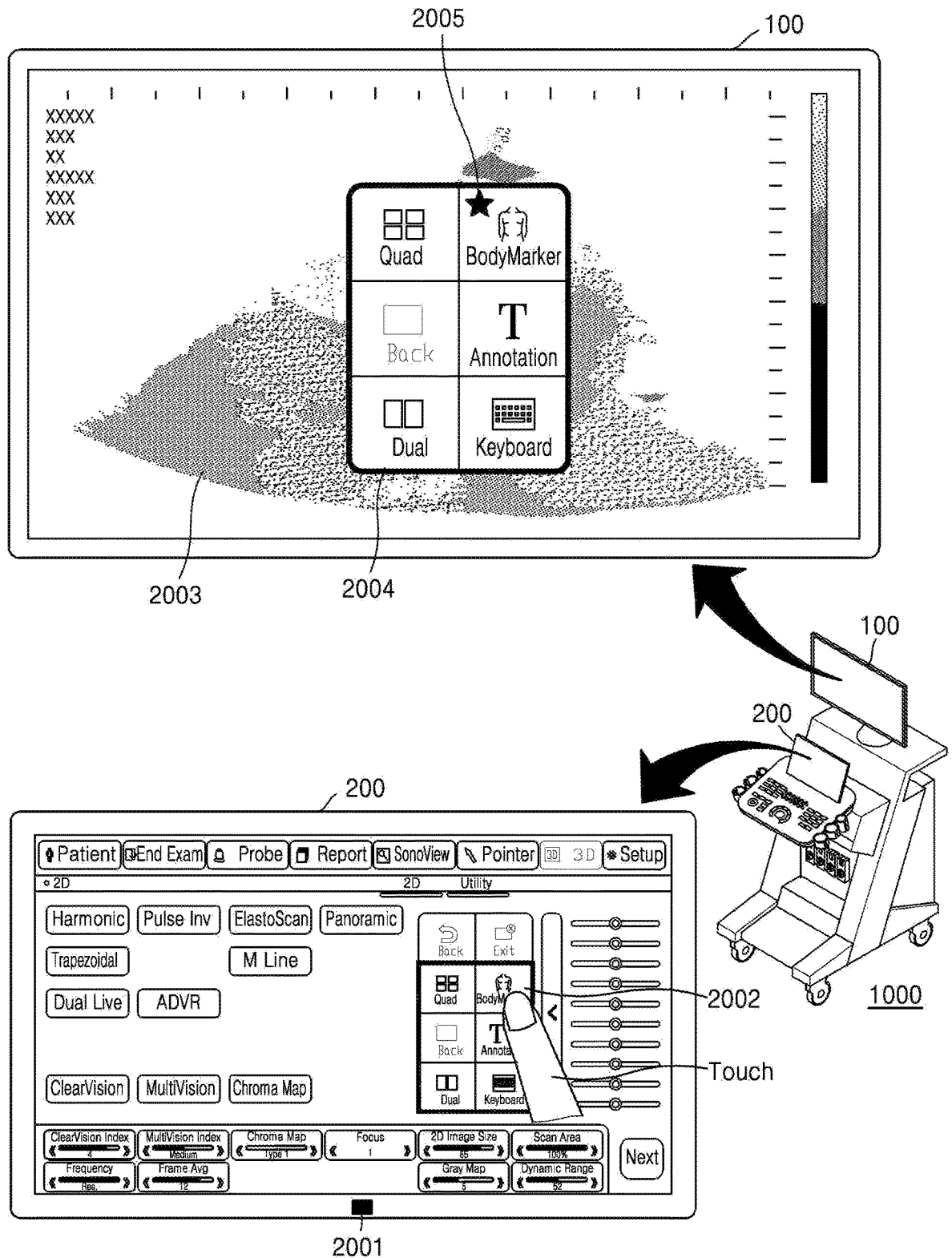
FIGS. 20A to 20D are diagrams illustrating an example, in which an ultrasound apparatus selects a certain control item according to a touch gesture of a user received through a touch screen and displays a window corresponding to the certain control item on a main screen, according to an exemplary embodiment.

Referring to FIG. 20A, the ultrasound apparatus 1000 may receive a user input that pushes a first button 2001 included in the second display unit 200. In this case, the ultrasound apparatus 1000 may activate a function of displaying some of the plurality of control items displayed on the second display unit 200, on the first display unit 100.

The ultrasound apparatus 1000 may receive a touch gesture for touching a body marker item 2002 from among the plurality of control items displayed on the second display unit 200 by using the pointer 400, after the first button 2001 is pushed. The body marker may denote a figure representing a location to which the ultrasound wave is irradiated or the object. An example of the body marker may include a liver shape, a heart shape, a womb shape, a breast shape, etc.

The ultrasound apparatus 1000 may display a control item group 2004 including the body marker item 2002 on the first display unit 100 according to the touch gesture, wherein the control item group 2004 may include a quad item, the body marker item 2002, an annotation item, a dual item, and a keyboard item. Here, the ultrasound apparatus 1000 may display the control item group 2004 on an ultrasound image 2003.

In addition, the ultrasound apparatus 1000 may mark an indicator 2005 that indicates the current location of the pointer 400 on the first display unit 100. For example, since the pointer 400 is located on the body marker item 2002 on the second display unit 200, the ultrasound apparatus 1000 may mark the indicator 2005 as a star shape on the body marker item 2002 in the control item group 2004 displayed on the first display unit 100.

When the user drags the pointer 400 in contact with the second display unit 200, the ultrasound apparatus 1000 may move the indicator 2005 according to the movement of the pointer 400. For example, when the user drags the pointer 400 from the body marker 2002 to the quad item, the ultrasound apparatus 1000 may move the indicator 2005 from the body marker item 2002 to the quad item.

Figure 20B:
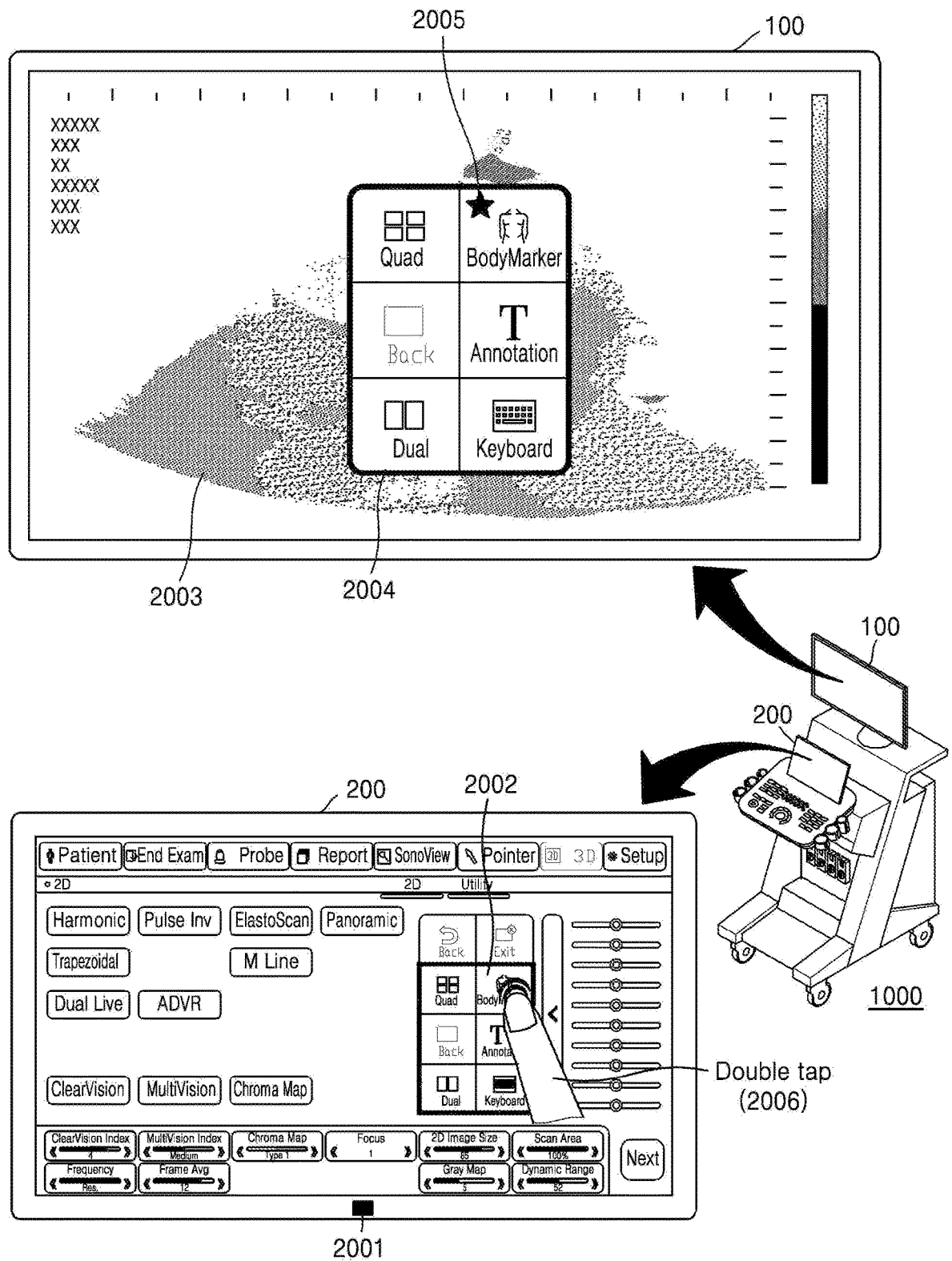

Referring to FIG. 20B, the ultrasound apparatus 1000 may receive a double tap gesture 2006 with respect to the body marker item 2002. In this case, the ultrasound apparatus 1000 may determine that the user selects the body marker item 2002 from among the plurality of control items.

Figure 20C:
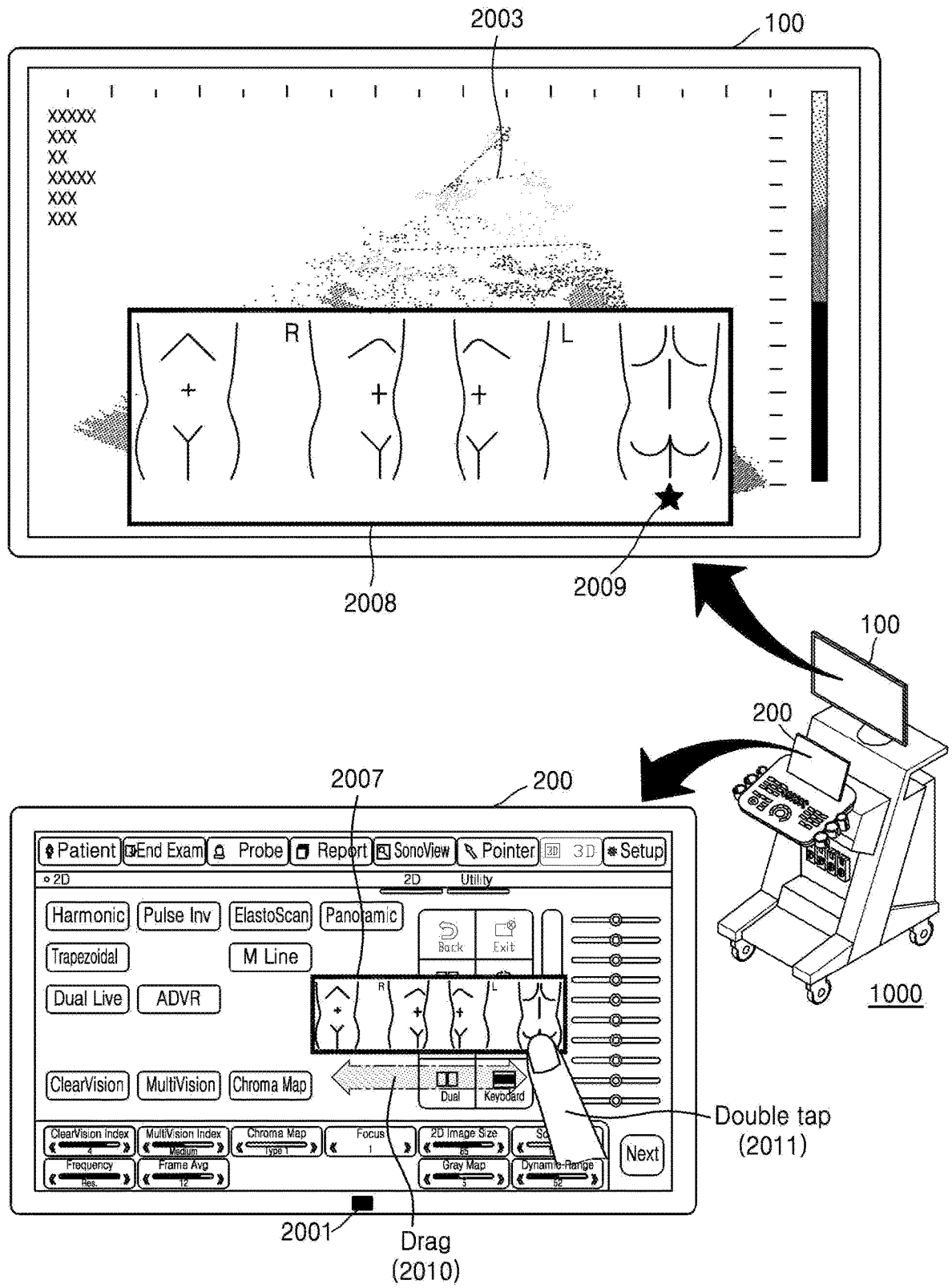

Referring to FIG. 20C, the ultrasound apparatus 1000 may display a body marker list 2007 on the second display unit 200 in response to the double tap gesture 2006. The ultrasound apparatus 1000 may display a body marker list 2008 on the first display unit 100.

In addition, the ultrasound apparatus 1000 may mark an indicator 2009 that indicates the current location of the pointer 400 within the body marker list 2008 of the first display unit 100. For example, since the pointer 400 is located on a fourth body marker on the second display unit 200, the ultrasound apparatus 1000 may mark the indicator 2009 as a star on the fourth body marker within the body marker list 2008 displayed on the first display unit 100.

If the user drags (2010) the pointer 400 in contact with the second display unit 200, the ultrasound apparatus 1000 may move the indicator 2009 according to the movement of the pointer 400. For example, if the user drags (2010) the pointer 400 from a first body marker to the fourth body marker, the ultrasound apparatus 1000 may move the indicator 2009 displayed on the second display unit 200 from the first body marker onto the fourth body marker.

The ultrasound apparatus 1000 may receive a double tap gesture 2011 with respect to the fourth body marker. In this case, the ultrasound apparatus 1000 may determine that the user selects the fourth body marker within the body marker list 2007.

Figure 20D:
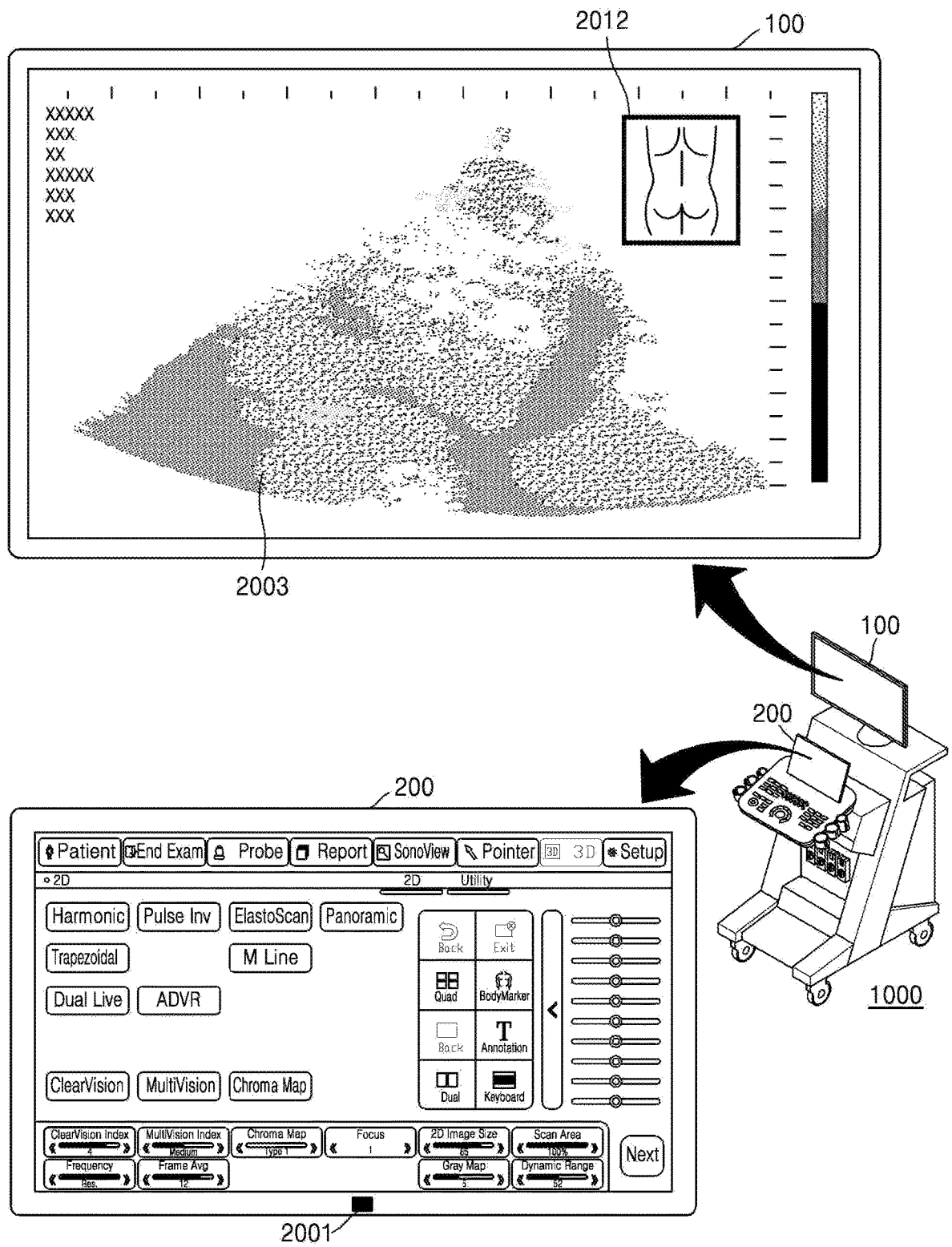

Referring to FIG. 20D, the ultrasound apparatus 1000 may display the fourth body marker 2012 on a partial region of the first display unit 100 in response to the double tap gesture 2011. In addition, according to the exemplary embodiment, the ultrasound apparatus 1000 may store matching information between the ultrasound image 2003 and the fourth body marker.

Figure 21A:
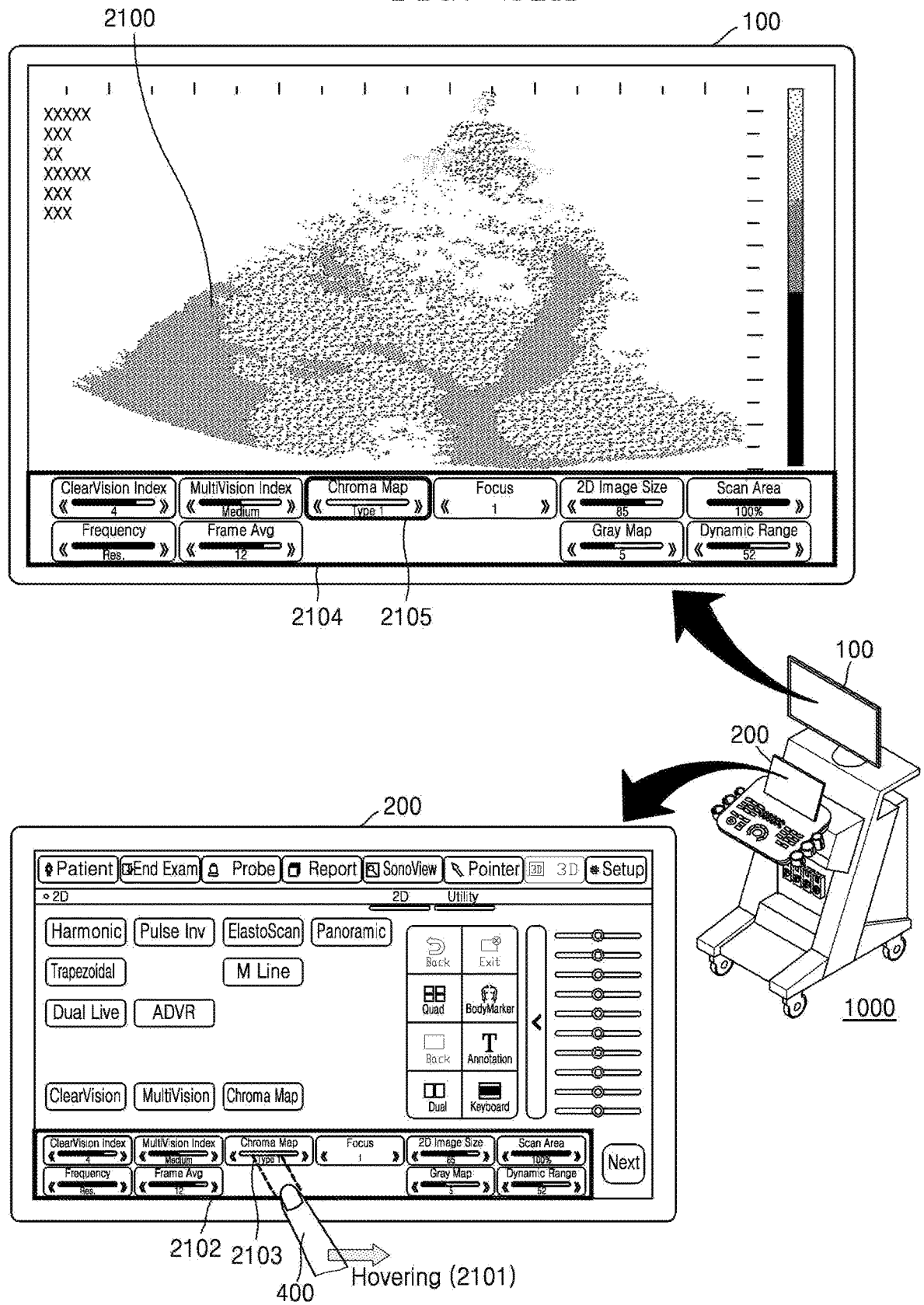
FIGS. 21A to 21C are diagrams illustrating an example, in which an ultrasound apparatus moves an indicator according to a hovering gesture of a user and selects a control item according to a touch gesture of the user, according to an exemplary embodiment.
Figure 21B:
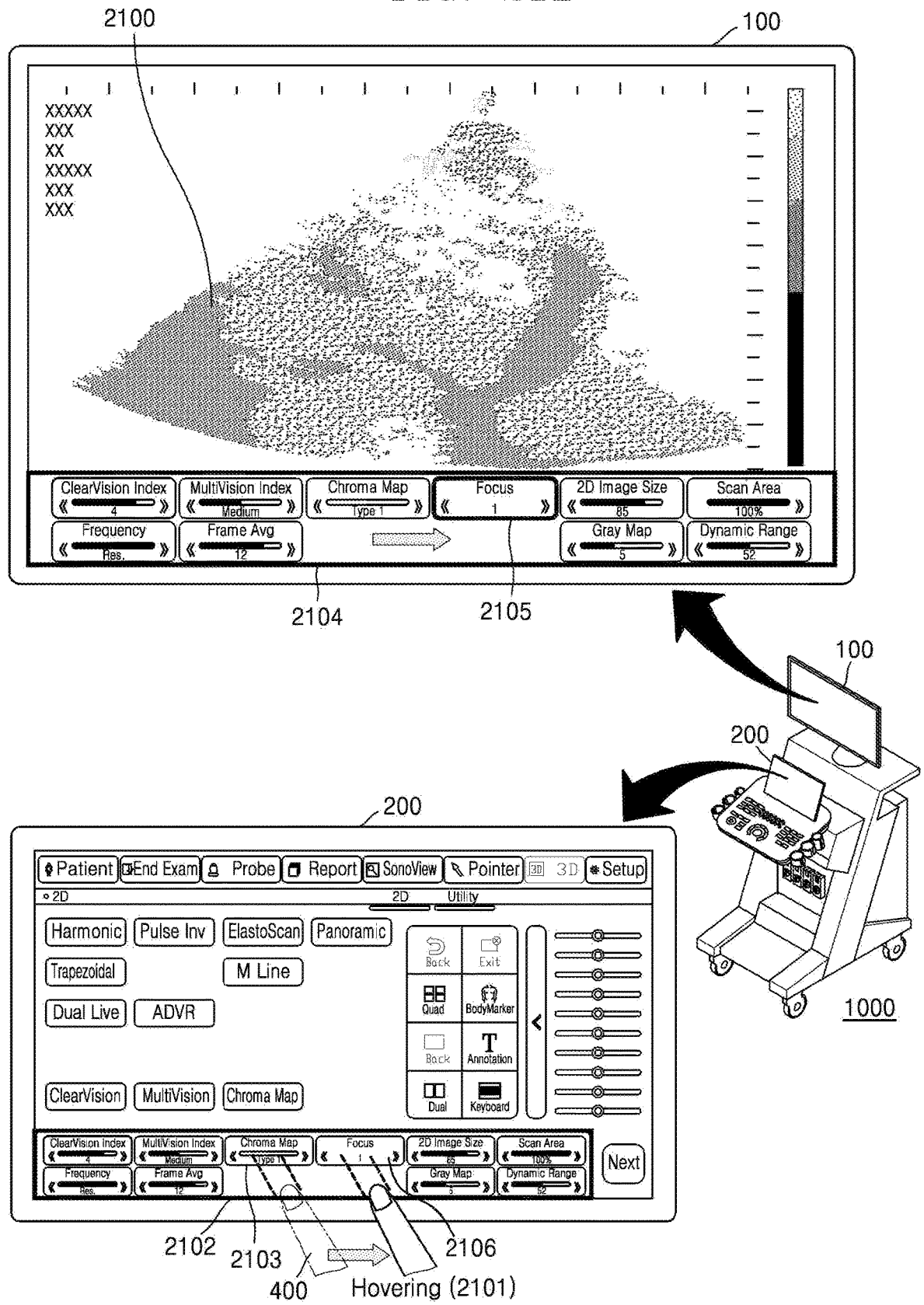
Figure 21C:
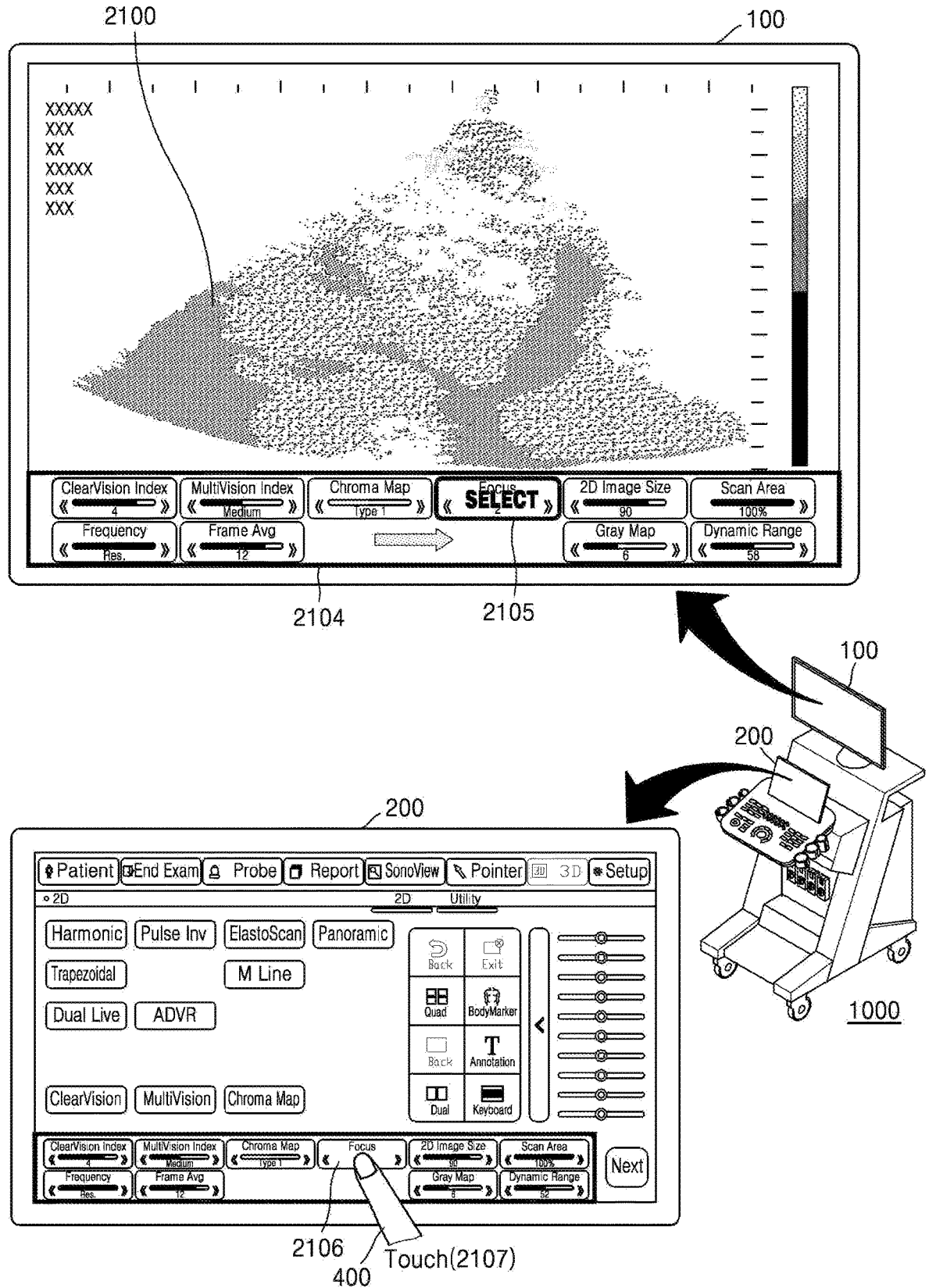

FIGS. 21A to 21C are diagrams illustrating an example, in which the ultrasound apparatus 1000 moves an indicator according to a hovering gesture of the user and selects a control item according to a touch gesture of the user.

Referring to FIG. 21A, the ultrasound apparatus 1000 may sense the pointer 400 hovering (2101) above the second display unit 200 within a predetermined height (e.g., 0.5 cm) without contacting the second display unit 200 and a location of the pointer 400.

When sensing the hovering (2101) of the pointer 400 above the second display unit 200, the ultrasound apparatus 1000 may display at least one control item on the first display unit 100. For example, if the pointer 400 is located at a certain height (e.g., 2 cm) from a chroma item 2103, the ultrasound apparatus 1000 may determine a menu group 2102 including the chroma map item 2103. In addition, the ultrasound apparatus 1000 may display a plurality of items included in the menu group 2102 (e.g., a clearvision index, a multivision index, the chroma map 2103, a focus, a 2D image size, a scan area, a frequency, a frame avg., a gray map, and a dynamic range) on the first display unit 100.

For example, the ultrasound apparatus 1000 may display the plurality of items included in the menu group 2102 on a first region 2104 that partially overlaps with an ultrasound image 2100. Here, the ultrasound apparatus 1000 may determine sizes of the plurality of items displayed on the first display unit 100, based on a ratio between screen sizes of the first display unit 100 and the second display unit 200.

The ultrasound apparatus 1000 may mark an indicator 2105 that indicates the current location of the pointer 400 on the first display unit 100. For example, if the pointer 400 is located at a certain height (e.g., 2 cm) from the chroma map item 2103, the ultrasound apparatus 1000 may mark the indicator 2105 of a square shape around the chroma map item 2103 from among the plurality of items displayed on the first region 2104 of the first display unit 100.

Referring to FIG. 21B, the ultrasound apparatus 1000 may move the indicator 2105 according to the movement of the pointer 400. For example, if the user hovers the pointer 400 from above the chroma map item 2103 to above the focus item, the ultrasound apparatus 1000 may move the indicator 2105 from the chroma map item 2103 onto the focus item.

Referring to FIG. 21C, when the pointer 400 touches a focus item 2106 displayed on the second display unit 200 (2107), the ultrasound apparatus 1000 may sense the touch gesture on the focus item 2106. Then, the ultrasound apparatus 1000 may determine that the user selects the focus item 2106 in the menu group 2102.

Figure 22:
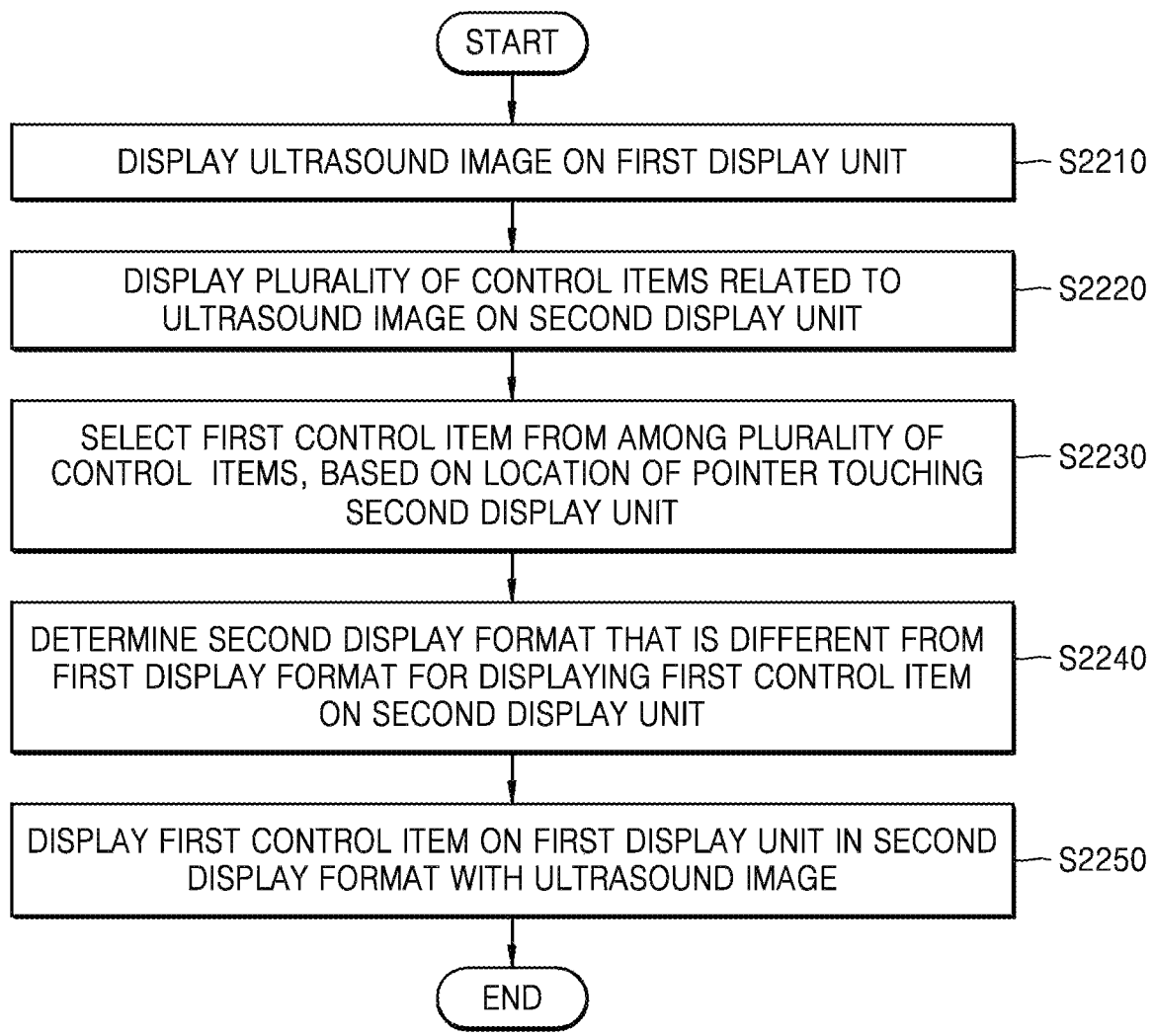
FIG. 22 is a flowchart illustrating a method for an ultrasound apparatus to display control items in different display types on a plurality of display units, according to an exemplary embodiment.

FIG. 22 is a flowchart illustrating a method for the ultrasound apparatus 1000 to display control items on a plurality of display units in different display formats.

In operation S2210, the ultrasound apparatus 1000 may display an ultrasound image on the first display unit 100.

According to the exemplary embodiment, the ultrasound apparatus 1000 may display ultrasound images obtained via the probe 20 in real time on the first display unit 100. In addition, according to the exemplary embodiment, the ultrasound apparatus 1000 may display ultrasound images stored in a storage medium in advance on the first display unit 100.

The ultrasound image may be at least one of a B mode image, a C mode image, a D mode image, an M mode image, and an elastic mode image, but is not limited thereto. In addition, according to the exemplary embodiment, the ultrasound image may be a 2D image, a 3D image, or a 4D image.

In operation S2220, the ultrasound apparatus 1000 may display a plurality of control items related to the ultrasound image on the second display unit 200.

For example, the ultrasound apparatus 1000 may display a plurality of control items for adjusting parameter values related to the ultrasound image displayed on the first display unit 100, on the second display unit 200.

The plurality of control items related to the ultrasound image may include at least one of items such as a frequency, a dynamic range, a frame average, a reject level, a gray map, a spatial compound, a dynamic magnetic resonance (DMR+), a harmonic, a scan area, an edge enhance, a speed, a power, a line density, a full spectrum image (FSI), a focus number, a depth value, a time gain compensation (TGC), and a body marker, but is not limited thereto.

In operation S2230, the ultrasound apparatus 1000 may select a first control item from among the plurality of control items, based on a location of the pointer 400 touching the second display unit 200.

According to the exemplary embodiment, the ultrasound apparatus 1000 may recognize the pointer 400 touching the second display unit 200 via at least one sensor. Here, the touch may include a contact-type touch and a non contact-type touch (hovering). In addition, the ultrasound apparatus 100 may sense a touched location by the pointer 400 via at least one sensor. Here, the at least one sensor may include at least one of a touch sensor, a pressure sensor, a proximity sensor, an image sensor, a depth sensor, and an infrared ray sensor, but is not limited thereto.

The method for the ultrasound apparatus 1000 to sense the location of the pointer 400 is described above with reference to FIGS. 5 to 8, and thus, detailed descriptions thereof are omitted.

According to the exemplary embodiment, the ultrasound apparatus 1000 may select a first control item from among the plurality of control items, when the pointer 400 is located above the first control item for a predetermined time period or longer. For example, when receiving a touch and hold gesture that the user touches the first control item by his/her finger for three seconds or longer, the ultrasound apparatus 1000 may select the first control item from among the plurality of control items.

In addition, if the pointer 400 touches the first control item a predetermined times or greater (e.g., twice or greater), the ultrasound apparatus 1000 may select the first control item from among the plurality of control items. For example, when receiving a double tap gesture that the user touches the first control item twice or greater by his/her finger, the ultrasound apparatus 1000 may select the first control item from among the plurality of control items.

The ultrasound apparatus 1000 may select the first control item from among the plurality of control items when a plurality of pointers touch the first control item. For example, if the user touches the first control item by two or more fingers, the ultrasound apparatus 1000 may select the first control item from among the plurality of control items displayed on the second display unit 200.

In operation S2240, the ultrasound apparatus 1000 may determine a second display format that is different from a first display format for displaying the first control item on the second display unit 200.

According to the exemplary embodiment, the second display format may be simplified when comparing with the first display format. Here, simplification may denote that elements (e.g., adjustment icons) configuring the user interface are reduced. For example, the second display format may provide elements that have less complexity, a reduced number of elements or controls, etc. Moreover, the controls of the second display format may be the same as controls of the first display format except that they are enlarged and/or are reduced in number.

According to the exemplary embodiment, the first display format may include a left and right bar and a slide bar, and the second display format may include a slide bar. Otherwise, the first display format may be a square shape including a left and right bar and a slide bar, and the second display format may be a fan shape having a plurality of sections. Otherwise, the first display format may include a plurality of slide bars and the second display format may be a line connecting values of the plurality of slide bars.

In operation S2250, the ultrasound apparatus 1000 may display the first control item in the second display format on the first display unit 100, together with the ultrasound image.

According to the exemplary embodiment, if the ultrasound apparatus 1000 senses a touch on the first control item displayed in the first display format on the second display unit 200, the ultrasound apparatus 1000 may display the first control item in the second display format on the first display unit 100 while maintaining the first control item displayed in the first display format on the second display unit 200.

According to the exemplary embodiment, the ultrasound apparatus 1000 may display the first control item on the first display unit 100 to be overlaid on the ultrasound image of the first display unit 100. Here, the ultrasound apparatus 1000 may determine a transparency of the first control item displayed on the ultrasound image based on the predefined transparency information, and may display the first control item with the determined transparency.

Otherwise, the ultrasound apparatus 1000 may display the first control item on the first display unit 100 so as not to be overlaid on the ultrasound image. For example, the ultrasound apparatus 1000 may display the ultrasound image on the first region of the first display unit 100 and may display the first control item in the second display format on the second region of the first display unit 100.

According to the exemplary embodiment, the ultrasound apparatus 1000 may determine a size of the first control item that is displayed on the first display unit 100 in the second display format, based on a ratio between screen sizes of the first display unit 100 and the second display unit 200. In addition, the ultrasound apparatus 1000 may display the first control item on the first display unit 100 in the second display format according to the determined size.

According to the exemplary embodiment, the ultrasound apparatus 1000 may sense a location of the pointer 400 touching the first control item that is displayed in the first display format, and may mark an indicator that indicates the location of the pointer 400 on the first control item that is displayed in the second display format.

According to the exemplary embodiment, the indicator that indicates the location of the pointer 400 may be realized in a predefined shape, a predefined line, a predefined color, a predefined shade, etc., but is not limited thereto.

According to the exemplary embodiment, since the location of the pointer 400 is changed on the first control item that is displayed in the first display format, the ultrasound apparatus 1000 may move the indicator on the first control item that is displayed in the second display format.

For example, the ultrasound apparatus 1000 may receive a drag input that drags the pointer 400 on the first control item displayed in the first display format, and may change the location of the indicator on the first control item that is displayed in the second display format according to the drag input.

Figure 23A:
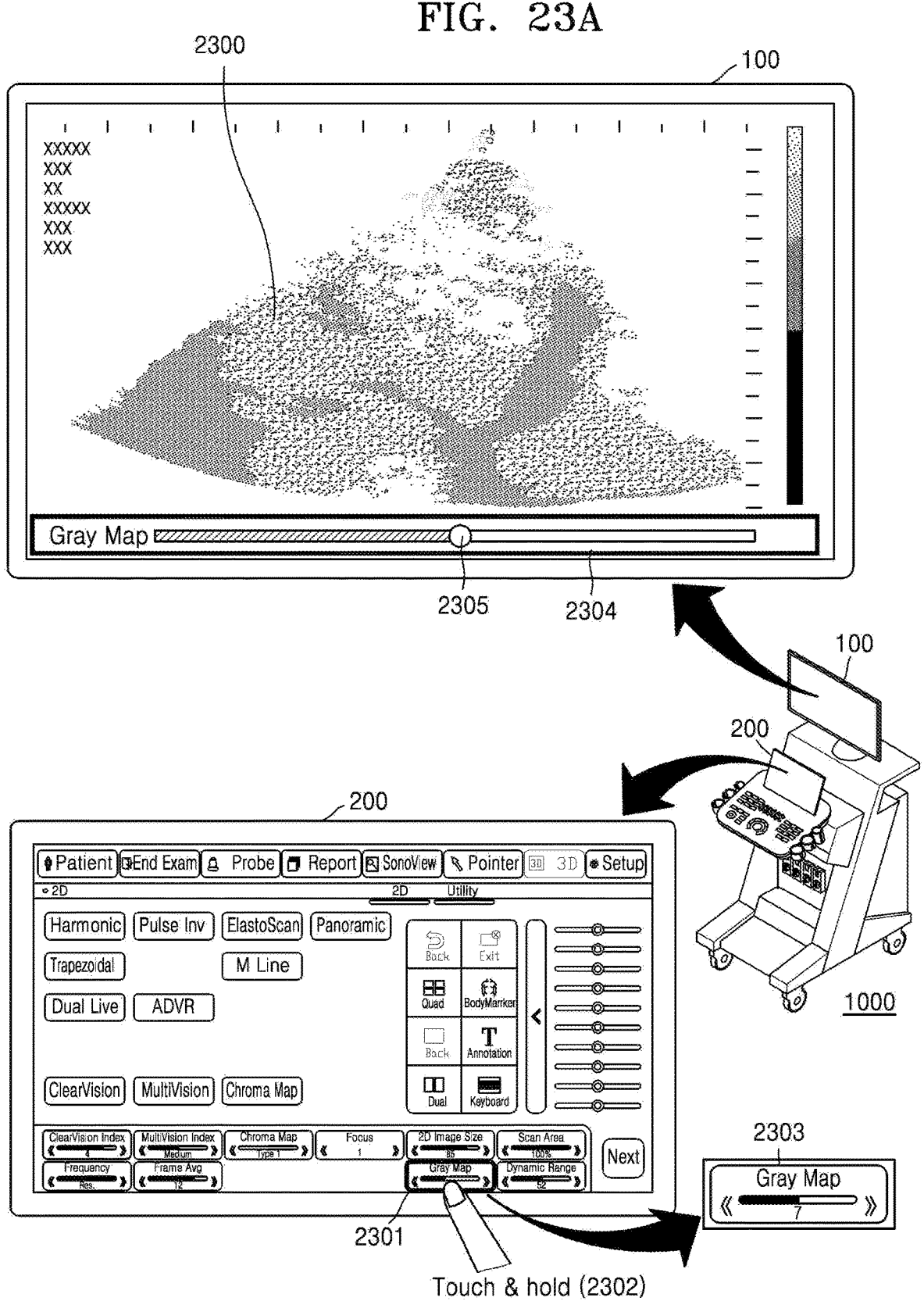
FIGS. 23A to 23C are diagrams illustrating an example, in which an ultrasound apparatus displays a control item for setting a level of a gray map to be different on a first display unit and a second display unit, according to an exemplary embodiment.
Figure 23B:
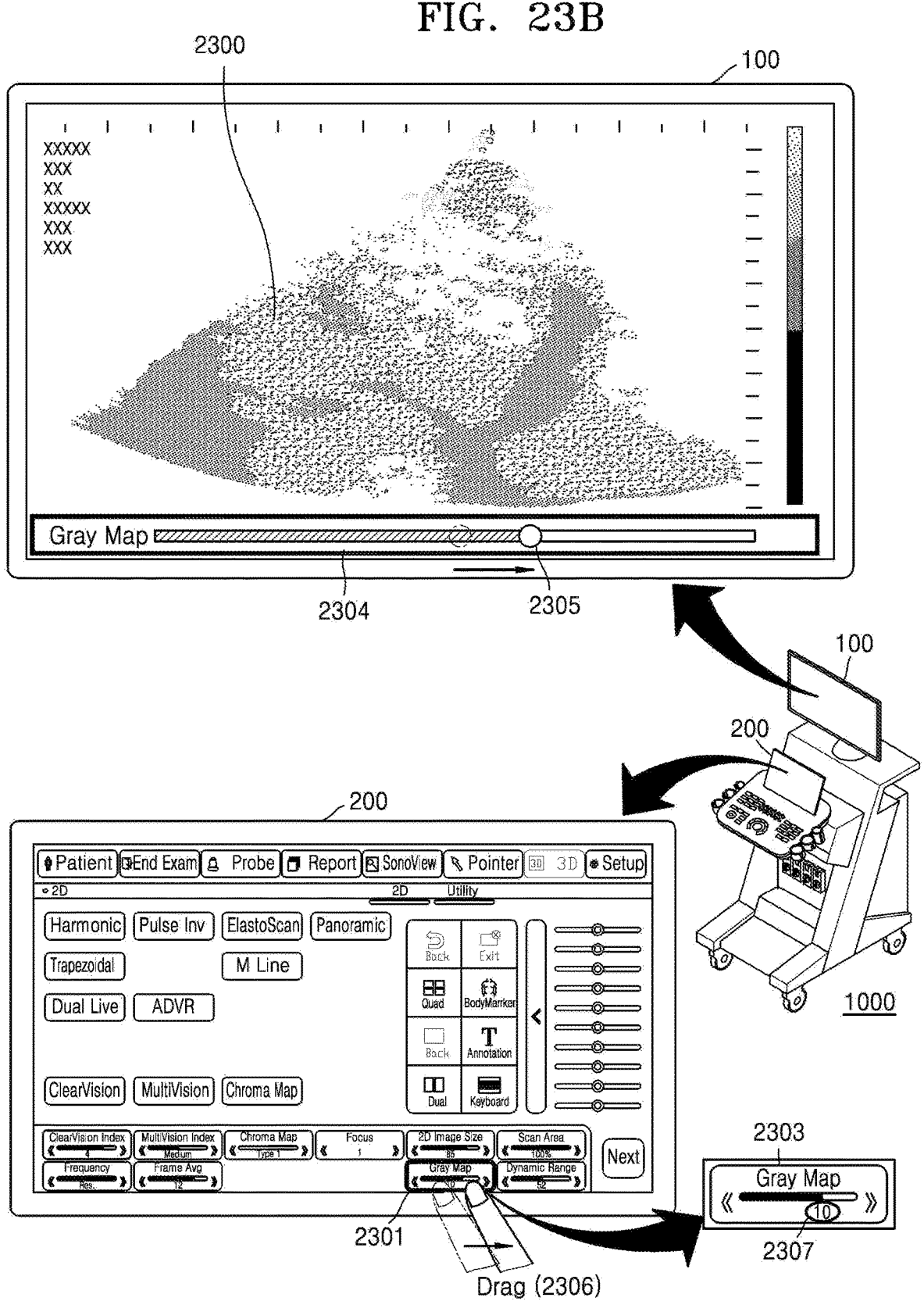
Figure 23C:
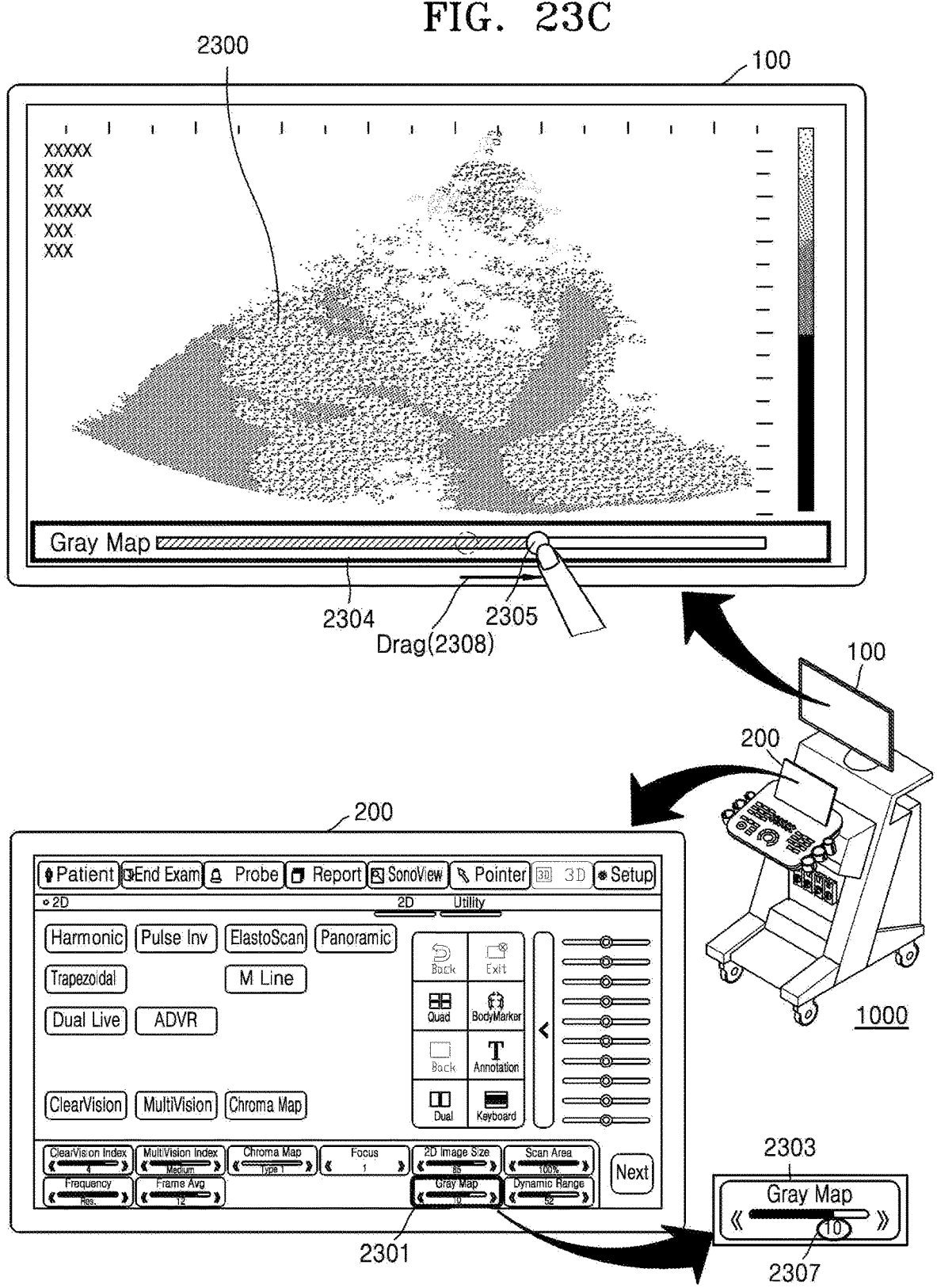

FIGS. 23A to 23C are diagrams illustrating an example, in which the ultrasound apparatus 1000 displays a control item for setting a gray map level to be different on the first display unit and the second display unit.

Referring to FIG. 23A, the ultrasound apparatus 1000 displays an ultrasound image 2300 on the first display unit 100 and may display a plurality of control items related to the ultrasound image 2300 on the second display unit 200.

The ultrasound apparatus 1000 may receive a touch and hold gesture that touches a gray map item 2301 among the plurality of control items by using the pointer 400 for a predetermined time period or longer. The ultrasound apparatus 1000 may select the gray map item 2301 from among the plurality of control items, according to a touch and hold gesture 2302. The gray map item 2301 on the second display unit 200 may displayed as a first display format 2303 including left and right keys and a slide bar.

When receiving the touch and hold gesture 2302 on the gray map item 2301, the ultrasound apparatus 1000 may determine a second display format 2304 that is different from the first display format 2303. The second display format 2304 has a simplified structure when compared with the first display format 2303, and may include a slide bar representing a level of the gray map. Information about the second display format 2304 corresponding to the first display format 2303 may be stored on a memory.

The ultrasound apparatus 1000 may display the gray map item 2301 in the second display format 2304 on the first display unit 100. Here, according to the exemplary embodiment, the ultrasound apparatus 1000 may sense a location of the pointer 400 touching the gray map item 2301 that is displayed in the first display format 2303, and may mark an indicator 2305 indicating the location of the pointer 400 on the gray map item 2301 that is displayed in the second display format 2304. For example, if the pointer 400 is located at a center of the gray map item 2301 in the first display format 2303 and a gray map level represented by the center of the first display format 2303 is 7, the ultrasound apparatus 1000 may mark the indicator 2305 at a location of the second display format 2304, on which the gray map level denotes 7.

Referring to FIG. 23B, if the user drags the pointer 400 within the gray map item 2301 in contact with the second display unit 200 (2306), the ultrasound apparatus 1000 may move the indicator 2305 according to the movement of the pointer 400. For example, if the user drags the pointer 400 to a right side within the gray map item 2301 displayed in the first display format 2303 (2306), the ultrasound apparatus 1000 may move the indicator 2305 on the slide bar included in the second display format 2304 to a right side. Here, the ultrasound apparatus 1000 may adjust a gray map level 2307 from 7 to 10.

According to the exemplary embodiment, when the user touches the gray map item 2301 on the second display unit 200 by his/her finger while fixing his/her eyes on the first display unit 100 that is the main screen, the ultrasound apparatus 1000 may display a user interface corresponding to the gray map item 2301 on the first display unit 100, together with the ultrasound image 2300. In this case, the user may adjust the gray map level by performing a simple gesture on the second display unit 200 while fixing his/her eyes on the first display unit 100 that is the main screen. The user may identify the gray map level that is adjusted through the user interface corresponding to the gray map item 2301 displayed on the first display unit 100 in real time. Therefore, the gaze of the user may not be dispersed.

Referring to FIG. 23C, if the first display unit 100 includes a touch panel, the first display unit 100 may sense a drag gesture 2308 that the user drags the indicator 2305 on the gray map item 2301 displayed in the second display format 2304 on the first display unit 100.

The ultrasound apparatus 1000 may move the indicator 2305 to the right side according to the drag gesture 2308 for dragging the indicator 2305 to the right side, and may adjust the gray map level 2307 from 7 to 10 based on the location of the indicator 2305.

Figure 24A:
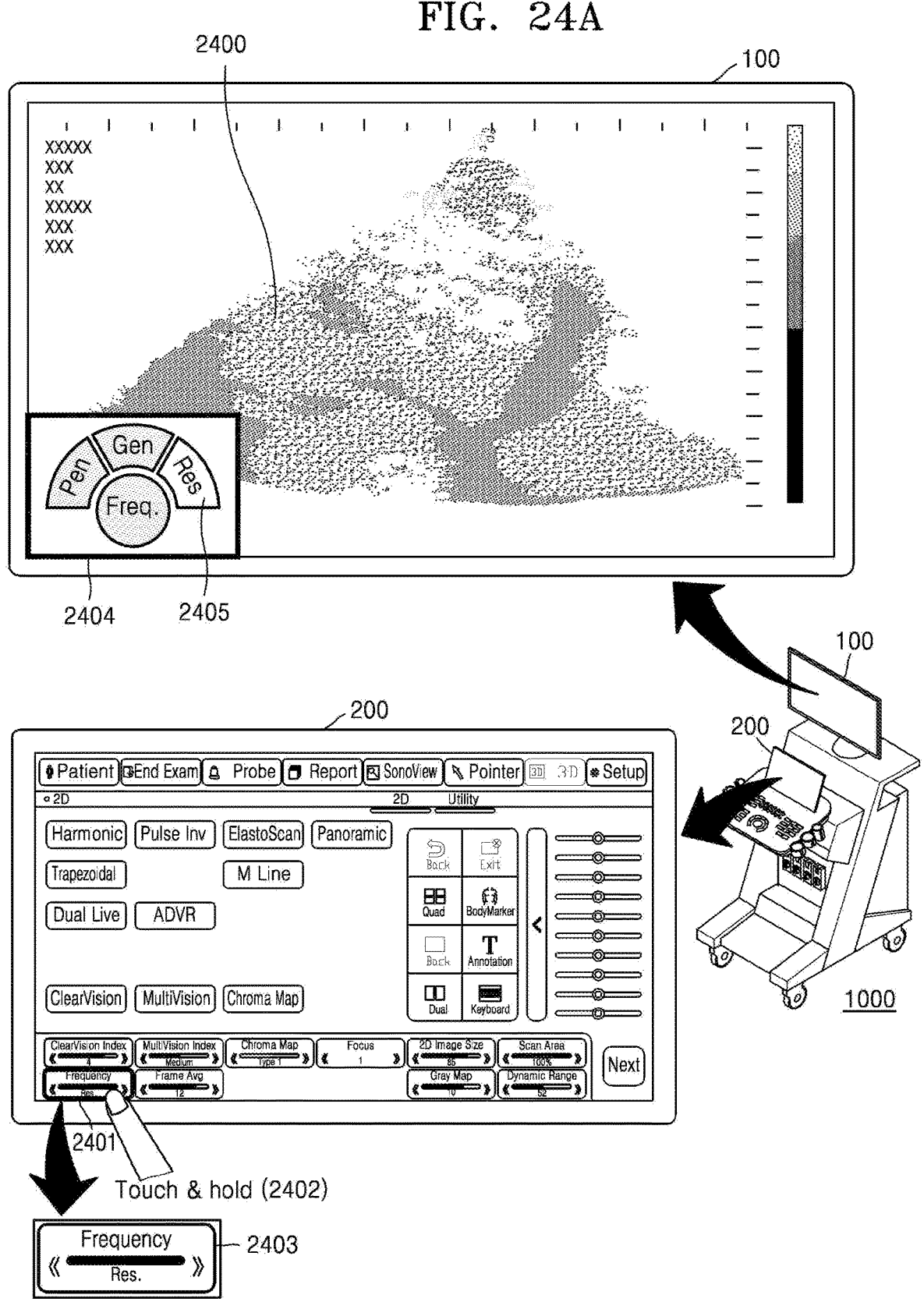
FIGS. 24A to 24C are diagrams illustrating an example, in which an ultrasound apparatus displays control items for setting frequency to be different on a first display unit and a second display unit, according to an exemplary embodiment.
Figure 24B:
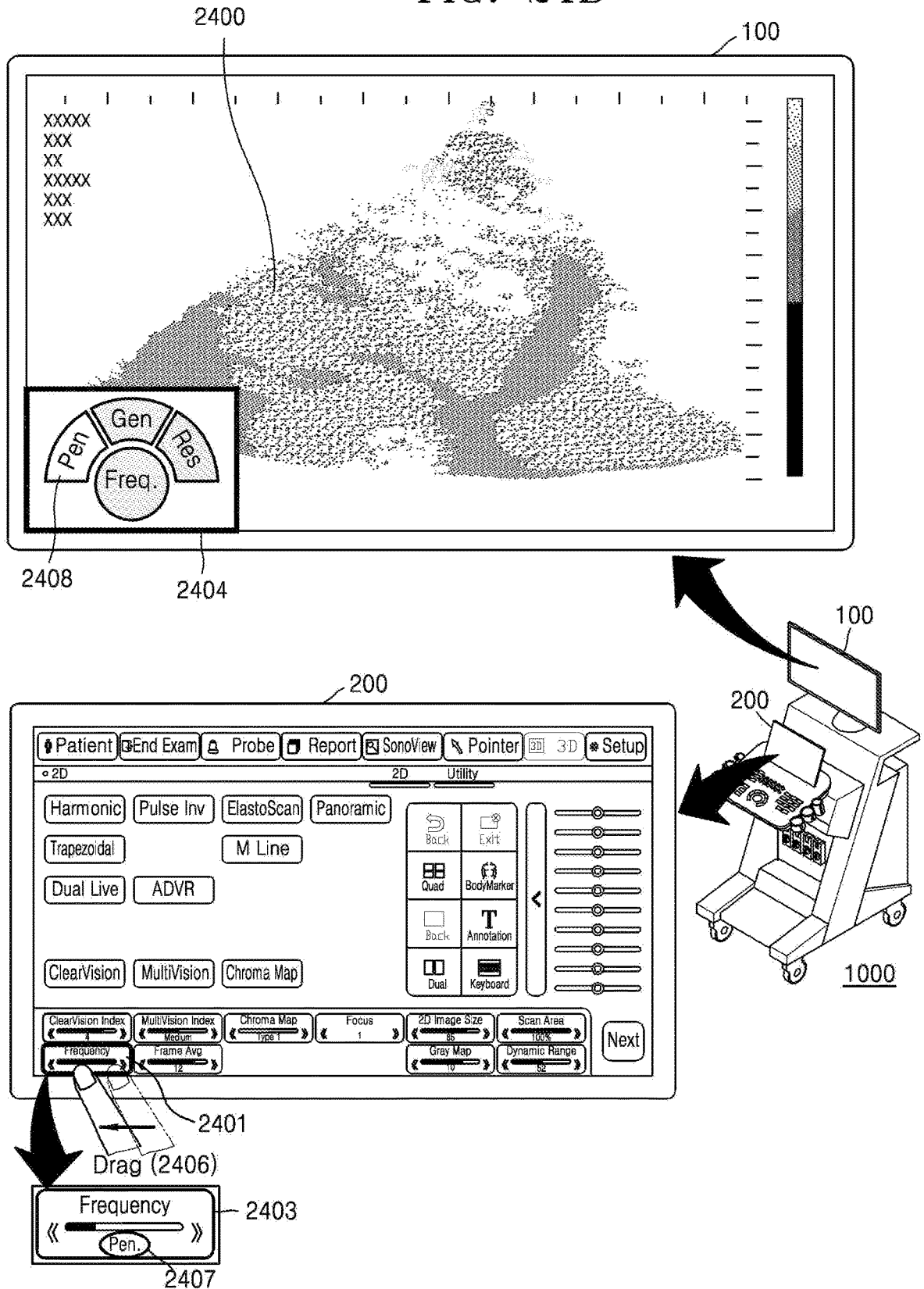
Figure 24C:
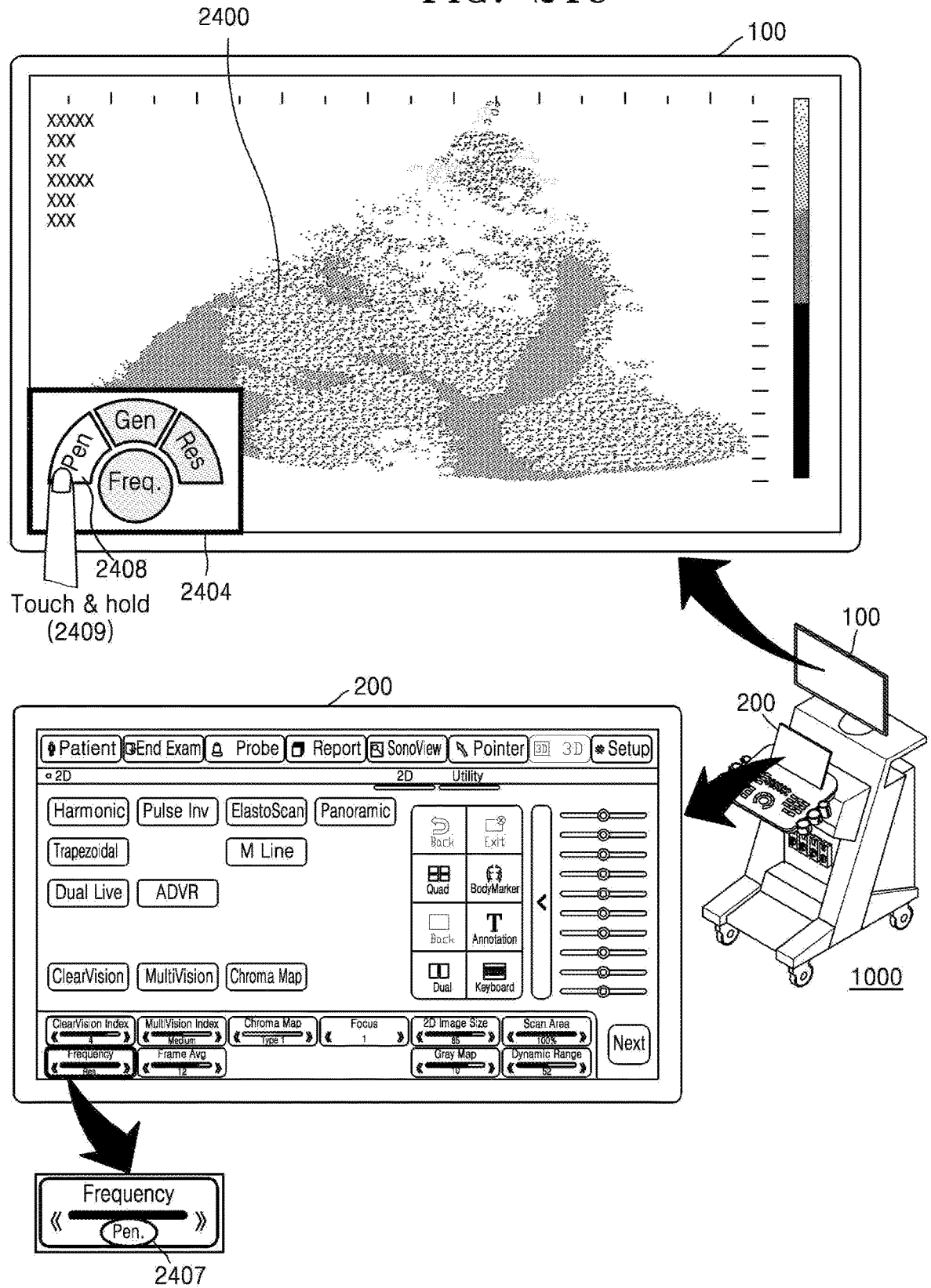

FIGS. 24A to 24C are diagrams illustrating an example in which the ultrasound apparatus 1000 displays a control item for setting frequency to be different on the first display unit 100 and the second display unit 200.

Referring to FIG. 24A, the ultrasound apparatus 1000 may display an ultrasound image 2400 on the first display unit 100, and may display a plurality of control items related to the ultrasound image 2400 on the second display unit 200.

The ultrasound apparatus 1000 may receive a touch and hole gesture 2402 that touches the frequency item 2401 from among the plurality of control items by using the pointer 400 for a predetermined time period or longer. The ultrasound apparatus 1000 may select the frequency item 2401 from among the plurality of control items according to the touch and hold gesture 2402. The frequency item 2401 on the second display unit 200 may be displayed in a first display format 2403 including left and right keys and a slide bar.

When receiving the touch and hold gesture 2402 with respect to the frequency item 2401, the ultrasound apparatus 1000 may determine a second display format 2404 that is different from the first display format 2403. The second display format 2404 may include a plurality of cells. Information about the second display format 2404 corresponding to the first display format 2403 may be stored on the memory.

The ultrasound apparatus 1000 may display the frequency item 2401 on the first display unit 100 in the second display format 2404. Here, the frequency item 2401 in the second display format 2404 may partially overlap with the ultrasound image 2400. For example, the ultrasound apparatus 1000 may display the frequency item 2401 in the second display format 2404 on a region of non-interest of the ultrasound image 2400.

According to the exemplary embodiment, the ultrasound apparatus 1000 may sense a location of the pointer 400 touching the frequency item 2401 that is displayed in the first display format 2403, and may mark an indicator 2405 that indicates the location of the pointer 400 on the frequency item 2401 displayed in the second display format 2404. For example, if the location of the pointer 400 is a right side of the first display format 2403 and a frequency range represented by the right side of the first display format 2403 is 'Res' (resolution; high frequency), the ultrasound apparatus 1000 may represent a cell indicating 'Res' in the second display format 2404 in a certain color (e.g., blue color). Here, the certain color may be the indicator 2405.

Referring to FIG. 24B, when the user drags (2406) the pointer 400 within the frequency item 2401 in contact with the second display unit 200, the ultrasound apparatus 1000 may move the indicator 2405 according to the movement of the pointer 400. For example, if the user drags the pointer 400 to a left side within the frequency item 2401 displayed in the first display format 2403, the ultrasound apparatus 1000 may change a frequency range 2407 from 'Res' to 'Pen' (penetration; low frequency) and may move the indicator 2405 in the second display format 2404 to the left side. Here, the indicator 2405 may be moved from the 'Res' cell onto a 'Pen' cell 2408.

Referring to FIG. 24C, if the first display unit 100 include a touch panel, the first display unit 100 may sense a pressure applied by the user who moves the indicator 2405 on the frequency item 2401 that is displayed in the second display format 2404 on the first display unit 100. For example, the first display unit 100 may sense a touch and hold gesture 2409 that touches the 'Pen' cell 2408 included in the second display format 2404 for a predetermined time period or longer.

The ultrasound apparatus 1000 may move the indicator 2405 onto the 'Pen' cell 2408 according to the touch and hold gesture 2409 for touching the 'Pen' cell 2408 for a predetermined time period or longer, and may change the frequency range 2408 from 'Res' to 'Pen' based on the location of the indicator 2405.

Hereinafter, an operation of the ultrasound apparatus 1000 for providing an interface related to a gain value (e.g., TGC or LGC) through a plurality of display units will be described below.

Figure 25:
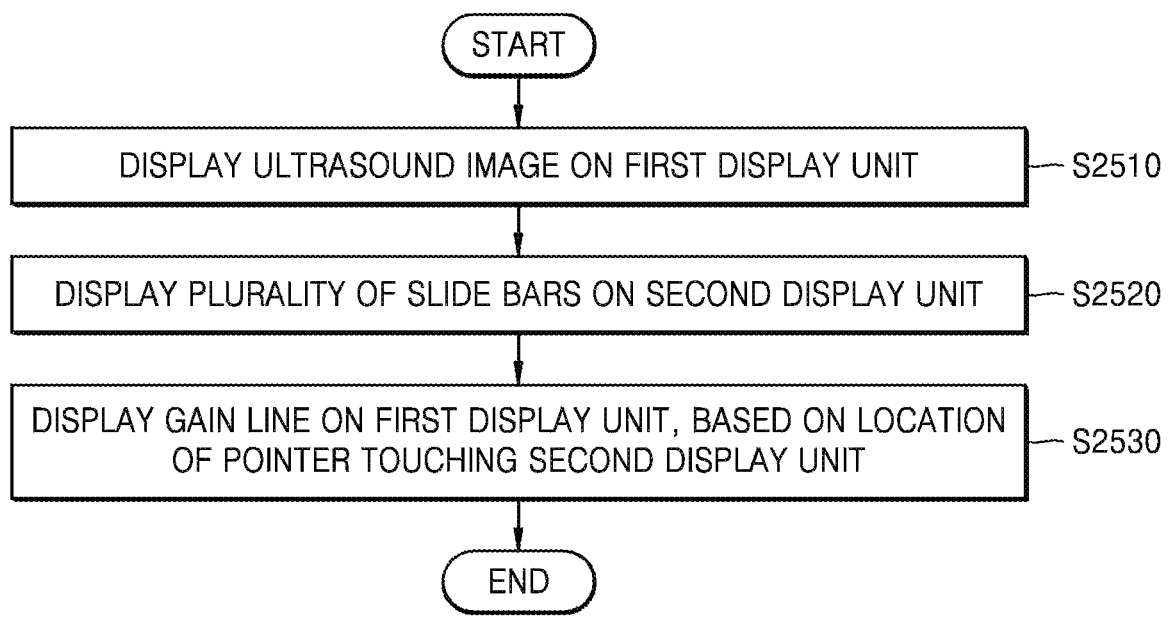
FIG. 25 is a flowchart illustrating a method for an ultrasound apparatus to provide information regarding setting of a gain value by using a plurality of display units, according to an exemplary embodiment.

FIG. 25 is a flowchart illustrating a method for the ultrasound apparatus 1000 to provide information related to setting of a gain value by using a plurality of display units.

In operation S2510, the ultrasound apparatus 1000 may display an ultrasound image on the first display unit 100.

According to the exemplary embodiment, the ultrasound apparatus 1000 may display the ultrasound images obtained via the probe 20 in real time on the first display unit 100. According to some exemplary embodiment, the ultrasound apparatus 1000 may display ultrasound images stored in a storage medium in advance on the first display unit 100.

The ultrasound image may be at least one of a B mode image, a C mode image, a D mode image, an M mode image, and an elastic mode image, but is not limited thereto. In addition, the ultrasound image according to the exemplary embodiment may be a 2D image, a 3D image, or a 4D image.

In operation S2520, the ultrasound apparatus 1000 may display a plurality of slide bars for adjusting gain values of a ultrasound echo signal on the second display unit 200. Here, the gain value may include at least one of a time gain compensation (TGC) value and a lateral gain compensation (LGC) value. The TGC value is used to compensate for a reduction in a magnitude of an ultrasound signal according to a depth of the human body. The LGC value is used to compensate for uneven attenuation amounts due to different transfer paths of ultrasound wave beams. Hereinafter, a case where the gain value is a TGC value will be described below.

According to the exemplary embodiment, a gain setting window including a plurality of slide bars for adjusting gain values corresponding to depth sections of an ultrasound image may be displayed on the second display unit 200. The gain setting window may be one of the control items displayed on the second display unit 200.

The plurality of slide bars may be arranged in parallel with each other at constant intervals therebetween along a depth direction. The number or intervals of the plurality of slide bars displayed on the second display unit 200 may be fixed or may be variable. For example, the number of the plurality of slide bars may vary depending on a kind of the probe 20 or a total depth of the ultrasound image.

For example, the ultrasound apparatus 1000 may divide the total depth of the ultrasound image into ten sections, and may display ten slide bars on the second display unit 200. Here, an uppermost slide bar from among the ten slide bars correspond to a section of the shallowest depth and a lowermost slide bar may correspond to a section of the deepest depth.

The user may drag adjustment buttons of the plurality of slide bars displayed on the second display unit 200 in a left or right direction to change the gain value of the corresponding depth section. For example, if the user moves a first adjustment button on a first slide bar to a right side, a gain value of a first depth section corresponding to the first slide bar increases, and accordingly, the ultrasound image of the first depth section may become brighter. On the contrary, if the user moves the first adjustment button on the first slide bar to a left side, a gain value of the first depth section corresponding to the first slide bar is reduced, and accordingly, the ultrasound image of the first depth section may be darkened.

The user may tap a certain location on each of the plurality of slide bars in order to change the gain value of the each depth section. For example, if the user taps a first point on the first slide bar, the ultrasound apparatus 1000 may adjust the gain value of the first depth section corresponding to the first slide bar to a first value corresponding to the first point.

According to the exemplary embodiment, the ultrasound apparatus 1000 may sense a drag input of the user in a depth direction (that is, a direction perpendicular to at least one slide bar) within the gain setting window including the plurality of slide bars. The ultrasound apparatus 1000 may change gain values corresponding respectively to the depth sections of the ultrasound image, based on a location of the drag input (e.g., coordinates of pixels on which the drag input is sensed).

For example, if the user drags his/her finger while forming a straight line or a curved line in a direction perpendicular to the plurality of slide bars in the gain setting window, the ultrasound apparatus 1000 may move the adjustment buttons to locations where the drag line and the plurality of slide bars cross each other and may set gain values corresponding to the locations of the adjustment buttons as gain values in the depth sections.

In operation S2530, the ultrasound apparatus 1000 may display a gain line on the first display unit 100 based on the location of the pointer 400 touching the second display unit 200. For example, if the pointer 400 is located in the gain setting window including the plurality of slide bars, the ultrasound apparatus 1000 may display the gain line that is obtained by connecting the gain values of the plurality of depth sections on the first display unit 100.

According to the exemplary embodiment, the ultrasound apparatus 1000 may recognize the pointer 400 touching the second display unit 200 via at least one sensor. Here, the touch may include a contact-type touch and a non contact-type touch (hovering). In addition, the ultrasound apparatus 1000 may sense the touch location of the pointer 400 via at least one sensor. The at least one sensor may be at least one of a touch sensor, a pressure sensor, a proximity sensor, an image sensor, a depth sensor, and an infrared ray sensor, but is not limited thereto.

The method for the ultrasound apparatus 1000 to sense the location of the pointer 400 is described above with reference to FIGS. 5 to 8, and thus, detailed descriptions thereof are omitted.

According to the exemplary embodiment, the ultrasound apparatus 1000 may generate a gain line by connecting the gain values corresponding to locations of the adjustment buttons in the plurality of slide bars. Here, the ultrasound apparatus 1000 may perform an interpolation calculation of gain values between the first slide bar and a second slide bar by using the gain value on the first slide bar and the gain value on the second slide bar.

According to the exemplary embodiment, if the user drags a straight line or a curved line on the gain setting window including the plurality of slide bars, the ultrasound apparatus 1000 may obtain the gain line that is obtained from the drag line.

According to the exemplary embodiment, if the pointer 400 touches the gain setting window including the plurality of slide bars, the ultrasound apparatus 1000 may display the gain line on the first display unit 100, together with the gain line. For example, the ultrasound apparatus 1000 may display the gain line on the ultrasound image or next to the ultrasound image. Here, the ultrasound apparatus 1000 may display the gain line along with depth direction of the ultrasound image.

According to the exemplary embodiment, the ultrasound apparatus 1000 may mark an indicator that indicates a depth section corresponding to the location of the pointer 400 in the gain setting window on the gain line displayed on the first display unit 100. For example, if the pointer 400 is located on the second slide bar, the ultrasound apparatus 1000 may determine a second depth value corresponding to the second slide bar and mark the indicator on a point of the gain line, which indicates the second depth value.

According to the exemplary embodiment, the ultrasound apparatus 1000 may move the indicator marked on the gain line according to the change in the location of the pointer 400 within the gain setting window including the plurality of slide bars. For example, if the pointer 400 moves downward, the ultrasound apparatus 1000 may move the indicator downward along with the gain line.

According to the exemplary embodiment, the ultrasound apparatus 1000 may receive an input for moving at least one adjustment buttons from among the adjustment buttons on the plurality of slide bars via the second display unit 200, and may change a shape of the gain line displayed on the first display unit 100 based on the location of the at least one adjustment button that has moved.

The ultrasound apparatus 1000 according to the exemplary embodiment displays the gain line corresponding to the gain values set by the user on the second display unit 200, on the first display unit 100 together with the ultrasound image, and thus, the user may intuitively identify the shape of the gain line, an inclination of the gain line, the gain values (e.g., TGC values), etc., without moving his/her eyes.

Figure 26A:
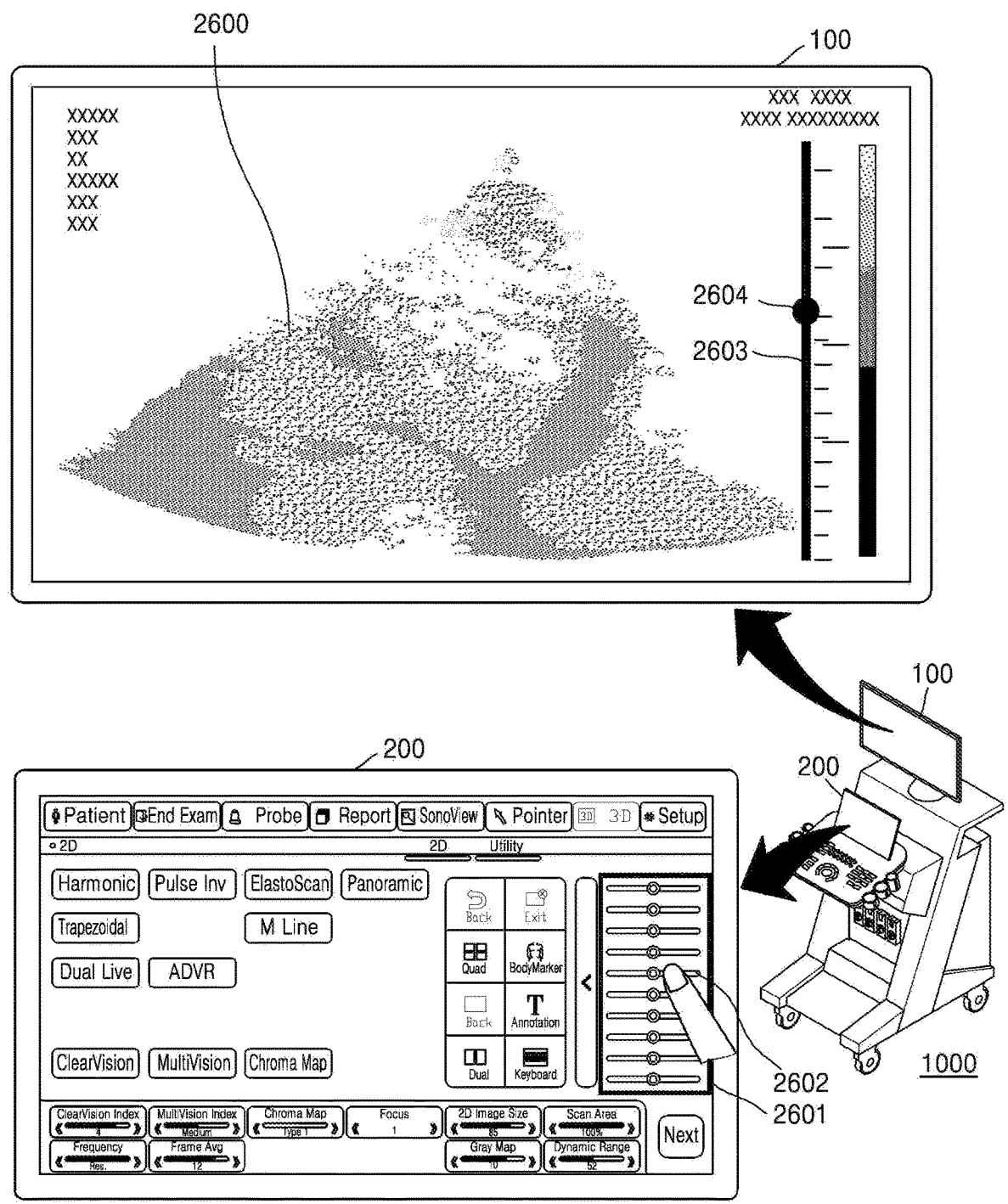
FIGS. 26A and 26B are diagrams illustrating an example, in which an ultrasound apparatus provides a gain setting window on a touch screen and displays a gain line on a main screen, according to an exemplary embodiment.
Figure 26B:
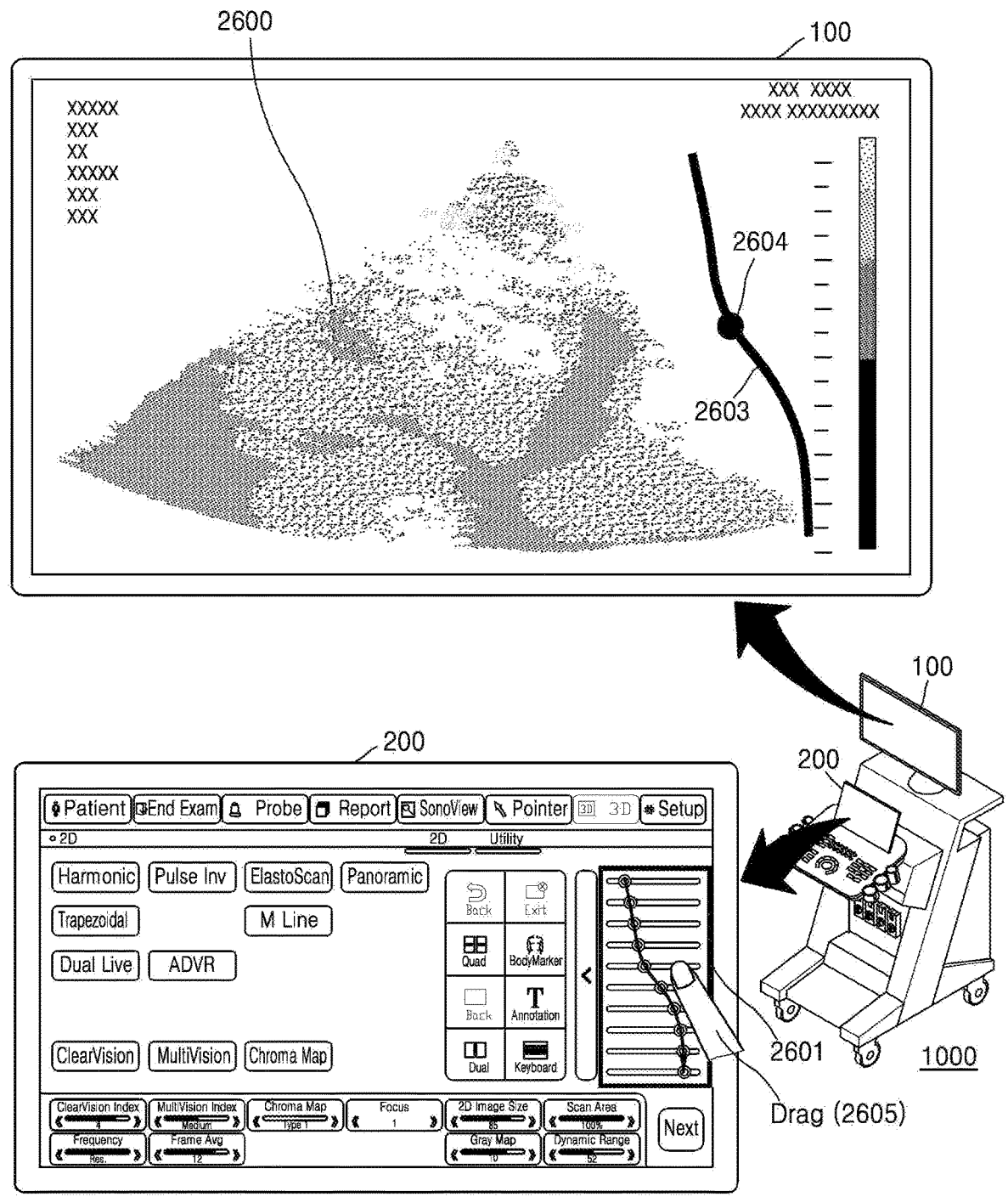

FIGS. 26A and 26B are diagrams illustrating an example, in which the ultrasound apparatus 1000 provides the gain setting window on the touch screen and displays the gain line on the main screen.

Referring to FIG. 26A, the ultrasound apparatus 1000 may display an ultrasound image 2600 on the first display unit 100, and may display a plurality of control items related to the ultrasound image 2600 on the second display unit 200.

The ultrasound apparatus 1000 may receive a touch and hold gesture that touches a first region, in which a gain control item 2601 from among the plurality of control items is displayed, by using the pointer 400 for a predetermined time period or longer. The ultrasound apparatus 1000 may select the gain control item 2601 from among the plurality of control items, according to the touch and hold gesture. Here, the ultrasound apparatus 1000 may generate a gain line 2603 by connecting gain values corresponding respectively to a plurality of slide bars included in the gain control item 2601. For example, since the adjustment buttons on the plurality of slide bars are located at center portions, the ultrasound apparatus 1000 may generate the gain line 2603 as a straight line.

The ultrasound apparatus 1000 may display the generated gain line 2603 on the first display unit 100. For example, the ultrasound apparatus 1000 may display the gain lien 2603 next to the ultrasound image 2600.

Then, the ultrasound apparatus 1000 may mark an indicator 2604 that indicates the location of the pointer 400 in the gain control item 2601 on the gain line 2603. For example, if the pointer 400 is located on a fifth slide bar 2602, the ultrasound apparatus 1000 determines a fifth depth value corresponding to the fifth slide bar 2602 and mark the indicator 2604 at a first point representing the fifth depth value on the gain line 2603.

According to the exemplary embodiment, if the location of the pointer 400 is changed within the gain control item 2601, the ultrasound apparatus 1000 may move the indicator 2604 marked on the gain line 2603. For example, if the pointer 400 moves from the fifth slide bar 2602 onto a sixth slide bar, the ultrasound apparatus 1000 may determine a sixth depth value corresponding to the sixth slide bar and may move the indicator 2604 from the first point representing the fifth depth value to a second point representing the sixth depth value on the gain line 2603.

Therefore, the user may recognize where the pointer 400 on the second display unit 200 currently touches through the indicator 2604 on the gain line 2603, without moving his/her eyes from the first display unit 100 to the second display unit 200.

Referring to FIG. 26B, the ultrasound apparatus 1000 may receive an input for setting gain values respectively corresponding to the plurality of depth sections when the user moves the locations of the adjustment buttons on the plurality of slide bars. For example, the ultrasound apparatus 1000 may receive a drag gesture 2605 of the user dragging his/her finger while forming a curved line in a direction perpendicular to the plurality of slide bars in the gain control item 2601. The ultrasound apparatus 1000 may move the adjustment buttons to points where the drag line and the plurality of slide bars cross each other according to the drag gesture 2605, and sets gain values corresponding to the locations of the adjustment buttons as the gain values in the respective depth sections.

In addition, the ultrasound apparatus 1000 may also change the shape of the gain line 2603 when the locations of the adjustment buttons are changed. For example, the ultrasound apparatus 1000 may change the shape of the gain line 2603 along with the drag line.

The ultrasound apparatus 1000 may apply the gain values corresponding to the locations of the adjustment buttons to an ultrasound echo signal. In this case, brightness of each of the depth sections in the ultrasound image 2600 may be changed.

Figure 27:
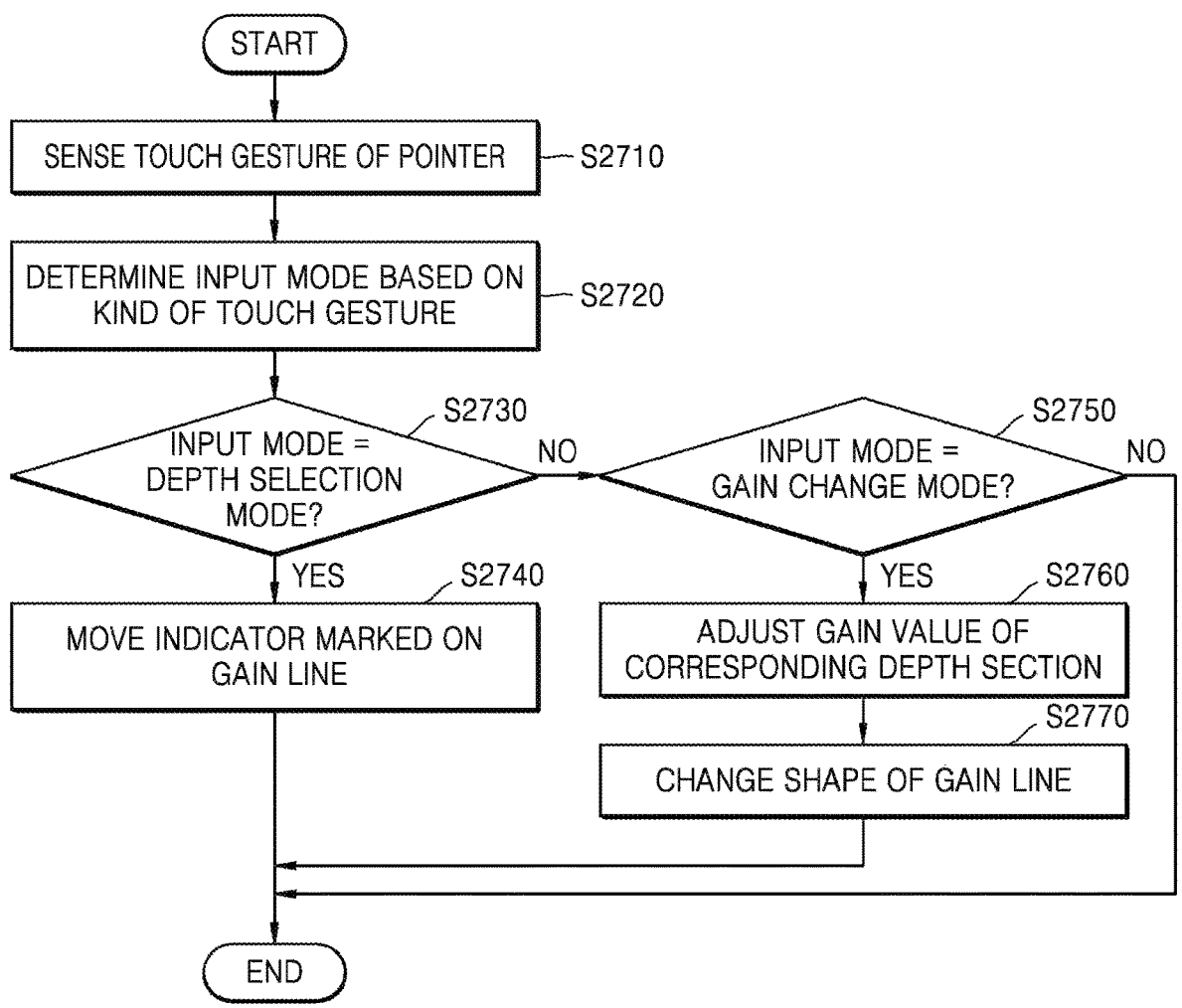
FIG. 27 is a flowchart illustrating a method for an ultrasound apparatus to determine an input mode based on a kind of a touch gesture, according to an exemplary embodiment.

FIG. 27 is a flowchart illustrating a method for the ultrasound apparatus 1000 to determine an input mode according to a kind of the touch gesture.

In operation S2710, the ultrasound apparatus 1000 may sense a touch gesture of the pointer 400 onto the second display unit 200.

According to the exemplary embodiment, the ultrasound apparatus 1000 may recognize the pointer 400 touching the second display unit 200 via at least one sensor. Here, the touch may include a contact-type touch and a non contact-type touch (hovering). The at least one sensor may be at least one of a touch sensor, a pressure sensor, a proximity sensor, an image sensor, a depth sensor, and an infrared ray sensor, but is not limited thereto.

According to the exemplary embodiment, the ultrasound apparatus 1000 may identify the kind of the touch gesture on the second display unit 200 via at least one sensor. The touch gesture may include a one-finger gesture, a multi-finger gesture, a tap gesture, a touch and hold gesture, a touch and drag gesture, a flick gesture, a swipe gesture, a hovering gesture, etc., but is not limited thereto.

The method for the ultrasound apparatus 1000 to sense the location of the pointer 400 is described above with reference to FIGS. 5 to 8, and thus, detailed descriptions thereof are omitted.

In operation S2720, the ultrasound apparatus 1000 may determine an input mode based on the kind of the touch gesture of the pointer 400 sensed on the second display unit 200.

According to the exemplary embodiment, the input mode may include a depth selection mode for selecting one depth section from among the depth sections of the ultrasound image and a gain change mode for changing the gain value.

For example, if the touch gesture of the pointer 400 is the one-finger gesture, the ultrasound apparatus 1000 may determine the input mode as the depth selection mode, and if the touch gesture of the pointer 400 is the multi-finger gesture, the ultrasound apparatus 1000 may determine the input mode as the gain change mode. On the contrary, if the touch gesture of the pointer 400 is the one-finger gesture, the ultrasound apparatus 1000 may determine the input mode as the gain change mode, and if the touch gesture of the pointer 400 is the multi-finger gesture, the ultrasound apparatus may determine the input mode as the depth selection mode.

Otherwise, if the touch gesture is the hovering gesture, the ultrasound apparatus 1000 may determine the input mode as the depth selection mode, and if the touch gesture is the touch and drag gesture, the ultrasound apparatus 1000 may determine the input mode as the gain change mode.

In operations S2730 and S2740, when the input mode is determined as the depth selection mode, the ultrasound apparatus 1000 may move the indicator marked on the gain line according to the touch gesture.

For example, when receiving a first drag gesture that the user drags his/her finger in up and down directions in contact with the gain setting window in which the plurality of slide bars are displayed, the ultrasound apparatus 1000 may determine the input mode as the depth selection mode. Here, the ultrasound apparatus 1000 may select a certain depth section from among the plurality of depth sections or may change the selected depth section according to the first drag gesture. The ultrasound apparatus 1000 may mark an indicator on a location representing the certain depth section selected by the first drag gesture. Therefore, if the user drags his/her one finger in the up and down directions within the gain setting window, the ultrasound apparatus 1000 may move the indicator in the up and down direction on the gain line displayed on the first display unit 100 according to the first drag gesture.

In operations S2750 and S2760, when the input mode is determined as the gain change mode, the ultrasound apparatus 1000 may adjust the gain value of the depth section according to the touch gesture.

For example, when receiving a second drag gesture that the user drags his/her two or more fingers in left and right directions in contact with the gain setting window in which the plurality of slide bars are displayed, the ultrasound apparatus 1000 may determine the input mode as the gain change mode. In addition, the ultrasound apparatus 1000 may adjust the gain value in a certain depth section according to the second drag gesture.

In operation S2770, when the gain value of a certain depth section is adjusted in the gain change mode, the ultrasound apparatus 1000 may change the shape of the gain line displayed on the first display unit 100 according to the adjusted gain value.

Hereinafter, an operation of the ultrasound apparatus 1000 for providing an input mode that is different according to the kind of the touch gesture will be described below with reference to FIGS. 28A to 29C. FIGS. 28A to 29C illustrates a case in which the one-finger gesture corresponds to the depth selection mode and the multi-finger gesture corresponds to the gain change mode as an example.

Figure 28A:
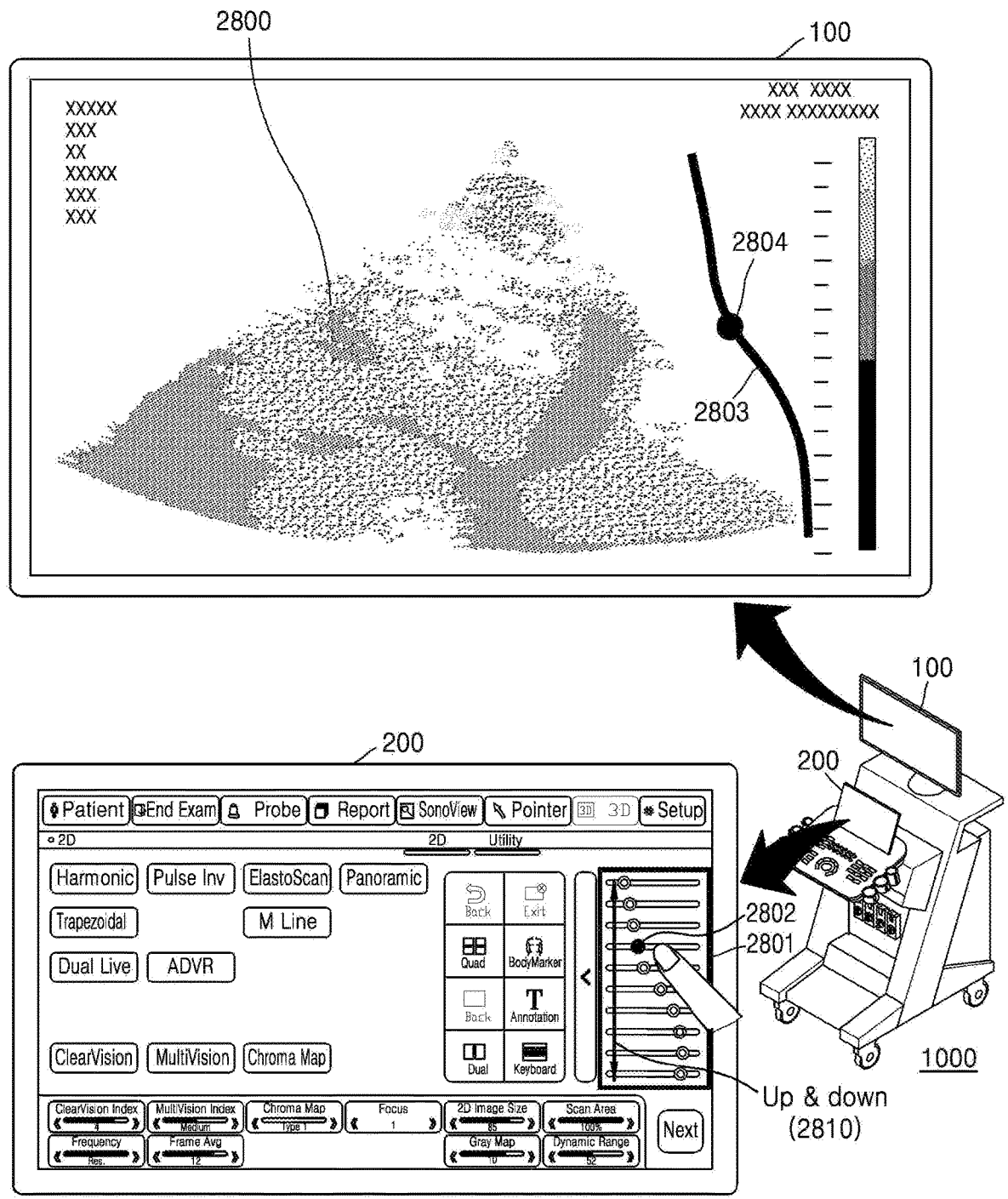
FIGS. 28A and 28B are diagrams of a depth selection mode according to an exemplary embodiment.
Figure 28B:
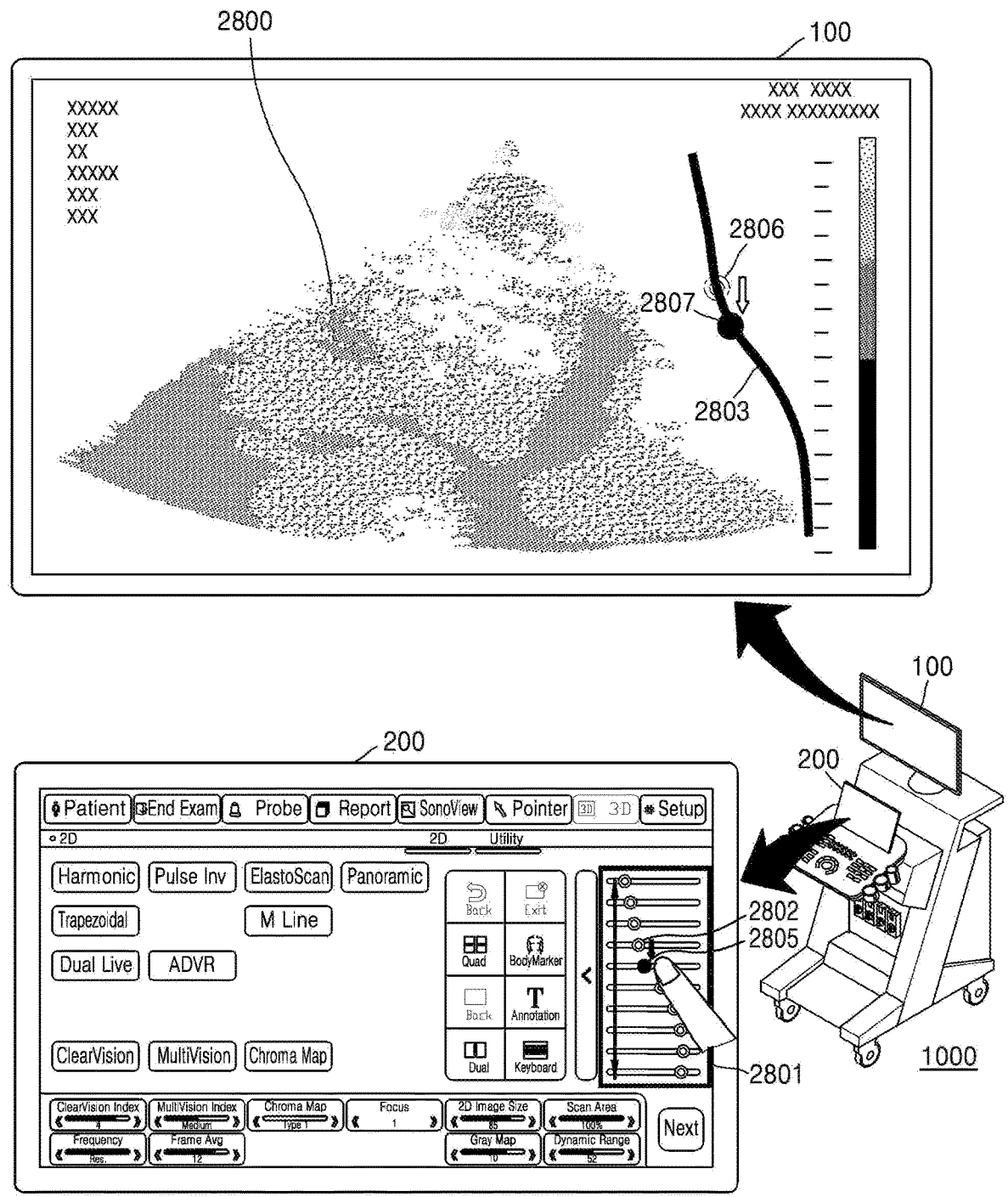

FIGS. 28A and 28B are diagrams illustrating the depth selection mode according to an exemplary embodiment.

Referring to FIG. 28A, the ultrasound apparatus 1000 may display an ultrasound image 2800 on the first display unit 100 and may display a plurality of control items related to the ultrasound image 2800 on the second display unit 200.

The ultrasound apparatus 1000 may receive a touch and hold gesture that touches a first region on which a gain control item 2801 from among the plurality of control items is displayed by using the pointer 400 for a predetermined time period or longer. The ultrasound apparatus 1000 may select the gain control item 2801 from among the plurality of control items, according to the touch and hold gesture with respect to the first region. Here, the ultrasound apparatus 1000 may display a gain line 2803 that is formed by connecting gain values corresponding respectively to the plurality of slide bars included in the gain control item 2801, on the first display unit 100. For example, the ultrasound apparatus 1000 may display the gain line 2803 that is a curved line connecting the adjustment buttons on the plurality of slide bars, next to the ultrasound image 2800.

In addition, the ultrasound apparatus 1000 may mark an indicator 2804 representing a location of the pointer 400 in the gain control item 2801, on the gain line 2803. For example, if the pointer 400 is located on a fourth slide bar 2802, the ultrasound apparatus 1000 may determine a fourth depth value corresponding to the fourth slide bar 2802 and may mark the indicator 2804 at a location representing the fourth depth value on the gain line 2803.

In FIG. 28A, the indicator 2804 has a circular shape as an example, but is not limited thereto. That is, the indicator 2804 may have various shapes.

When receiving a one-finger gesture 2810 that the user drags one finger (e.g., an forefinger) in an upper direction or a lower direction in the gain control item 2810, the ultrasound apparatus 1000 may determine the input mode as the depth selection mode and may change the selection of the depth section according to the one-finger gesture. Here, the one-finger gesture may not affect the gain value.

Referring to FIG. 28B, the ultrasound apparatus 1000 may select a certain depth section from among the depth sections.

For example, if the pointer 400 moves from the fourth slide bar 2802 onto the fifth slide bar according to the one finger gesture 2810 that drags one finger (e.g., the forefinger) downward, the ultrasound apparatus 1000 may select a fifth depth section corresponding to the fifth slide bar, instead of a fourth depth section corresponding to the fourth slide bar.

Here, the ultrasound apparatus 1000 may move the indicator 2804 from a first point 2806 representing the fourth depth section to a second point 2807 representing the fifth depth section on the gain line 2603.

Therefore, the user may recognize the depth section that the pointer 400 on the second display unit 200 currently touches from the indicator 2804 on the gain line 2803, without turning his/her eyes from the first display unit 100 to the second display unit 200. In addition, the user may drag his/her one finger upward or downward on the second display unit 200 so as to move the indicator 2804 to a certain depth section, the gain value of which is wanted to be adjusted.

Figure 29A:
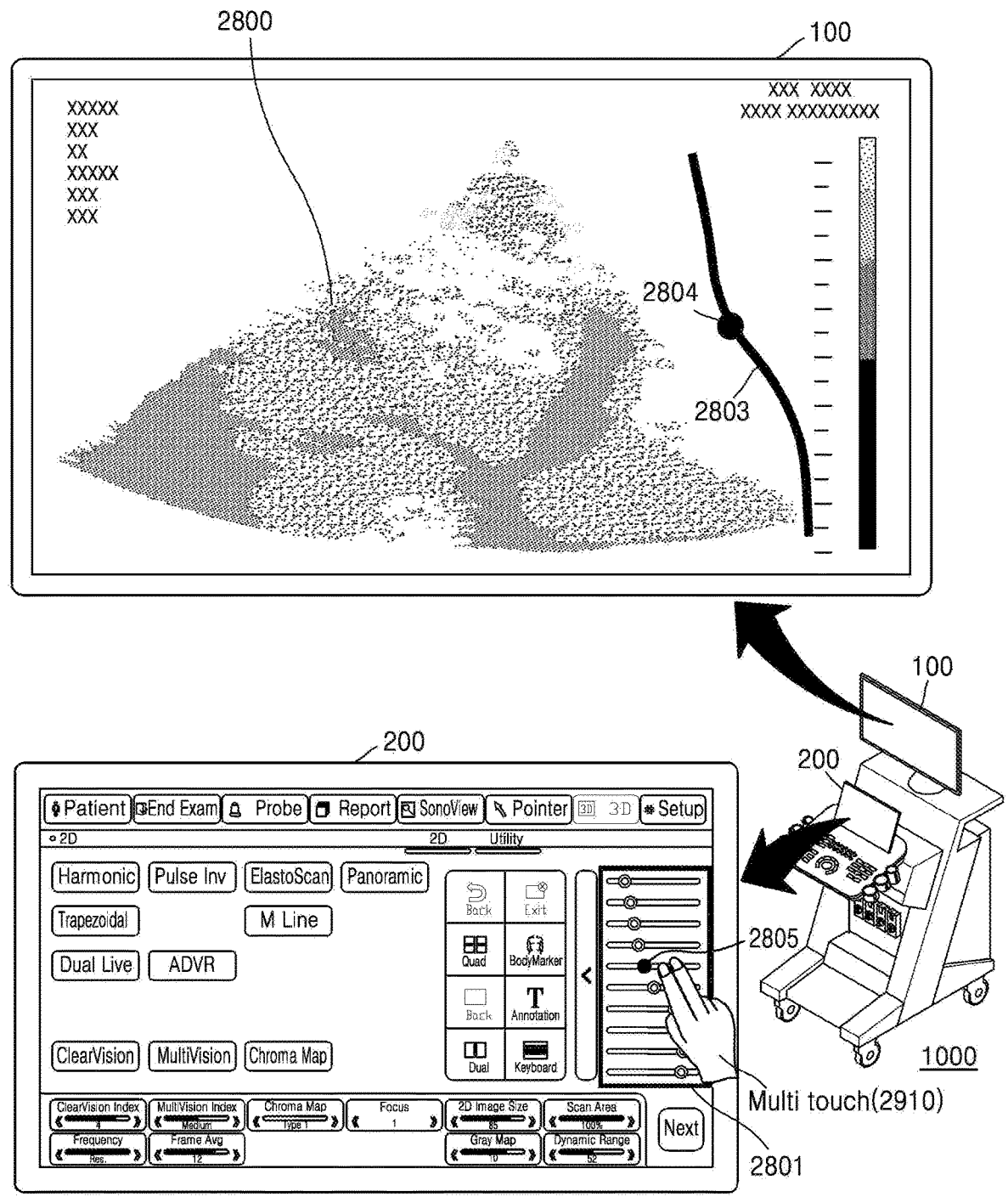
FIGS. 29A to 29C are diagrams of a gain change mode according to an exemplary embodiment.
Figure 29B:
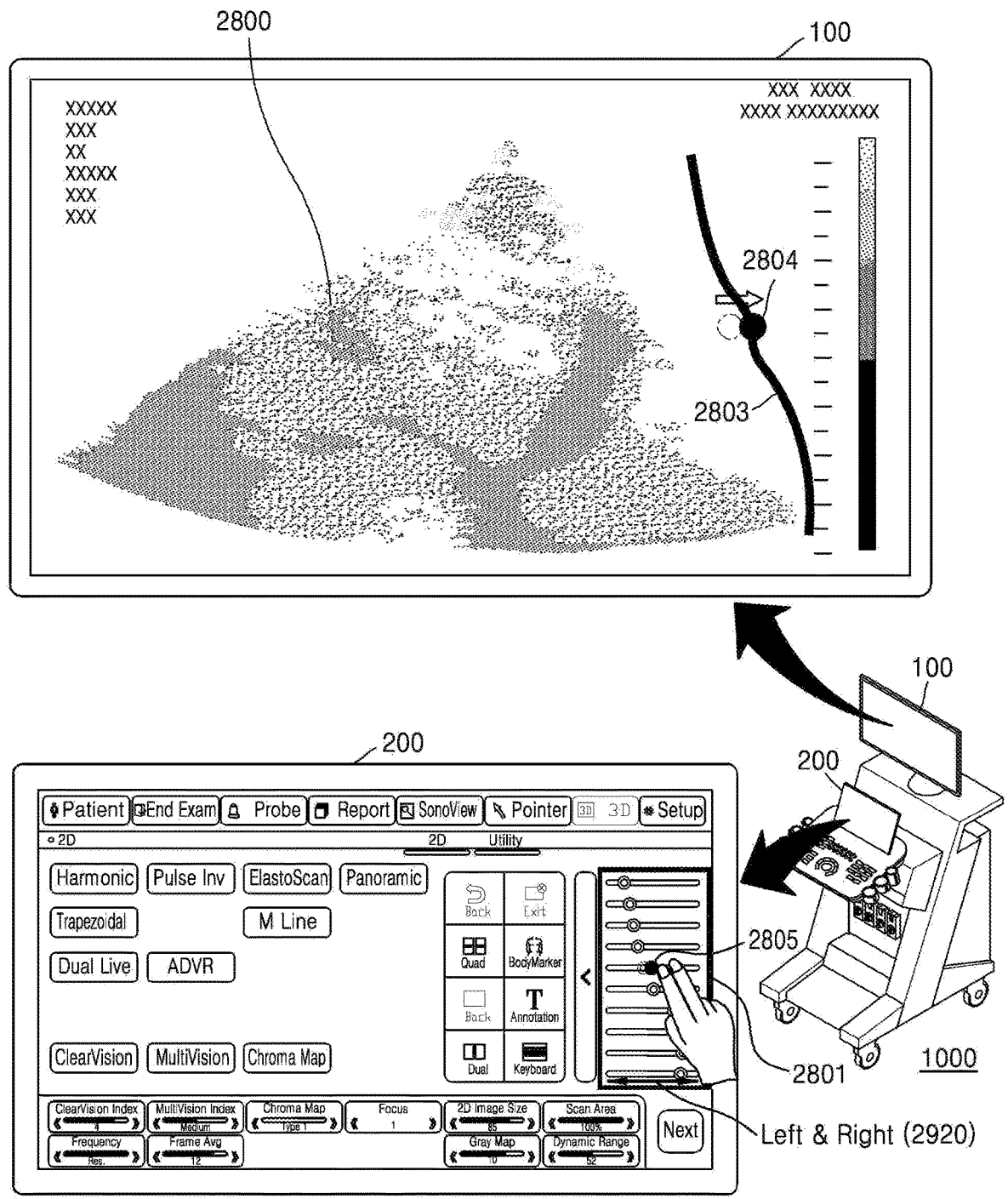
Figure 29C:
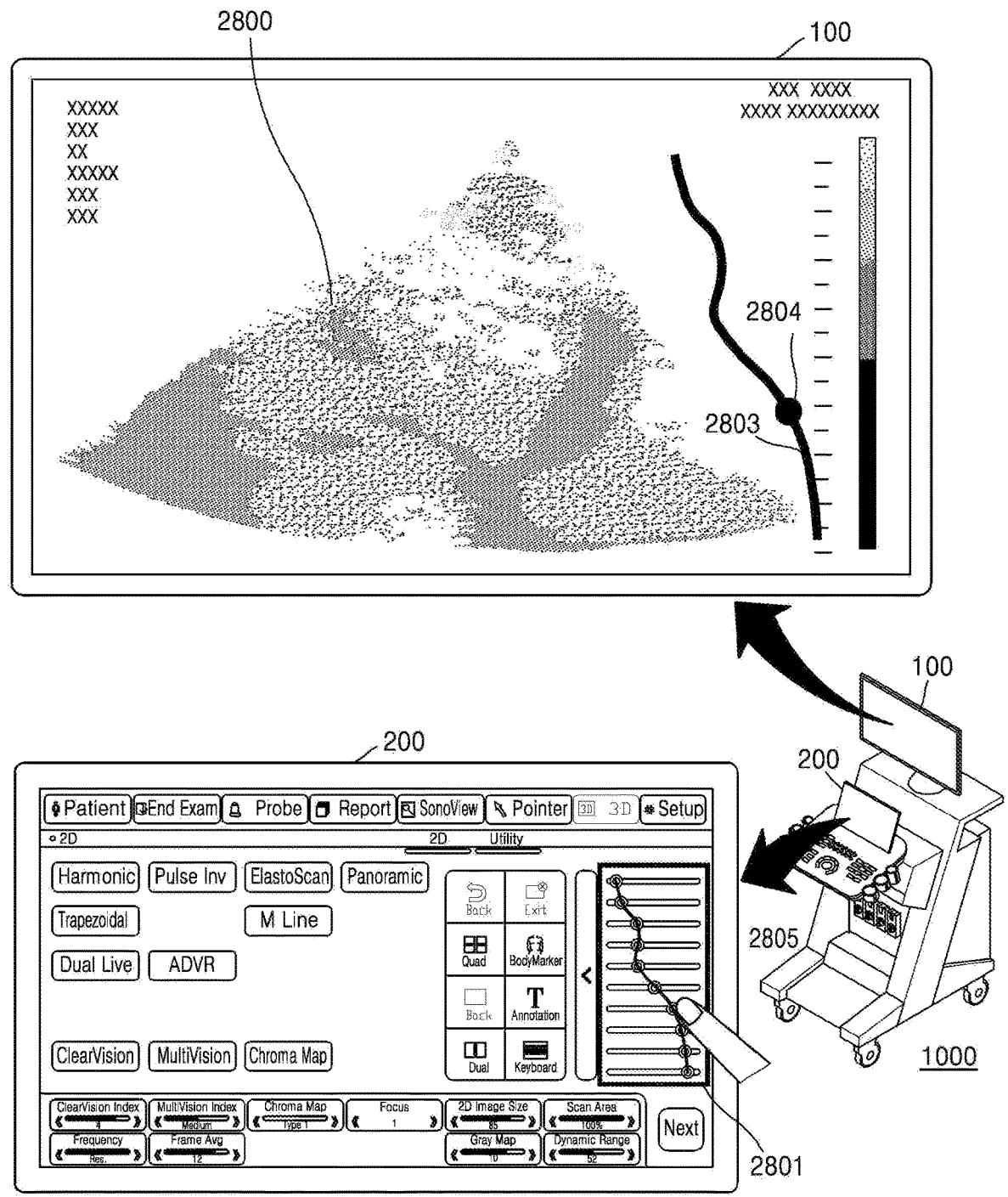

FIGS. 29A to 29C are diagrams illustrating a gain change mode according to an exemplary embodiment.

Referring to FIG. 29A, if the user wants to adjust the gain value of the fifth depth section, the user may drag his/her forefinger upward or downward within the gain control item 2801 and may further place his/her middle finger on the gain control item 2801 in a state where the indicator 2804 is located at the second point 2807 representing the fifth depth section.

In this case, the ultrasound apparatus 1000 may sense the above gesture as a multi-finger gesture 2910 that denotes touch of two or more fingers, and may change the input mode from the depth selection mode to the gain change mode.

Referring to FIG. 29B, the ultrasound apparatus 1000 may receive a gesture 2920 of the user, that is, dragging his/her two fingers to left or right side in contact with the gain control item 2801. For example, the ultrasound apparatus 1000 may receive an input that the user drags his/her two fingers (forefinger and middle finger) to the right side. In this case, the ultrasound apparatus 1000 may increase the gain value at the fifth depth section from a first gain value to a second gain value, and the adjustment button on the fifth slide bar corresponding to the fifth depth section may be moved to the right side.

Since the gain value of the fifth depth section is changed from the first gain value to the second gain value, the ultrasound apparatus 1000 may change the shape of the gain line displayed on the first display unit 100 based on the second gain value. In addition, the ultrasound apparatus 1000 may apply the second gain value of the fifth depth section to the ultrasound echo signal. Therefore, the ultrasound image at the fifth depth section may become brighter.

Referring to FIG. 29C, if the user takes his/her middle finger off the second display unit 200 so as to touch the second display unit 200 only by his/her forefinger, the ultrasound apparatus 1000 may switch the input mode from the gain change mode to the depth selection mode.

Here, the user may drag his/her forefinger upward or downward to select a certain depth section, the gain value of which is wanted to be adjusted. When the indicator 2804 is located at the certain depth section that the user wants to adjust the gain value, the user may place his/her middle finger again on the second display unit 200. In this case, the ultrasound apparatus 1000 may switch the input mode from the depth selection mode to the gain change mode. The user may his/her two fingers to left or right side to change the gain value of the certain depth section.

Therefore, according to the exemplary embodiment, the user may change the gain value of a certain depth section by repeatedly using the one-finger gesture and the multi-finger gesture without watching the second display unit 200, and the changed gain value may be identified in real time through the first display unit 100.

FIG. 30 is a diagram illustrating an example, in which the ultrasound apparatus 1000 determines an input mode related to the TGC based on a kind of the touch gesture. In FIG. 30, a case where the multi-finger gesture corresponds to the depth selection mode and the one-finger gesture corresponds to the gain change mode will be described as an example.

Referring to 3010 of FIG. 30, the ultrasound apparatus 1000 may receive a drag gesture forming a curved line in a direction perpendicular to the plurality of slide bars within a gain control item 3000 for adjusting the TGC value. The ultrasound apparatus 1000 may move the adjustment buttons to locations where the dragged line and the plurality of slide bars cross each other according to the drag gesture, and may set gain values corresponding to the locations of the adjustment buttons as gain values in respective depth sections.

In addition, the ultrasound apparatus 1000 may generate a gain line by connecting the gain values represented by the adjustment values, and may display the gain line on the first display unit 100. For example, the ultrasound apparatus 1000 may display the gain line formed as the dragged curved line on the first display unit 100.

In addition, the ultrasound apparatus 1000 may apply the gain values corresponding to the locations of the adjustment buttons to the ultrasound echo signal. In this case, the brightness of the ultrasound image with respect to the depth sections may be adjusted.

According to 3020 of FIG. 30, the ultrasound apparatus 1000 may receive a multi-finger gesture touching the gain control item 3000 on the second display unit 200 by using user's two fingers (e.g., forefinger and middle finger). In this case, the ultrasound apparatus 1000 may set the input mode as the depth selection mode.

Referring to 3030 of FIG. 30, the user may select a certain depth section that the user wants to adjust the gain value by dragging two fingers upward or downward. For example, if the user drags his/her two fingers from the fourth slide bar onto the fifth slide bar, the ultrasound apparatus 1000 may select the fifth depth section instead of the fourth depth section.

Here, the ultrasound apparatus 1000 may move an indicator from a first point representing the fourth depth section to a second point representing the fifth depth section on the gain line.

Referring to 3040 of FIG. 30, if the user takes his/her middle finger off the second display unit 200 and touches the second display unit 200 only by the forefinger, the ultrasound apparatus 1000 may switch the input mode from the depth selection mode to the gain change mode.

Referring to 3050 of FIG. 30, the ultrasound apparatus 1000 may receive a gesture that the user drags his/her forefinger in the left or right direction in contact with the gain control item 300. For example, the ultrasound apparatus 1000 may receive an input that the user drags his/her forefinger to the right side. In this case, the ultrasound apparatus 1000 may increase the gain value in the fifth depth section from the first gain value to the second gain value based on a dragged distance, and the adjustment button on the fifth slide bar corresponding to the fifth depth section may be moved to the right side.

Since the gain value of the fifth depth section is changed from the first gain value to the second gain value, the ultrasound apparatus 1000 may change the shape of the gain line displayed on the first display unit 100 based on the second gain value. The ultrasound apparatus 1000 may apply the second gain value of the fifth depth section to the ultrasound echo signal. Therefore, the ultrasound image of the fifth depth section may be brighter than before.

Referring to 3060 of FIG. 30, if the user places his/her middle finger on the second display unit 200 again and touches the second display unit 200 by the forefinger and the middle finger, the ultrasound apparatus 1000 may switch the input mode from the gain change mode to the depth selection mode.

Here, the user may select again a certain depth section that the user wants to adjust the gain value by dragging the forefinger and the middle finger upward or downward. When the indicator is located at the depth section, the gain value of which is to be adjusted, the user takes the middle finger off the second display unit 200. In this case, the ultrasound apparatus 1000 may switch the input mode from the depth selection mode to the gain change mode, again. The user may change the gain value in the selected depth section by dragging his/her one finger (forefinger) in the left or right direction.

Therefore, according to the exemplary embodiment, the user may change the gain value in a certain depth section by repeatedly using the one-finger gesture and the multi-finger gesture without seeing the second display unit 200, and may identify the changed gain value in real time via the first display unit 100.

Figure 31:
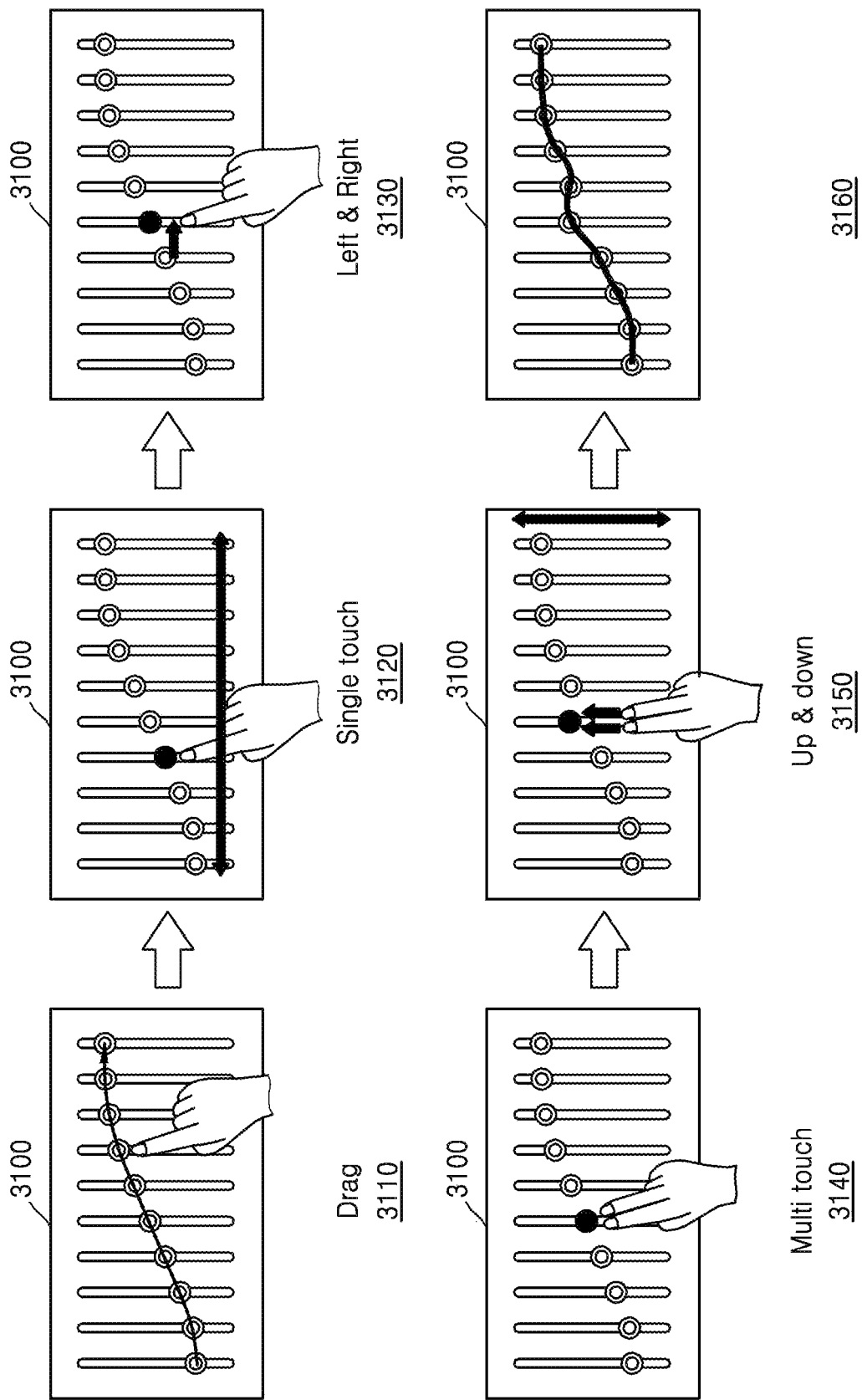
FIG. 31 is a diagram illustrating an example, in which an ultrasound apparatus determines an input mode related to an LGC based on a kind of a touch gesture, according to an exemplary embodiment.

FIG. 31 is a diagram illustrating an example, in which the ultrasound apparatus 1000 determines an input mode related to the LGC based on a kind of the touch gesture. In FIG. 31, a case where the one-finger gesture corresponds to a scan line selection mode and the multi-finger gesture corresponds to a gain change mode will be described as an example.

Referring to 3110 of FIG. 31, the ultrasound apparatus 1000 may receive a drag gesture forming a curved line in a direction perpendicular to a plurality of slide bars within a gain control item 3100 for adjusting the LGC value. The ultrasound apparatus 1000 may move adjustment buttons to locations where the dragged line and the plurality of slide bars cross each other according to the drag gesture, and may set gain values corresponding to the locations of the adjustment buttons as gain values in respective scan line sections.

In addition, the ultrasound apparatus 1000 may generate a gain line by connecting the gain values represented by the adjustment buttons, and may display the gain line on the first display unit 100. For example, the ultrasound apparatus 1000 may display the gain line formed as the dragged line in a transverse direction under the ultrasound image displayed on the first display unit 100.

The ultrasound apparatus 1000 may apply the gain values corresponding to the locations of the adjustment buttons to the ultrasound echo signal. In this case, brightness of the ultrasound image by scan line sections may be changed.

Referring to 3120 of FIG. 31, the ultrasound apparatus 1000 may receive a one-finger gesture touching the gain control item 3100 on the second display unit 200 by user's one finger (e.g., forefinger). In this case, the ultrasound apparatus 1000 may set the input mode as the scan line selection mode.

Referring to 3130 of FIG. 31, the user may select a certain scan line section by dragging one finger (forefinger) on the gain control item 3100. For example, if the user drags his/her forefinger from a fourth slide bar onto a fifth slide bar, the ultrasound apparatus 1000 may select a fifth scan line section instead of a fourth scan line section.

Here, the ultrasound apparatus 1000 may move an indicator on the gain line from a first point representing the fourth scan line section to a second point representing the fifth scan line section.

Referring to 3140 of FIG. 31, if the user places his/her middle finger within the gain control item 3100, the ultrasound apparatus 1000 may sense it as a multi-finger gesture 2910 and may change the input mode from the scan line selection mode to the gain change mode.

Referring to 3150 of FIG. 31, the ultrasound apparatus 1000 may receive a gesture that the user drags his/her two fingers (forefinger and middle finger) upward or downward in contact with the gain control item 3100. For example, the ultrasound apparatus 1000 may receive an input dragging user's two fingers upward at the same time. In this case, the ultrasound apparatus 1000 may change a gain value of the fifth scan line section from the first gain value to the second gain value based on the dragged distance, and the adjustment button on the fifth slide bar corresponding to the fifth depth section may be moved upward.

Since the gain value in the fifth scan line section is changed from the first gain value to the second gain value, the ultrasound apparatus 1000 may change a shape of the gain line displayed on the first display unit 100 based on the second gain value. The ultrasound apparatus 1000 may apply the second gain value in the fifth scan line section to the ultrasound echo signal.

Referring to 3160 of FIG. 31, when the user takes his/her middle finger off the gain control item 3100 and touches the gain control item 3100 only by the foreigner, the ultrasound apparatus 1000 may switch the input mode from the gain change mode to the scan line selection mode.

Here, the user may select a certain scan line section, a gain value of which is wanted to be adjusted, by dragging his/her forefinger in the left or right direction. When the indicator is located at the certain scan line section that the user wants to adjust the gain value, the user may place his/her middle finger gain on the second display unit 200. In this case, the ultrasound apparatus 1000 may switch the input mode from the scan line selection mode to the gain change mode again.

The user may change the gain value in the certain scan line section by dragging two fingers (forefinger and middle finger) upward or downward.

Therefore, according to the exemplary embodiment, the user may change the gain value (LGC value) in the scan line section by repeatedly using the one-finger gesture and the multi-finger gesture without seeing the second display unit 200, and may identify the changed gain value in real time via the first display unit 100.

Figure 32:
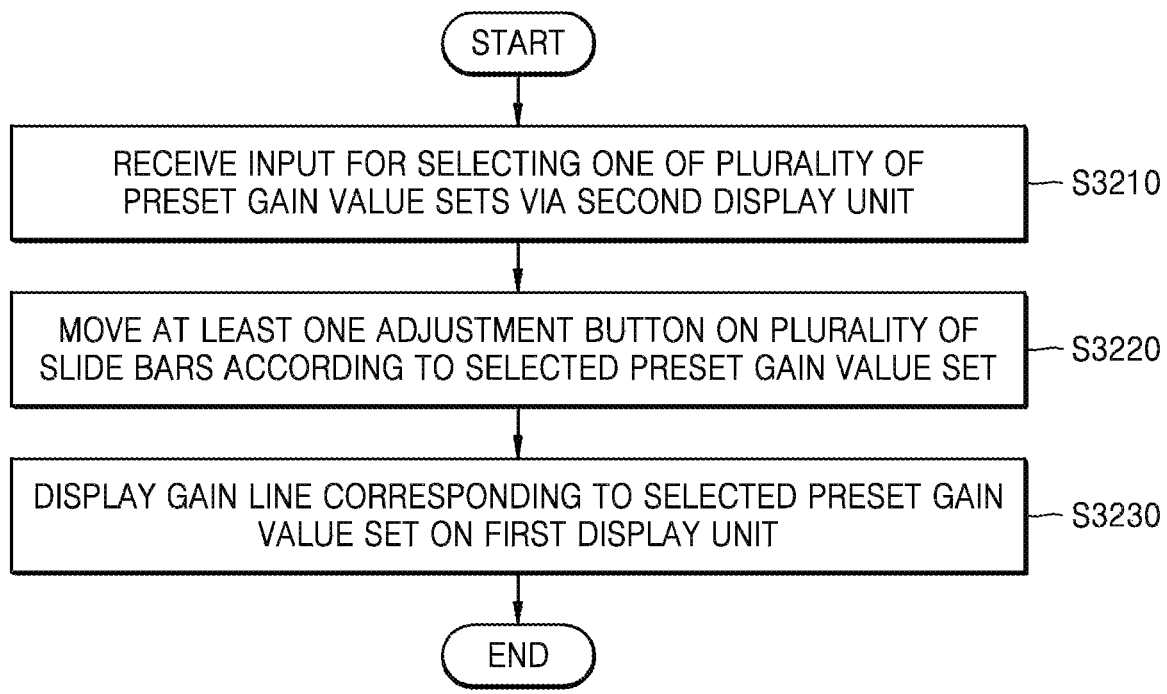
FIG. 32 is a flowchart illustrating a method for an ultrasound apparatus to provide a gain line corresponding to a predetermined gain value set, according to an exemplary embodiment.

FIG. 32 is a flowchart illustrating a method for the ultrasound apparatus 1000 to provide a gain line corresponding to a preset gain value set.

In operation S3210, the ultrasound apparatus 1000 may receive an input for selecting one of a plurality of preset gain value sets, via the second display unit 200. The plurality of preset gain value sets may include a gain value set that is set by the ultrasound apparatus 1000 in advance (e.g., a typical gain value set that is frequently used) and a preset gain value set that is set by the user, but is not limited thereto.

According to the exemplary embodiment, the ultrasound apparatus 1000 may display a plurality of icons representing the plurality of preset gain value sets, and may receive an input for selecting one of the plurality of icons. For example, the ultrasound apparatus 1000 may receive a gesture for touching a first icon that indicates a first gain value set from among the plurality of icons.

The icon indicating the preset gain value set may include a gain line obtained by connecting gain values corresponding to a plurality of depth sections. Here, the gain line may be variously represented as a solid line, a dashed line, a dashed and dotted line, etc. In addition, the icon indicating the gain value set may be represented as an image including a plurality of slide bars.

In operation S3220, the ultrasound apparatus 1000 may move at least one adjustment button on the plurality of slide bars according to the gain value set that is selected.

The preset gain value set may include the gain values corresponding to the plurality of depth sections. Therefore, the ultrasound apparatus 1000 may extract the gain values corresponding to the plurality of depth sections included in the selected preset gain value set. In addition, the ultrasound apparatus 1000 may move the adjustment buttons on the plurality of slide bars matched respectively with the plurality of depth sections, based on the extracted gain values.

In operation S3230, the ultrasound apparatus 1000 may display the gain line corresponding to the selected preset gain value set on the first display unit 100. For example, the ultrasound apparatus 1000 may generate a gain line by connecting the gain values included in the selected gain value set, and may display the gain line on the first display unit 100.

According to the exemplary embodiment, the ultrasound apparatus 1000 may apply the gain values corresponding to the plurality of depth sections included in the selected preset gain value set to the ultrasound echo signal. As such, the brightness of the ultrasound image on the first display apparatus 100 by the depth sections may be changed.

Figure 33A:
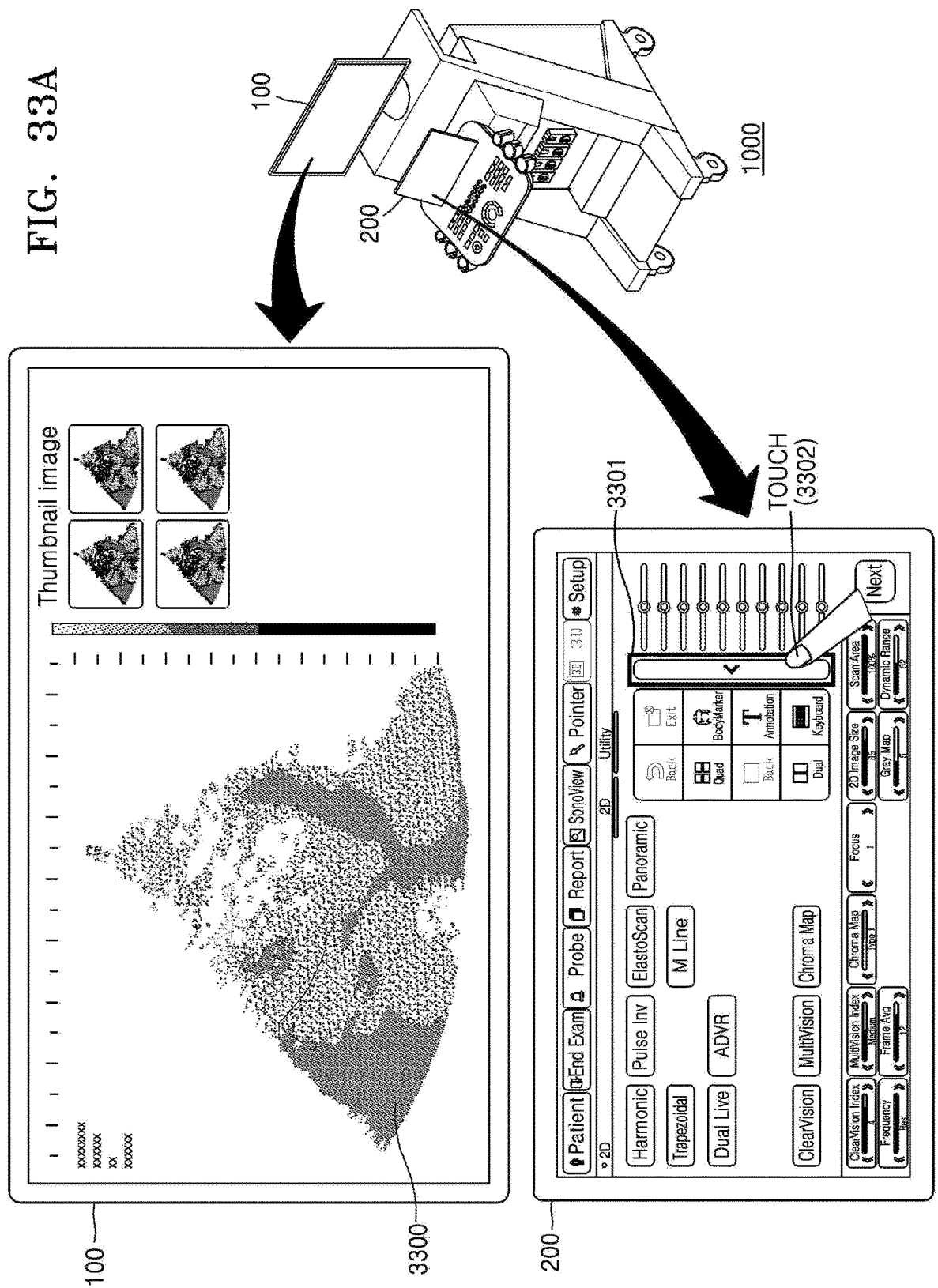

FIGS. 33A to 33C are diagrams illustrating an example of providing information about the preset gain value set and selected by the user.

Referring to FIG. 33A, the ultrasound apparatus 1000 displays an ultrasound image 3300 on the first display unit 100 and may display a plurality of control items related to the ultrasound image 3300 on the second display unit 200. The ultrasound apparatus 1000 may receive a gesture 3302 touching a preset button 3301 from among the plurality of control items by the pointer 400 for a predetermined time period or longer.

Referring to FIG. 33B, in response to the gesture 3302 touching the preset button 3301, the ultrasound apparatus 1000 may display a list 3303 of a plurality of preset gain value sets on the second display unit 200. The list 3303 may include icons corresponding respectively to the plurality of gain value sets.

When receiving the pointer 400 touching inside the list 3303, the ultrasound apparatus 1000 may display a list 3305 including the plurality of gain value sets also on the first display unit 100. In addition, the ultrasound apparatus 1000 may mark an indicator 3306 representing the current location of the pointer 400 in the list 3305 displayed on the first display unit 100. For example, if the pointer 400 is located on a second gain valueset 3304 on the second display unit 200, the ultrasound apparatus 1000 may mark the indicator 3306 of a star shape on the second gain value set 3304 in the list 3305 displayed on the first display unit 100.

If the user drags the pointer 400 in contact with the second display unit 200, the ultrasound apparatus 1000 may move the indicator 3306 according to the movement of the pointer 400. For example, if the user drags the pointer 400 from a first gain value set to the second gain value set 3304 (2010), the ultrasound apparatus 1000 may move the indicator 3306 marked on the second display unit 200 from a first gain value set to the second gain value set 3304.

According to the exemplary embodiment, the ultrasound apparatus 1000 may receive an input for selecting one gain value set in the list 3303 displayed on the second display unit 200. For example, the ultrasound apparatus 1000 may receive an input for touching the second gain value set 3304. Here, a pressure of touching the second gain value set 3304 is equal to or greater than a critical value, the ultrasound apparatus 1000 may determine that the user selects the second gain value set 3304 in the list 3303. In this case, the ultrasound apparatus 1000 may read gain values corresponding to a plurality of depth sections included in the selected second gain value set 3304, from a storage medium (e.g., a memory, an external storage medium, or a cloud server).

Referring to FIG. 33C, the ultrasound apparatus 1000 may move adjustment buttons on a plurality of slide bars included in a gain control item 3307, according to the gain values corresponding to the plurality of depth sections included in the selected second gain value set 3304.

The ultrasound apparatus 1000 may display a gain line 3308 corresponding to the selected second gain value set on the first display unit 100. For example, the ultrasound apparatus 1000 may generate the gain line 3308 by connecting the gain values included in the second gain value set, and may display the gain line 3308 next to the ultrasound image 3300 displayed on the first display unit 100.

According to the exemplary embodiment, the ultrasound apparatus 1000 may mark an indicator 3309 that indicates the location of the pointer 400 in the gain control item 3307 on the gain line 3308. For example, if the pointer 400 is located on a seventh slide bar, the ultrasound apparatus 1000 determines a seventh depth value corresponding to the seventh slide bar, and marks an indicator 3309 at a location of the gain line 3308, which represents the seventh depth value.

According to the exemplary embodiment, the ultrasound apparatus 1000 may apply the gain values corresponding to the plurality of depth sections included in the second gain value set to the ultrasound echo signal. In this case, the brightness of the ultrasound image 3300 by the depth sections may be changed.

Figure 34:
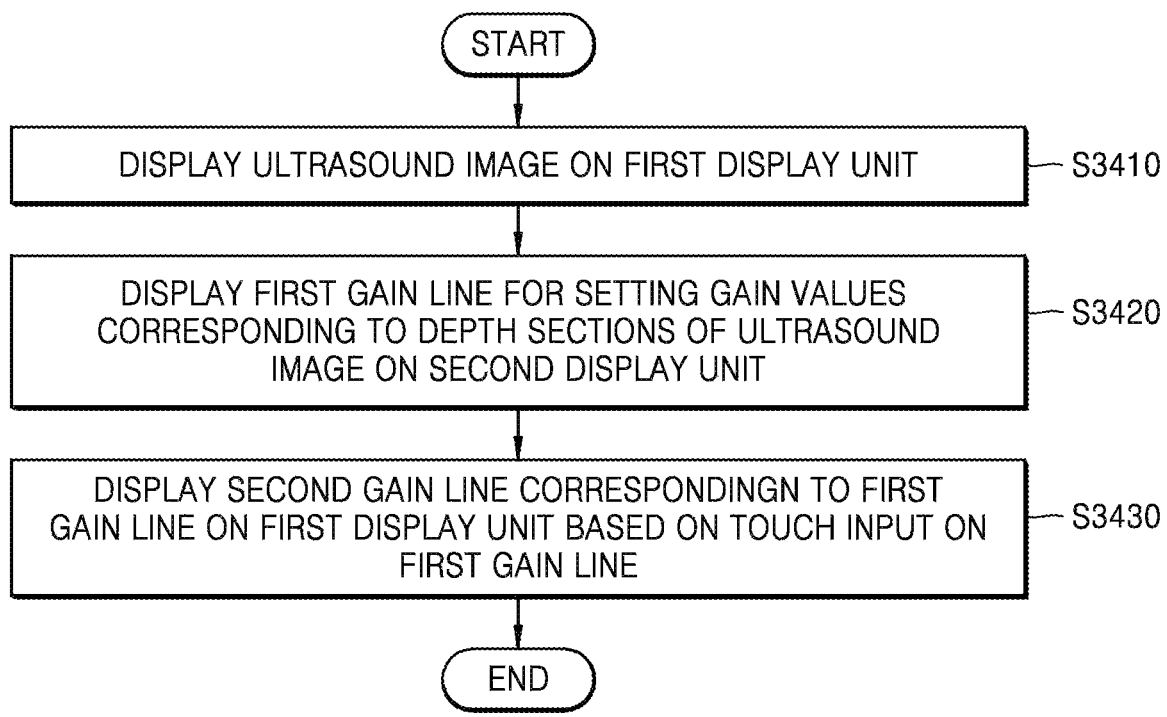
FIG. 34 is a flowchart illustrating a method for an ultrasound apparatus to display a gain line on a plurality of display units, according to an exemplary embodiment.

FIG. 34 is a flowchart illustrating a method for the ultrasound apparatus 1000 to display a gain line on a plurality of display units.

In operation S3410, the ultrasound apparatus 1000 may display an ultrasound image on the first display unit 100.

According to the exemplary embodiment, the ultrasound apparatus 1000 may display real-time ultrasound images obtained via the probe 20 on the first display unit 100. In addition, according to the exemplary embodiment, the ultrasound apparatus 1000 may display ultrasound images stored in advance in a storage medium on the first display unit 100.

In addition, the ultrasound image may be at least one of a B mode image, a C mode image, a D mode image, an M mode image, and an elastic mode image, but is not limited thereto. The ultrasound image according to the exemplary embodiment may be a 2D image, a 3D image, or a 4D image.

In operation S3420, the ultrasound apparatus 1000 may display a first gain line for setting gain values corresponding to depth sections of the ultrasound image on the second display unit 200. According to the exemplary embodiment, the first gain line may be one of the control items displayed on the second display unit 200.

According to the exemplary embodiment, the ultrasound apparatus 1000 may display the first gain line on the second display unit 200, together with the ultrasound image displayed on the first display unit 100. For example, the ultrasound apparatus 1000 may display the ultrasound image on a first region of the second display unit 200, and may display the first gain line on a second region of the second display unit 200.

In operation S3430, the ultrasound apparatus 1000 may display a second gain line corresponding to the first gain line on the first display unit 100, based on a touch input for touching the first gain line.

According to the exemplary embodiment, the ultrasound apparatus 1000 may recognize the pointer 400 touching the first gain line on the second display unit 200 via at least one sensor. The touch may include a contact-type touch and a non contact-type touch (hovering). The at least one sensor may be at least one of a touch sensor, a pressure sensor, a proximity sensor, an image sensor, a depth sensor, and an infrared ray sensor, but is not limited thereto.

The method for the ultrasound apparatus 1000 to sense the location of the pointer 400 is described above with reference to FIGS. 5 to 8, and detailaed descriptions thereof are omitted.

According to the exemplary embodiment, the first gain line displayed on the second display unit 200 and the second gain line displayed on the first display unit 100 may be lines formed by connecting gain values corresponding to depth sections of the ultrasound image. For example, the ultrasound apparatus 1000 may extract a plurality of gain values represented respectively by the points on the first gain line in response to the touch input for touching the first gain line, and may generate the second gain line by using the extracted plurality of gain values.

Therefore, the first gain line and the second gain line may be similar to each other. However, a length of the first gain line and a length of the second gain line may be different from each other according to a ratio between screen sizes of the first display unit 100 and the second display unit 200. For example, if the first display unit 100 is twice greater than the second display unit 200, the length of the first gain line may be twice longer than that of the second gain line.

The ultrasound apparatus 1000 may determine the lengths of the first gain line and the second gain line as taking the ratio between sizes of the ultrasound images displayed on the first display unit 100 and on the second display unit 200 into account. For example, if a ratio between the sizes of the ultrasound images displayed on the first display unit 100 and the second display unit 200 is 3:2, the length of the second gain line may be determined so that the ratio between the lengths of the first gain line and the second gain line is 3:2.

According to the exemplary embodiment, the ultrasound apparatus 1000 may determine a size of the second gain line in consideration of an entire depth value or a longitudinal length of the ultrasound image displayed on the first display unit 100.

According to the exemplary embodiment, if the pointer 400 touches the first gain line, the ultrasound apparatus 1000 may display the second gain line corresponding to the first display line on the first display unit 100, together with the ultrasound image. For example, the ultrasound apparatus 1000 may display the second gain line on the ultrasound image or next to the ultrasound image.

According to the exemplary embodiment, the ultrasound apparatus 1000 may display the second gain line along with a depth axis of the ultrasound image. For example, the ultrasound apparatus 1000 may display the second gain line at a side of the ultrasound image so that the depth values represented by the points on the second gain line may be matched with depth values in the ultrasound image. Here, the ultrasound apparatus 1000 may display the second gain line on the first display unit 100 so that an uppermost point of the second gain line matches with the lowest depth value of the ultrasound image and a lowermost point of the second gain line matches with the highest depth value of the ultrasound image.

According to the exemplary embodiment, the ultrasound apparatus 1000 may mark an indicator representing a point on the first gain line touched by the pointer 400 on the second gain line. For example, if the pointer 400 is located at a first depth value on the first gain line, the ultrasound apparatus 1000 may mark the indicator at a location representing the first depth value on the second gain line.

According to the exemplary embodiment, if the location of the pointer 400 on the first gain line is changed, the ultrasound apparatus 1000 may move the indicator marked on the second gain line according to the changed location of the pointer 400. For example, if the pointer 400 moves downward along with the first gain line, the ultrasound apparatus 1000 may also move the indicator downward along with the second gain line. If the touching location of the pointer 400 on the first gain line is changed to a new location, the ultrasound apparatus 1000 may determine a point on the second gain line, which corresponds to the new location, and may move the indicator to the new location.

According to the exemplary embodiment, the ultrasound apparatus 1000 may receive an input for changing the first gain value set corresponding to the first gain line to a second gain value set via the first gain line. In this case, the ultrasound apparatus 1000 may change a shape of the second gain line displayed on the first display unit 100, based on the second gain value set. For example, if the first gain line is changed from a straight line to an S-curved line, the ultrasound apparatus 1000 may change the second gain line from the straight line to the S-curved line.

According to the exemplary embodiment, when the touch input for touching the first gain line is finished, the ultrasound apparatus 1000 may stop displaying the second gain line. For example, if the user takes his/her finger touching the first gain line off the second display unit 200, the ultrasound apparatus 1000 may not display the second gain line on the first display unit 100 any more.

Hereinafter, an operation of the ultrasound apparatus 1000 for providing a plurality of gain lines through a plurality of display units will be described below with reference to FIGS. 35A to 35F.

FIGS. 35A to 35F are diagrams illustrating an example, in which the ultrasound apparatus 1000 displays gain lines on a touch screen and a main screen.

Referring to FIG. 35A, the ultrasound apparatus 1000 may display an ultrasound image 3500 on the first display unit 100, and may display a plurality of control items related to the ultrasound image 3500 on the second display unit 200. Here, the plurality of control items may be displayed separately on a first page 3510 and a second page 3520.

The ultrasound apparatus 1000 may display the first page 3510 including a color invert item, an M line item, a dual live item, an ADVR item, and an alpha blending item on the second display unit 200. Here, the ultrasound apparatus 1000 may receive a page changing gesture 3501 that the user swipes the first page 3510 to a left side in contact with the second display unit 200.

Figure 35B:
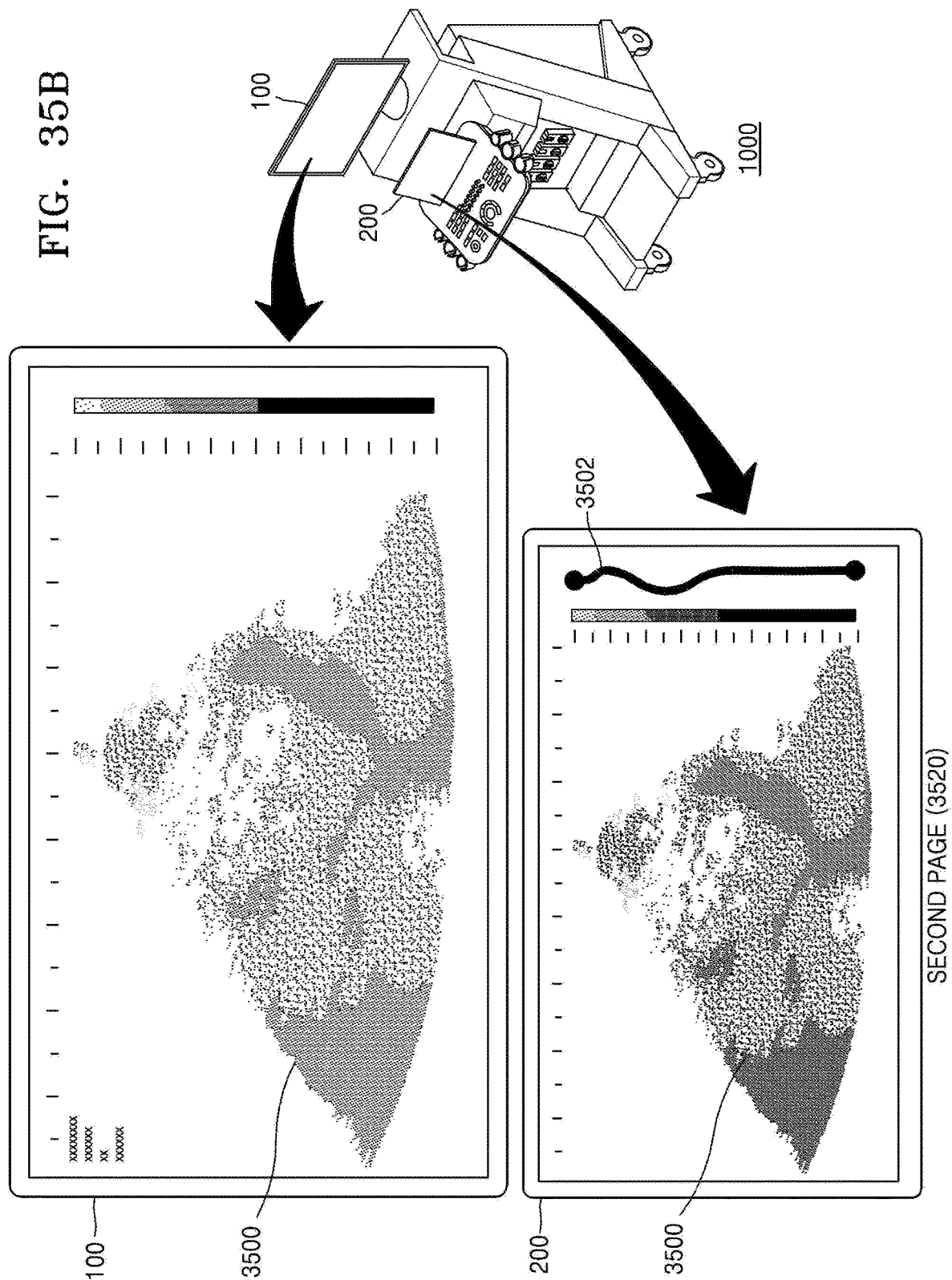

Referring to FIG. 35B, the ultrasound apparatus 1000 may display the second page 3520, instead of the first page 3510, on the second display unit 200 in response to the page changing gesture 3501. The second page 3520 displayed on the second display unit 200 may include the ultrasound image 3500 and a first gain line 3502. The first gain line 3502 may be a user interface for adjusting a TGC value according to the depth sections.

Figure 35C:
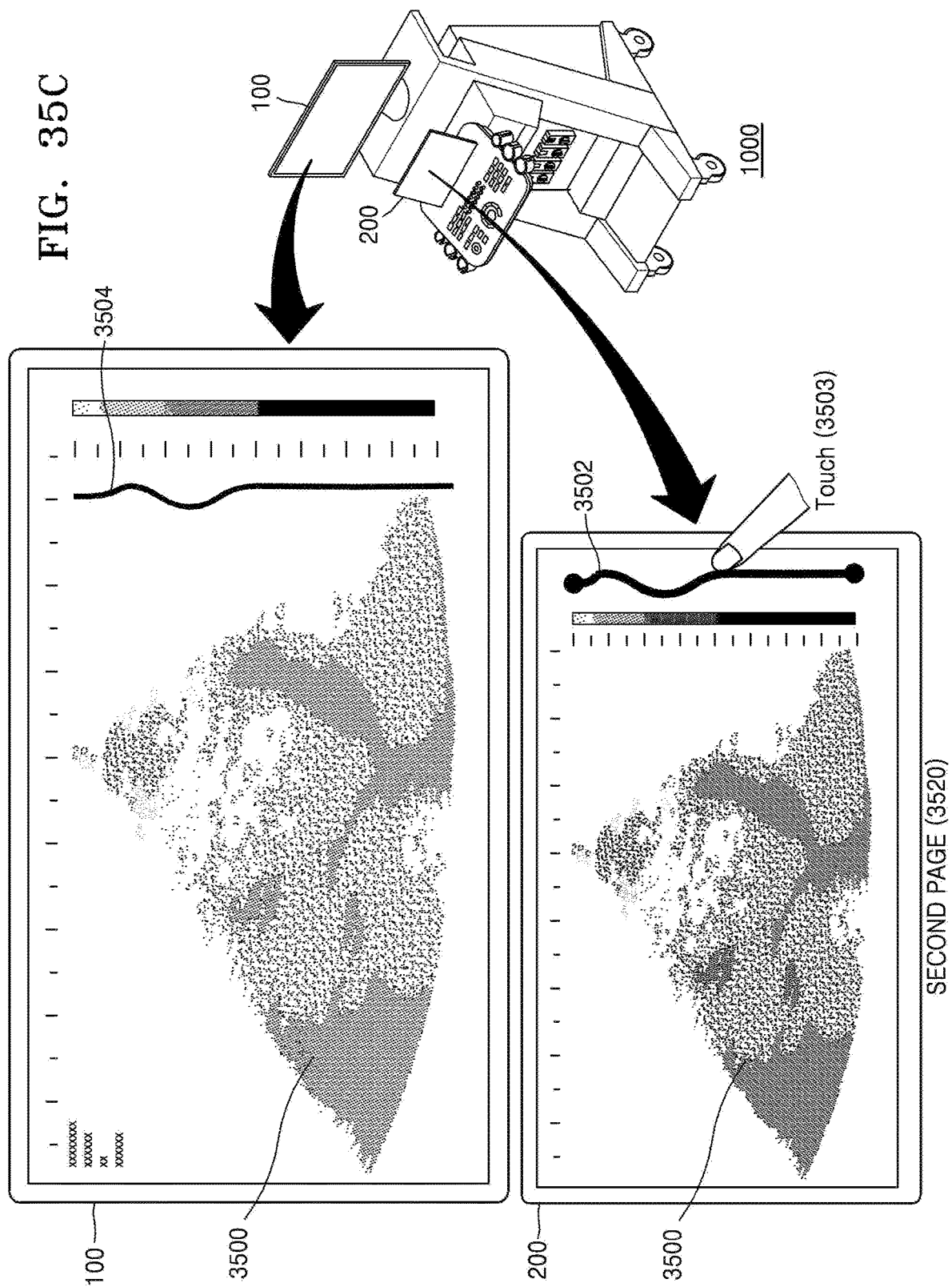

Referring to FIG. 35C, the ultrasound apparatus 1000 may receive a gesture 3503 touching the first gain line 3502 included in the second page 3520. Here, the ultrasound apparatus 1000 may display a second gain line 3504 corresponding to the first gain line 3502 on the first display unit 100. Here, the ultrasound apparatus 1000 may display the second gain line 3504 along with a depth axis of the ultrasound image 3500 displayed on the first display unit 100.

Figure 35D:
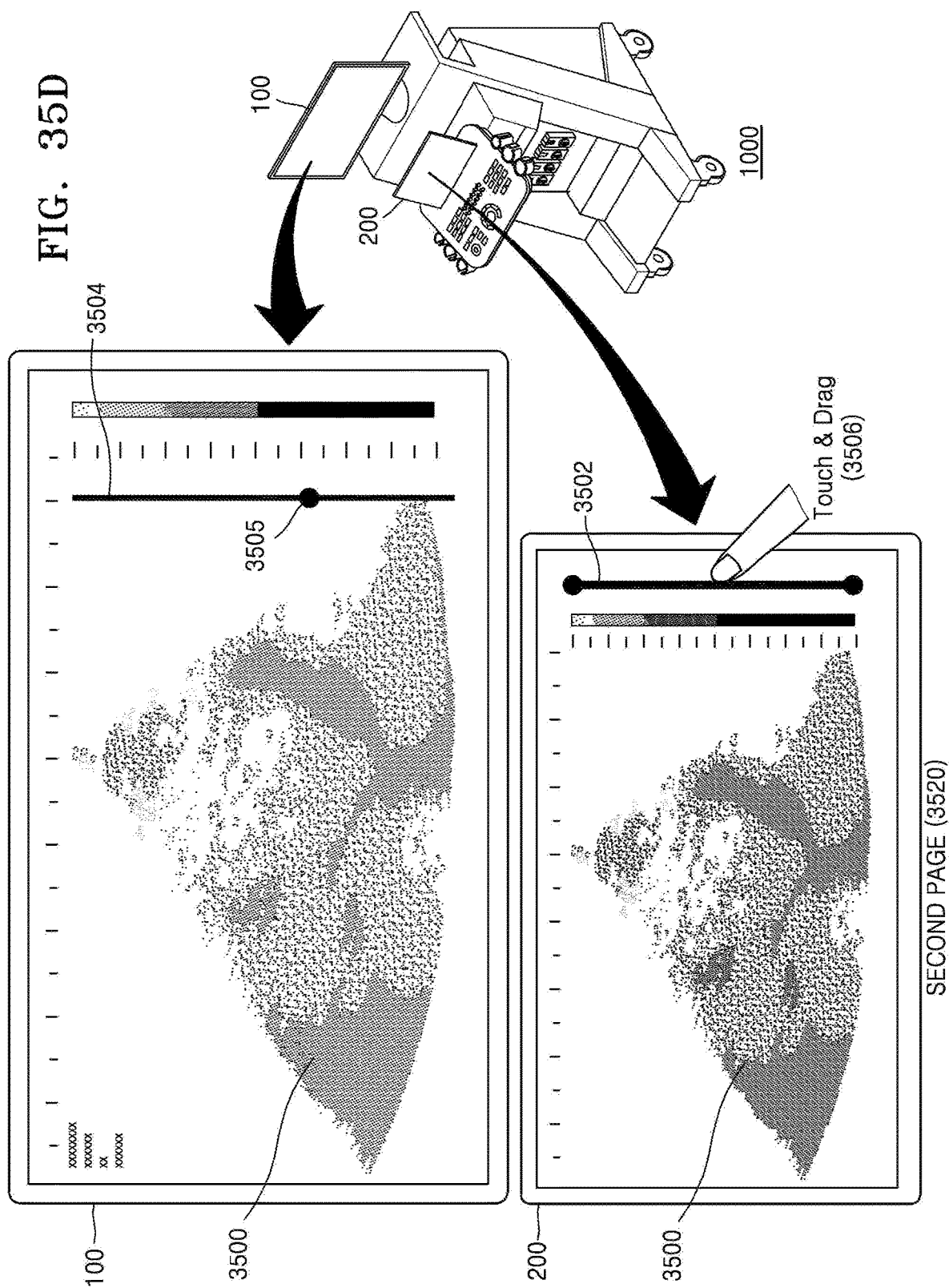

Referring to FIG. 35D, the ultrasound apparatus 1000 may receive an input for changing the first gain value set corresponding to the first gain line 3502 into a second gain value set by using the first gain line 3502. For example, the ultrasound apparatus 1000 may receive a touch and drag input 3506 for changing the first gain line 3502 of a curved line shape into a straight line. In this case, the first gain value set corresponding to the first gain line 3502 of the curved shape may be changed into the second gain value set corresponding to the straight line.

The ultrasound apparatus 1000 may change the shape of the second gain line 3504 displayed on the first display unit 100, based on the second gain value set. For example, since the first gain line 3502 is changed from the curved line type to the straight line type, the ultrasound apparatus 1000 may change the second gain line 3504 from a curved line type to a straight line type.

The ultrasound apparatus 1000 may mark an indicator 3505 that indicates a location of the pointer 400 on the first gain line 3502 on the second gain line 3504. For example, if the pointer 400 is located at a tenth depth value on the first gain line 3502, the ultrasound apparatus 1000 may mark the indicator 3505 at a location representing the tenth depth value on the second gain line.

Referring to FIG. 35E, the ultrasound apparatus 1000 may receive a page changing gesture 3507 that the user swipes the second page 3520 to a right side in contact with a point where the first gain line 3502 is not displayed in the second page 3520.

Here, since the pointer 400 does not touch the first gain line 3502 any more, the ultrasound apparatus 1000 may not display the second gain line 3504 on the first display unit 100 any more (3508).

Figure 35F:
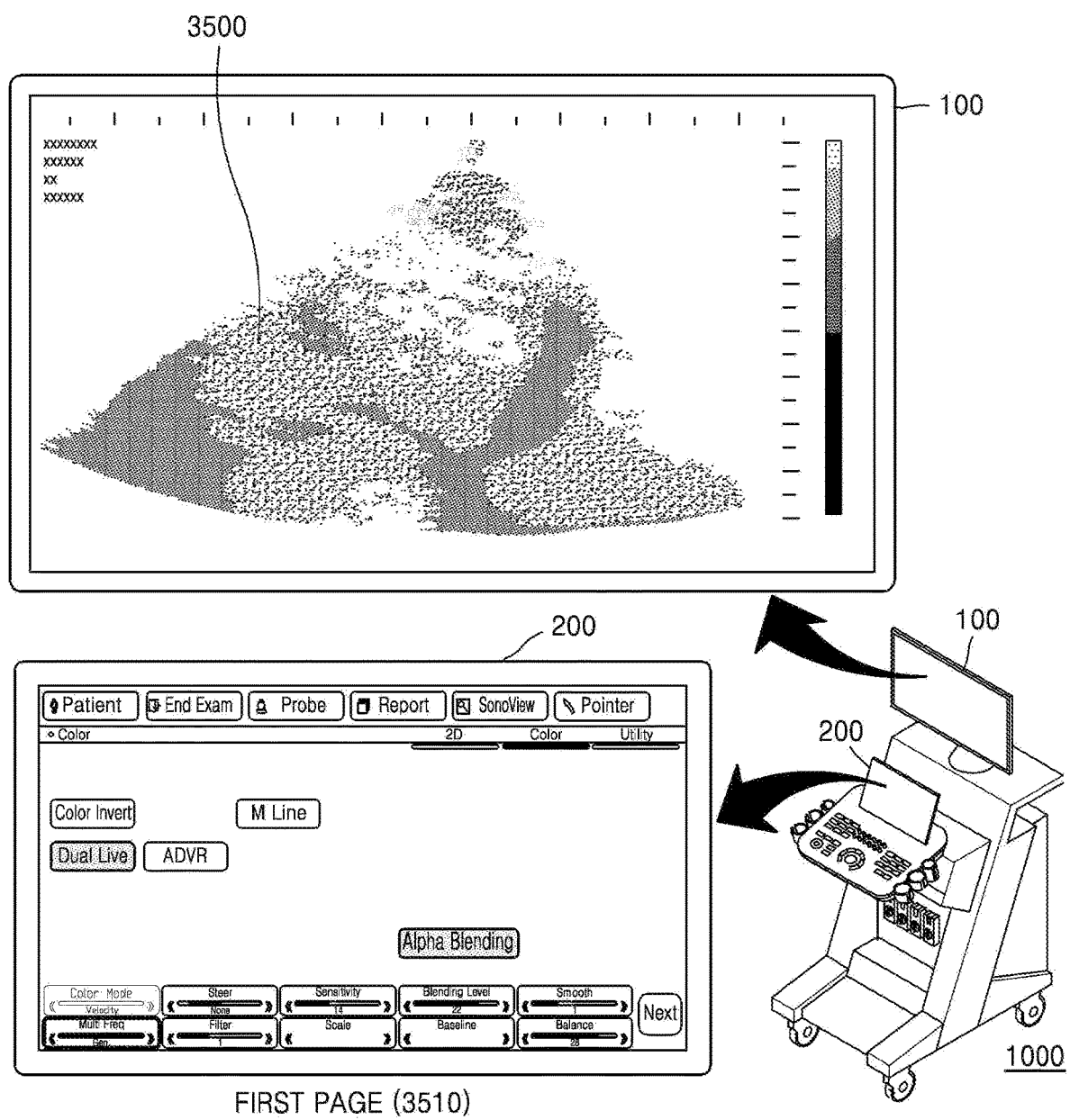

Referring to FIG. 35F, the ultrasound apparatus 1000 may display the first page 3510, instead of the second page 3520, on the second display unit 200 in response to the page changing gesture 3507.

Figure 36:
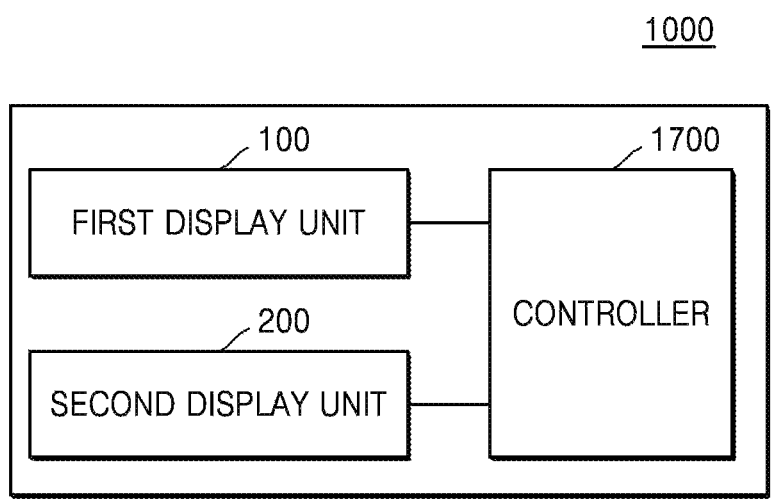
FIGS. 36 and 37 are block diagrams of an ultrasound apparatus according to an exemplary embodiment.
Figure 37:
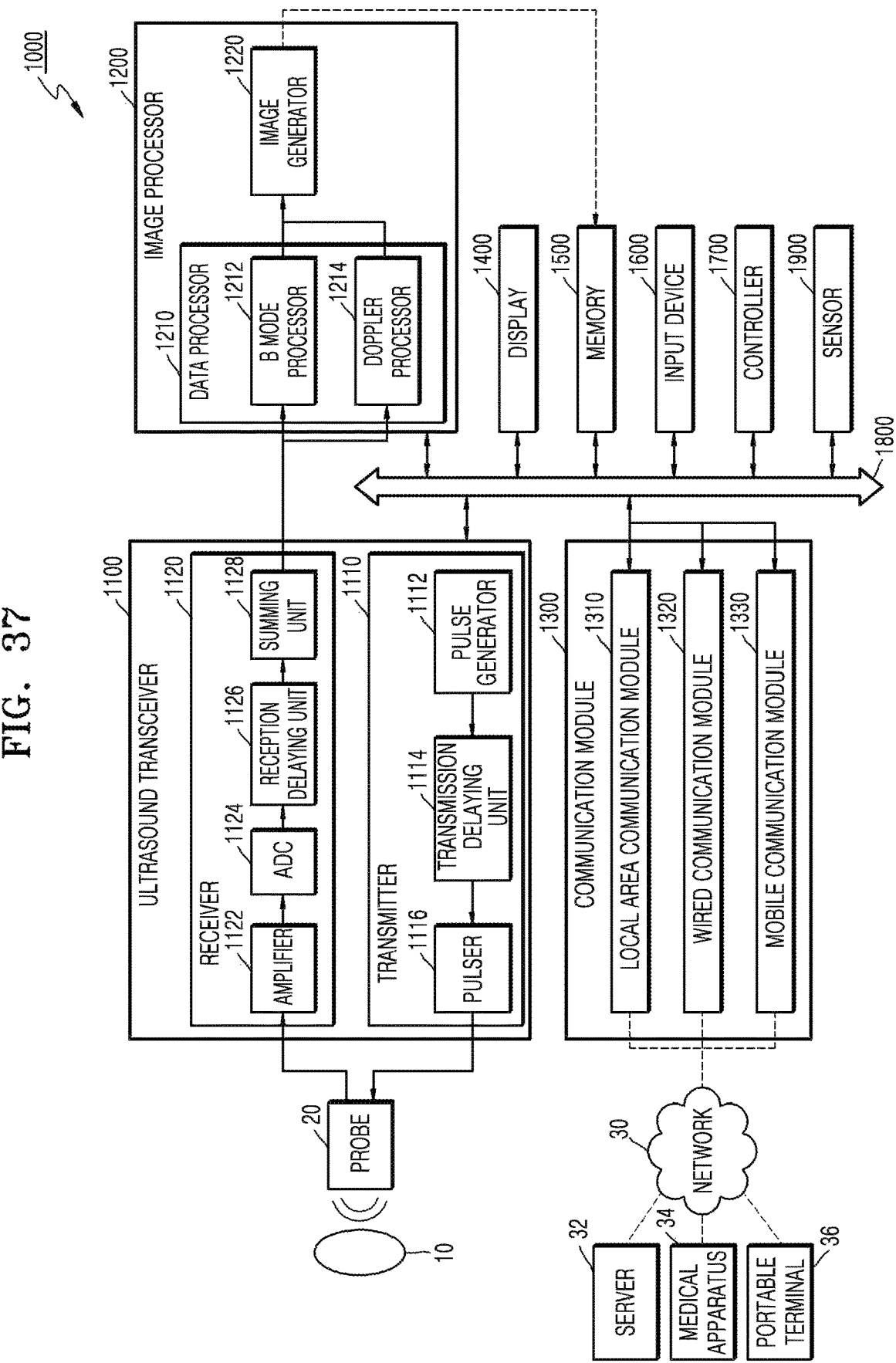

FIGS. 36 and 37 are block diagrams of an ultrasound apparatus 1000 according to an exemplary embodiment.

As shown in FIG. 36, the ultrasound apparatus 1000 according to the exemplary embodiment may include the first display unit 100, the second display unit 200, and a controller 1700. The first display unit 100 and the second display unit 200 may communicate with the controller 1700 through a wireless or wired connection. However, not all of the components shown in the drawings are essential elements. The ultrasound apparatus 1000 may include more or less components than those of FIG. 36.

For example, as shown in FIG. 37, the ultrasound diagnosis apparatus 1000 may include the probe 20, an ultrasound transceiver 1100, an image processor 1200, a communication module 1300, a display 1400, a memory 1500, an input device 1600, and a controller 1700, a sensor 1900, which may be connected to one another via buses 1800.

The ultrasound apparatus 1000 may be a cart type apparatus or a portable type apparatus. Examples of portable ultrasound apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound apparatus 1000 by wire or wirelessly, and according to exemplary embodiments, the ultrasound apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some exemplary embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and processing the ultrasound data by data processor 1210. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an exemplary embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound apparatus 1000 on a screen image via a graphical user interface (GUI). In addition, the ultrasound apparatus 1000 may include two or more displays 1400 according to exemplary embodiments. For example, the ultrasound apparatus 1000 may include the first display unit 100 and the second display unit 200. Here, the first display unit 100 may be the main screen displaying ultrasound images. The second display unit 200 may be a control screen for displaying a plurality of control items. The first display unit 100 and the second display unit 200 are described above with reference to FIG. 1, and thus, detailed descriptions thereof are omitted.

The communication module 1300 is connected to a network 30 by wire or wirelessly to communicate with an external device or a server 32. For example, the communication module 1300 is connected to the network 30 by wire or wirelessly to exchange data with a medical apparatus 34 or a portable terminal 36.

The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object 10, e.g., an ultrasound image, ultrasound data, and Doppler data of the object 10, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server 32 and utilizes the received information to diagnose the patient. Furthermore, the communication module 1300 may perform data communication not only with a server or a medical apparatus in a hospital, but also with a portable terminal of a medical doctor or patient.

The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an exemplary embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound apparatus 1000. For example, the memory 1500 may store medical data related to diagnosis of an object, such as ultrasound data and an ultrasound image that are input or output, and may also store algorithms or programs which are to be executed in the ultrasound apparatus 1000. The memory 1500 may store a plurality of control items for adjusting parameters related to the ultrasound image, information about user interfaces linked respectively to the plurality of control items, information about preset gain values (e.g., preset TGC or preset LGC), information about gestures matched to certain functions, etc.

The memory 1500 may be any of various storage media, e.g., a flash memory, a hard disk drive, EEPROM, etc. Furthermore, the ultrasound apparatus 1000 may utilize web storage or a cloud server that performs the storage function of the memory 1500 online.

The input device 1600 refers to a means via which a user inputs data for controlling the ultrasound apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc. According to the exemplary embodiment, the input device 1600 may include the second display unit 200 displaying the plurality of control items.

The controller 1700 may control all operations of the ultrasound apparatus 1000. In other words, the controller 1700 may control operations among the probe 20, the ultrasound transceiver 1100, the image processor 1200, the communication module 1400, the display unit 1300, the memory 1500, and the input device 1600.

All or some of the probe 20, the ultrasound transceiver 1100, the image processor 1200, the communication module 1300, the display 1400, the memory 1500, the input device 1600, and the controller 1700 may be implemented as software modules. At least one of the ultrasound transmission/reception unit 1100, the image processor 1200, and the communication module 1300 may be included in the controller 1700; however, the inventive concept is not limited thereto.

The controller 1700 may determine at least one control item from among the plurality of control items based on a location of the pointer 400 on the second display unit 200. For example, the controller 1700 may determine at least one control item displayed within a predetermined distance from the pointer 400. Otherwise, the controller 1700 may determine at least one control item by selecting a menu group corresponding to the location of the pointer 400, from among a plurality of menu groups displayed on the second display unit 200.

The controller 1700 may control the first display unit 100 to display the determined at least one control item and an indicator indicating the location of the pointer 400 with the ultrasound image. For example, the controller 1700 may mark the indicator on the at least one control item.

The controller 1700 may change a location of the indicator marked on the first display unit 100 since the location of the pointer 400 on the second display unit 200 is changed.

The controller 1700 may display the at least one control item and the indicator representing the location of the pointer 400 to be overlaid on the ultrasound image displayed on the first display unit 100. Here, the controller 1700 may determine a transparency of the at least one control item displayed on the ultrasound image, based on predefined transparency information. The controller 1700 may display the at least one control item and the indicator representing the location of the pointer to be transparent on the ultrasound image, according to the determined transparency.

The controller 1700 may display the ultrasound image on a first region of the first display unit 100 and may display at least one control item including the indicator on a second region of the first display unit 100.

The controller 1700 may receive a first input for selecting one control item from among a plurality of control items via the second display unit 200. The first input for selecting the control item may be different from a second input for changing the location of the indicator. The controller 1700 may display a window corresponding to the selected control item on the first display unit 100.

The controller 1700 may select a first control item from among the plurality of control items from among the plurality of control items displayed on the second display unit 200, based on the location of the pointer 400 touching the second display unit 200. The controller 1700 may determine a second display format that is different from a first display format in which the first control item is displayed on the second display unit 200, and may control the first display unit 100 to display the first control item in the second display format. According to the exemplary embodiment, the second display format may be simplified when comparing with the first display format.

The controller 1700 senses the location of the pointer 400 touching the first control item displayed in the first display format, and may mark an indicator representing the location of the pointer 400 on the first control item displayed in the second display format.

The controller 1700 may move the indicator on the first control item displayed in the second display format, according to the change in the location of the pointer 400 on the first control item displayed in the first display format.

The controller 1700 may receive a drag input for dragging on the first control item displayed in the first display format, and may change the location of the indicator on the first control item displayed in the second display format according to the drag input.

If a touching on the first control item displayed in the first display format on the second display unit 200 is sensed, the controller 1700 may display the first control item in the second display format on the first display unit 100 while maintaining the first display format of the first control item on the second display unit 200.

The controller 1700 may display the first control item in the second display format to be overlaid on the ultrasound image of the first display unit 100. Alternately, the controller 1700 may display the ultrasound image on a first region of the first display unit 100 and may display the first control item in the second display format on a second region of the first display unit 100. Here, the first region and the second region may be different from each other.

The controller 1700 may control the first display unit 100 to display a gain line formed by connecting gain values corresponding to locations of the adjustment buttons on a plurality of slide bars, together with the ultrasound image, based on the location of the pointer 400 touching the second display unit 200.

The controller 1700 may mark an indicator representing a depth section corresponding to the location of the pointer 400 on the first region, on the gain line displayed on the first display unit 100.

The controller 1700 may move the indicator marked on the gain line when the location of the pointer 400 in the first region is changed.

The controller 1700 may receive an input for moving at least one of the adjustment buttons on the plurality of slide bars via the second display unit 200. The controller 1700 may change a shape of the gain line displayed on the first display unit 100 based on the location of at least one adjustment button.

The controller 1700 may determine an input mode based on a kind of the touch gesture of the pointer 400 sensed via the second display unit 200. Here, the input mode may include a depth selection mode for selecting one depth section from among the depth sections of the ultrasound image, and a gain change mode for changing the gain value, but is not limited thereto.

The controller 1700 may determine the depth selection mode as the input mode when the touch gesture of the pointer 400 is a one-finger gesture, and may determine the gain change mode as the input mode when the touch gesture of the pointer 400 is a multi-finger gesture.

For example, the controller 1700 may move the indicator marked on the gain line to a first depth section in response to a first drag gesture that drags one finger upward or downward in contact with the first region. In addition, the controller 1700 may adjust the gain value in the first depth section in response to a second drag gesture that drags at least two fingers in a left or right direction while the at least two fingers are in contact with the first region. The controller 1700 may change a shape of the gain line displayed on the first display unit 100 based on the adjusted gain value.

The controller 1700 may receive an input for selecting one preset gain value set from among a plurality of preset gain value sets, via the second display unit 200. The controller 1700 may move at least one adjustment button from among the adjustment buttons on the plurality of slide bars, according to the selected preset gain value set. The controller 1700 may display the gain line corresponding to the selected preset gain value set on the first display unit 100.

The controller 1700 may control the first display unit 100 to display a second gain line corresponding to a first gain line with the ultrasound image, based on a touch input for touching the first gain line displayed on the second display unit. Here, the first gain line and the second gain line may be lines obtained by connecting the gain values corresponding to the depth sections of the ultrasound image.

The controller 1700 may control the first display unit 100 to display the ultrasound image on the first region and to display the second gain line on the second region of the first display unit 100.

The controller 1700 may mark an indicator representing a touched location on the first gain line, on the second gain line. The controller 1700 may move the indicator marked on the second gain line, when the touched location on the first gain line is changed.

The controller 1700 may receive an input for changing a first gain value set corresponding to the first gain line to a second gain value set, via the first gain line. The controller 1700 may change the shape of the second gain line displayed on the first display unit 100 based on the second gain value set.

The controller 1700 may stop displaying the second gain line, when the touch input for touching the first gain line has finished.

The sensor 1900 may include at least one sensor for sensing the pointer 400 located on the second display unit 200 and/or a location of the pointer 400. The at least one sensor may include one of a touch sensor, a pressure sensor, a proximity sensor, an image sensor (e.g., a camera), a depth sensor (e.g., a depth camera), and an infrared ray sensor (e.g., an infrared ray camera), but is not limited thereto.

One or more of the exemplary embodiments may be implemented as computer readable codes in a computer readable medium. The computer readable recording medium may include a program instruction, a local data file, a local data structure, or a combination thereof. The computer readable recording medium may be specific to exemplary embodiments. The computer readable recording medium includes all types of recordable media in which computer readable data are stored. Examples of the computer readable recording medium include a magnetic medium, such as a hard disk, a floppy disk and a magnetic tape, an optical medium, such as a CD-ROM and a DVD, a magneto-optical medium, such as an optical disk, and a hardware memory, such as a ROM, a RAM and a flash memory, specifically configured to store and execute program instructions. Furthermore, the computer readable recording medium may be implemented in the form of a transmission medium, such as light, wire or waveguide, to transmit signals which designate program instructions, local data structures and the like. Examples of the program instruction include machine code, which is generated by a compiler, and a high level language, which is executed by a computer using an interpreter and so on.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An ultrasound apparatus comprising:
a first display configured to display an ultrasound image;
a control panel comprising a second display other than the first display and configured to display a plurality of control items related to the ultrasound image; and
a controller configured to:
determine that a user is scanning the ultrasound image via a probe or a sensor included in the probe;
display, on the first display, the plurality of control items or some of the plurality of control items displayed on the second display and an indicator representing a location of an input tool together with the ultrasound image, based on sensing the input tool within a predefined distance from the second display and based on determining that scanning of the ultrasound image is being performed by the probe;
change a location of the indicator displayed on the first display and display the indicator on a control item, in response to the location of the input tool hovering within the predefined distance from the second display being changed;
receive a first input for selecting the control item from among the plurality of control items;
select the control item from among the plurality of control items or some of the plurality of control items displayed on the second display, based on a touched location of the first input located on the second display, by selecting a menu group corresponding to the location of the input tool, from among a plurality of menu groups displayed on the second display;
control the first display to display the selected control item, a subset of the plurality of menu groups that corresponds to the selected menu group, and the indicator representing the location of the input tool together with the ultrasound image, wherein the first input for selecting the control item comprises a touch gesture and a second input for changing the location of the indicator comprises a hovering gesture; and
control the first display to remove the plurality of control items or some of the plurality of control items displayed on the first display based on the input tool not being sensed within the predefined distance from the second display while the ultrasound image is being scanned by the probe.

2. The ultrasound apparatus of claim 1, further comprising at least one sensor configured to detect the location of the input tool located on the second display.

3. The ultrasound apparatus of claim 2, wherein the at least one sensor comprises at least one selected from among a touch sensor, a pressure sensor, a proximity sensor, an image sensor, a depth sensor, and an infrared ray sensor.

4. The ultrasound apparatus of claim 1, wherein the ultrasound image comprises a real-time ultrasound image scanned via the probe.

5. The ultrasound apparatus of claim 1, wherein the first display is further configured to display the selected control item, the subset of the plurality of menu groups, and the indicator so that the selected control item, the subset of the plurality of menu groups, and the indicator overlay the ultrasound image.

6. The ultrasound apparatus of claim 5, wherein the controller is further configured to determine a transparency of the selected control item and the subset of the plurality of menu groups displayed on the ultrasound image, based on predefined transparency information.

7. The ultrasound apparatus of claim 1, wherein the controller is further configured to display the ultrasound image on a first region of the first display and display the selected control item, the subset of the plurality of menu groups, and the indicator on a second region of the first display.

8. The ultrasound apparatus of claim 1, wherein the controller is further configured to display a window corresponding to the selected control item on the first display.

9. The ultrasound apparatus of claim 1, wherein the controller is further configured to display the ultrasound image displayed on the first display, on a predetermined region of the second display.

10. A method of providing information via an ultrasound apparatus, the method comprising:
displaying an ultrasound image on a first display;
displaying a plurality of menu groups and a plurality of control items related to the ultrasound image on a second display included in a control panel;
determining that a user is scanning the ultrasound image via a probe or a sensor included in the probe;
displaying, on the first display, the plurality of control items or some of the plurality of control items displayed on the second display and an indicator representing a location of an input tool together with the ultrasound image, based on sensing the input tool within a predefined distance from the second display and based on determining that scanning of the ultrasound image is being performed by the probe;
changing a location of the indicator displayed on the first display and display the indicator on a control item, in response to the location of the input tool hovering within the predefined distance from the second display being changed;
receiving a first input for selecting the control item from among the plurality of control items;
selecting the control item from among the plurality of control items or some of the plurality of control items displayed on the second display, based on a touched location of the first input located on the second display, by selecting a menu group corresponding to the location of the input tool, from among a plurality of menu groups displayed on the second display;
displaying the selected control item, a subset of the plurality of menu groups that corresponds to the selected menu group, and the indicator representing the location of the input tool on the first display, together with the ultrasound image, wherein the first input for selecting the control item comprises a touch gesture and a second input for changing the location of the indicator comprises a hovering gesture; and
controlling the first display to remove the plurality of control items or some of the plurality of control items displayed on the first display based on the input tool not being sensed within the predefined distance from the second display while the ultrasound image is being scanned by the probe.

11. A non-transitory computer readable medium comprising instructions executable by a processor to perform:
displaying an ultrasound image on a first display;
displaying, on a second display of a control panel that is separate from the first display, a plurality of menu groups and a plurality of control items configured to control to adjust the ultrasound image;
determining that a user is scanning the ultrasound image via a probe or a sensor included in the probe;
displaying, on the first display, the plurality of control items or some of the plurality of control items displayed on the second display and an indicator representing a location of an input tool together with the ultrasound image, based on sensing the input tool within a predefined distance from the second display and based on determining that scanning of the ultrasound image is being performed by the probe;
changing a location of the indicator displayed on the first display and display the indicator on a control item, in response to the location of the input tool hovering within the predefined distance from the second display being changed;
receiving a first input for selecting the control item from among the plurality of control items,
selecting the control item from among the plurality of control items or some of the plurality of control items displayed on the second display based on a touched location of the first input located on the second display, by selecting a menu group corresponding to the location of the input tool, from among a plurality of menu groups displayed on the second display;
controlling the first display to display the selected control item, a subset of the plurality of menu groups that corresponds to the selected menu group, and the indicator representing the location of the input tool together with the ultrasound image, wherein the first input for selecting the control item comprises a touch gesture and a second input for changing the location of the indicator comprises a hovering gesture; and
controlling the first display to remove the plurality of control items or some of the plurality of control items displayed on the first display based on the input tool not being sensed within the predefined distance from the second display while the ultrasound image is being scanned by the probe.

12. The non-transitory computer readable medium of claim 11, wherein the instructions are executable by the processor to further perform:
detecting, by a sensor, the location of the input tool corresponding to the second display.

13. The non-transitory computer readable medium of claim 12, wherein the sensor comprises at least one selected from among a touch sensor, a pressure sensor, a proximity sensor, an image sensor, a depth sensor, and an infrared ray sensor.

* * * * *